US009464064B2

(12) United States Patent
Aube et al.

(10) Patent No.: US 9,464,064 B2
(45) Date of Patent: Oct. 11, 2016

(54) HCV HELICASE INHIBITORS AND METHODS OF USE THEREOF

(75) Inventors: Jeffrey Aube, Lawrence, KS (US); Brian Scott Jonathan Blagg, Lawrence, KS (US); Kevin John Frankowski, Lawrence, KS (US); David Norman Frick, Bayside, WI (US); Kelin Li, Lawrence, KS (US); Frank John Schoenen, Lawrence, KS (US)

(73) Assignees: University of Kansas, Lawrence, KS (US); UWM Research Foundation, Inc., Milwaukee, WI (US)

( * ) Notice: Subject to any disclaimer, the term of this patent is extended or adjusted under 35 U.S.C. 154(b) by 0 days.

(21) Appl. No.: 14/343,465

(22) PCT Filed: Sep. 7, 2012

(86) PCT No.: PCT/US2012/054130
§ 371 (c)(1),
(2), (4) Date: Apr. 11, 2014

(87) PCT Pub. No.: WO2013/036749
PCT Pub. Date: Mar. 14, 2013

(65) Prior Publication Data
US 2014/0227225 A1    Aug. 14, 2014

Related U.S. Application Data

(60) Provisional application No. 61/531,860, filed on Sep. 7, 2011.

(51) Int. Cl.
*C07D 417/04* (2006.01)
*C07D 417/14* (2006.01)
*C07D 277/66* (2006.01)
*A61K 45/06* (2006.01)
*A61K 31/13* (2006.01)
*A61K 31/428* (2006.01)
*A61K 31/4439* (2006.01)
*A61K 31/7056* (2006.01)
*C12Q 1/68* (2006.01)
*G01N 1/30* (2006.01)
*G01N 33/68* (2006.01)

(52) U.S. Cl.
CPC ............ *C07D 277/66* (2013.01); *A61K 31/13* (2013.01); *A61K 31/428* (2013.01); *A61K 31/4439* (2013.01); *A61K 31/7056* (2013.01); *A61K 45/06* (2013.01); *C07D 417/04* (2013.01); *C07D 417/14* (2013.01); *C12Q 1/6806* (2013.01); *G01N 1/30* (2013.01); *G01N 33/6896* (2013.01); *C12Q 2563/173* (2013.01); *G01N 2001/302* (2013.01)

(58) Field of Classification Search
USPC ....................................................... 548/156
See application file for complete search history.

(56) References Cited

U.S. PATENT DOCUMENTS 7,713,962 B2    5/2010    Wischik et al. ........... 514/224.8
2009/0123373 A1*  5/2009    Wang ................... C07D 277/66
                                          424/1.89

FOREIGN PATENT DOCUMENTS

WO    WO 2010/066357 A1    6/2010
WO    WO 2011/002635 A1    1/2011

OTHER PUBLICATIONS

Chemical Abstracts Registry No. 65402-15-5 in Seitz, CA 88:75299, 1978.*
PubChem CID 50930730—National Center for Biotechnology Information. PubChem Compound Database; CID=50930730, http://pubchem.ncbi.nlm.nih.gov/summary/summary.cgi?cid=50930730 (accessed Aug. 19, 2015), create date Mar. 24, 2011.*
PubChem CID 49849298—National Center for Biotechnology Information. PubChem Compound Database; CID=49849298, http://pubchem.ncbi.nlm.nih.gov/summary/summary.cgi?cid=49849298 (accessed Aug. 19, 2015), create date Jan. 31, 2011.*
PubChem CID 46897855—National Center for Biotechnology Information. PubChem Compound Database; CID=46897855, http://pubchem.ncbi.nlm.nih.gov/summary/summary.cgi?cid=46897855 (accessed Aug. 19, 2015), create date Sep. 28, 2010.*
PubChem CID 46839370—National Center for Biotechnology Information. PubChem Compound Database; CID=46839370, http://pubchem.ncbi.nlm.nih.gov/summary/summary.cgi?cid=46839370 (accessed Aug. 19, 2015), create date Aug. 10, 2010.*
Horobin, CA 76:31978, 1972.*
National Center for Biotechnology Information. PubChem Substance Database; SID=114279600, https://pubchem.ncbi.nlm.nih.gov/substance/114279600 (accessed Feb. 9, 2016), Deposit Date: Mar. 24, 2011.*
National Center for Biotechnology Information. PubChem Substance Database; SID=104178053, https://pubchem.ncbi.nlm.nih.gov/substance/104178053 (accessed Feb. 9, 2016), Deposit Date: Jan. 31, 2011.*
National Center for Biotechnology Information. PubChem Substance Database; SID=99350539, https://pubchem.ncbi.nlm.nih.gov/substance/99350539 (accessed Feb. 9, 2016), Deposit Date: Sep. 28, 2010.*

(Continued)

*Primary Examiner* — Laura L. Stockton
(74) *Attorney, Agent, or Firm* — Licata & Tyrrell P.C.

(57) ABSTRACT

The present invention discloses thioflavine S and primuline derivatives which inhibit hepatitis C virus helicase and protease activity. Consequently, the compounds of the present invention interfere with the life cycle of the hepatitis C virus and are useful as antiviral agents. The present invention further relates to pharmaceutical compositions containing the aforementioned compounds and methods of treating an HCV infection.

4 Claims, No Drawings

(56) References Cited

OTHER PUBLICATIONS

National Center for Biotechnology Information. PubChem Substance Database; SID=99222880, https://pubchem.ncbi.nlm.nih.gov/substance/99222880 (accessed Feb. 9, 2016), Deposit Date: Aug. 10, 2010.*

Horobin, Stain Technology, 1971, 46(6), pp. 297-304.*

Bacon et al. "Boceprevir for Previously Treated Chronic HCV Genotype 1 Infection" The New England Journal of Medicine 2011 364:1207-1217.

Frick, D. N. "The Hepatitis C Virus NS3 Protein: A Model RNA Helicase and Potential Drug Target" Current Issues in Molecular Biology 2007 9:1-20.

Hiraga et al. "Rapid Emergence of Telaprevir Resistant Hepatitis C Virus Strain from Wildtype Clone In Vivo" Hepatology 2011 54:781-788.

Kolykhalov et al. "Hepatitis C Virus-Encoded Enzymatic Activities and Conserved RNA Elements in the 3' Nontranslated Region Are Essential for Virus Replication In Vivo" Journal of Virology 2000 74(4):2046-2051.

Krawczyk et al. "Amidinoanthracyclines—a New Group of Potential Anti-Hepatitis C Virus Compounds" Biological Chemistry 2009 390:351-360.

Kwong et al. "Viral and Cellular RNA Helicases as Antiviral Targets" Nature Reviews Drug Discovery 2005 4:845-853.

Lam, A. M. I. and Frick, D. N. "Hepatitis C Virus Subgenomic Replicon Requires an Active NS3 RNA Helicase" Journal of Virology 2006 80:404-411.

Mackintosh et al. "Structural and Biological Identification of Residues on the Surface of NS3 Helicase Required for Optimal Replication of the Hepatitis C Virus" The Journal of Biological Chemistry 2006 281:3528-3535.

Manns et al. "Peginterferon Alfa-2b Plus Ribavirin Compared with Interferon Alfa-2b Plus Ribavirin for Initial Treatment of Chronic Hepatitis C: a Randomised Trial" The Lancet 2001 358:958-965.

McHutchison, J. G. "Understanding Hepatitis C" American Journal of Managed Care 2004 10:S21-S29.

Nagarajan et al. "Discovery of Novel Benzothiazolesulfonamides as Potent Inhibitors of HIV-1 Protease" Bioorganic & Medicinal Chemistry 2003 11:4769-4777.

NCBI Compound ID 44251434, create date: Nov. 9, 2009.

NCBI Compound ID 44251437, create date: Nov. 9, 2009.

NCBI Compound ID 46839370, create date: Aug. 10, 2010.

Paeshuyse, et al. "Comparative In Vitro Anti-Hepatitis C Virus Activities of a Selected Series of Polymerase, Protease, and Helicase Inhibitors" Antimicrobial Agents and Chemotherapy 2008 52(9):3433-3437.

Stankiewicz-Drogoń, et al. "Synthesis of New Acridone Derivatives, Inhibitors of NS3 Helicase, Which Efficiently and Specifically Inhibit Subgenomic HCV Replication" Journal of Medicinal Chemistry 2010 53:3117-3126.

Zeuzem et al. "Telaprevir for Retreatment of HCV Infection" The New England Journal of Medicine 2011 364:2417-2428.

International Search Report from PCT/US2012/054130, Jan. 28, 2013, PCT.

International Preliminary Report on Patentability from PCT/US2012/054130, Mar. 12, 2014, PCT.

* cited by examiner

HCV HELICASE INHIBITORS AND METHODS OF USE THEREOF

INTRODUCTION

This application is the national stage under 35 U.S.C. §371 of PCT International Application No. PCT/US2012/054130, filed Sep. 7, 2012, which claims the benefit of priority of U.S. Provisional Application Nos. 61/531,860, filed Sep. 7, 2011, the contents of which are incorporated herein by reference in their entireties.

This invention was made with government support under contract numbers U54 HG005031, RO1 AI088001 and RO3 MH085690 awarded by the National Institutes of Health. The government has certain rights in the invention.

BACKGROUND OF THE INVENTION

The hepatitis C virus (HCV) infects about 170 million people worldwide causing profound morbidity and mortality (McHutchison (2004) *Am. J. Manag. Care* 10:S21-S29). HCV is typically treated with the nucleoside analog ribavirin combined with one of several recombinant human alpha interferons. Though such treatments are effective, therapy is poorly tolerated, expensive, and not equally effective against all HCV genotypes (Manns, et al. (2001) *Lancet* 358:958-965). Better HCV treatments are therefore being modeled on other antivirals, which unlike interferon and ribavirin directly attack proteins that HCV synthesizes in human cells. Such "direct acting antivirals" (DAAs) typically are small molecules that inhibit viral enzymes, with the most common targets being viral polymerases and viral proteases. Two HCV protease inhibitors, telaprevir (Zeuzem, et al. (2011) *N. Engl. J. Med.* 364:2417-2428) and boceprevir (Bacon, et al. (2011) *N. Engl. J. Med.* 364:1207-1217), were recently approved for use in HCV patients, but neither alone eradicates HCV infection because HCV rapidly evolves to become resistant to the DAAs (Hiraga, et al. (2011) *Hepatology* doi: 10.1002/hep.24460). Protease inhibitors need to be administered with interferon and ribavirin, and as a consequence many patients still poorly tolerate the new therapies.

Telaprevir and boceprevir both inhibit the HCV nonstructural protein 3 (NS3). NS3 is one of ten proteins that are derived from the approximately 3,000 amino acid long polypeptide encoded by the HCV RNA genome. Viral and host proteases cleave the HCV polyprotein into mature structural (core, E1, E2) and non-structural proteins (p7, NS2, NS3, NS4A, NS4B, NS5A, and NS5B). The HCV nonstructural proteins form four enzymes. NS5B is a polymerase that synthesizes new viral RNA. The NS2 and NS3 proteins combine to form an autocatalytic protease. NS3 and NS4A combine to form a serine protease that cuts itself, cleaves the NS4B/NS5A, NS5A/NS5B junctions, and some cellular proteins. NS3 is also an ATP-fueled helicase that can separate and re-arrange RNA/RNA, RNA/DNA and DNA/DNA nucleic acid duplexes and displace nucleic acid bound proteins (Frick (2007) *Curr. Issues Mol. Biol.* 9:1-20).

Helicases have been widely studied as possible drug targets although progress has been slower than with other viral enzymes (Frick (2007) supra; Kwong, et al. (2005) *Nat. Rev. Drug Discov.* 4:845-853). Nevertheless, HCV needs a functional helicase to replicate in cells (Kolykhalov, et al. (2000) *J. Virol.* 74:2046-2051; Lam & Frick (2006) *J. Virol.* 80:404-4119; Mackintosh, et al. (2006) *J. Biol. Chem.* 281:3528-3535), and small molecules that inhibit HCV helicase catalyzed reactions also inhibit cellular HCV RNA replication (Paeshuyse, et al. (2008) *Antimicrob. Agents Chemother.* 52:3433-3437; Krawczyk, et al. (2009) *Biol. Chem.* 390:351-360; Stankiewicz-Drogon, et al. (2010) *J. Med. Chem.* 53:3117-3126). Therefore, NS3 helicase is a viable target for use in the treatment of HCV.

SUMMARY OF THE INVENTION

The present invention features a pharmaceutical composition containing a pharmaceutically acceptable carrier and a compound of Formula I or Formula II, or a pharmaceutically acceptable salt, ester or prodrug thereof, Formula I

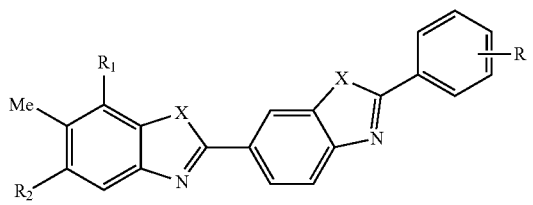

Formula II

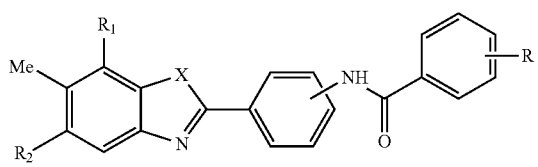

wherein one of $R_1$ or $R_2$ is $SO_3H$, $CO_2H$ or a carboxylic acid isostere and the other of $R_1$ or $R_2$ is H; each X is independently O, S, $NR_3$, or C=C; R is an amino, nitro, or substituted or unsubstituted benzothiazole, benzamide, phenylurea, benzenesulfonamide, pyridine-carboxamide, naphthalene-carboxamide, or benzothiazole-carboxamide group; and $R_3$ is hydrogen, alkyl, alkenyl, cycloalkyl, aryl, heteroaryl, or heterocycloalkyl. In some embodiments the pharmaceutical composition further includes another anti-HCV agent selected from interferon, ribavirin, amantadine, another HCV protease inhibitor, an HCV polymerase inhibitor, an HCV helicase inhibitor, or an internal ribosome entry site inhibitor. Methods for inhibiting HCV NS3 helicase and protease activity, inhibiting HCV replication, treating an HCV infection, staining viable cells in situ, detecting amyloid beta protein plaques in a biopsy sample (e.g., in the diagnosis of Alzheimer's disease or a related disorder) and staining or quantifying DNA in a sample with a compound of Formula I or Formula II are also provided.

DETAILED DESCRIPTION OF THE INVENTION

A new class of compounds that inhibit the NS3 helicase and act against the HCV or DV replicon has now been identified. The compounds described herein were identified using a molecular beacon-based helicase assay and are functionally unique compared to other reported HCV helicase inhibitors because they are also capable of inhibiting NS3 protease activity. The helicase inhibitors described herein were isolated from the dyes thioflavine S (direct yellow 7) and primuline (direct yellow 59). Thioflavine S is made from primuline and specifically stains neurofibrillary tangles and senile plaques (Guntern, et al. (1992) *Experientia* 48:8-10). Both dyes are mixtures of compounds containing the benzothiazole ring system, a scaffold that has also been used to design DNA minor-groove binding dyes (Karlsson, et al. (2003) *Nucleic Acids Res.* 31:6227-6234; Karlsson, et al. (2004) *Bioorg. Med. Chem.* 12:2369-2384), microsomal triglyceride transfer protein (MTP) inhibitors (Vu, et al. (2009) *Bioorg. Med. Chem. Lett.* 19:1416-1420), and HIV protease inhibitors (Nagarajan, et al. (2003) *Bioorg. Med. Chem.* 11:4769-4777).

Accordingly, the present invention features compounds of Formula I and Formula II:

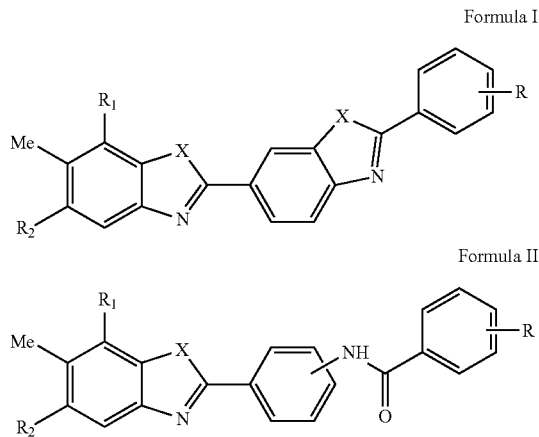

Formula I

Formula II or a pharmaceutically acceptable salt, ester or prodrug thereof, wherein one of $R_1$ or $R_2$ is $SO_3H$, $CO_2H$ or a carboxylic acid isostere and the other of $R_1$ or $R_2$ is H;

each X is independently O, S, $NR_3$, or C=C;

R is an amino ($—NH_2$), nitro ($—NO_2$), or substituted or unsubstituted benzothiazole, benzamide, phenylurea, benzenesulfonamide, pyridine-carboxamide, naphthalene-carboxamide, or benzothiazole-carboxamide group; and $R_3$ is hydrogen, alkyl, alkenyl, cycloalkyl, aryl, heteroaryl, or heterocycloalkyl.

As used herein a "carboxylic acid isostere" is intended to include tetrazole, hydroxamic acid, acylcyanamide, sulfonamide, sulfonamide, phosphonate, sulfonate, cyclopentane-1,3-dione, 3-hydroxycyclobutene-1,2-dione, hydroxyisoxazole and oxadiazolone.

The term "substituted" as used herein, refers to independent replacement of one, two, or three or more of the hydrogen atoms thereon with substituents including, but not limited to, —F, —Cl, —Br, —I, —OH, —$NO_2$, —CN, —$CF_3$, —$NH_2$, —NH-alkyl, —NH-alkenyl, —NH-cycloalkyl, —NH-aryl, —NH-heteroaryl, —NH-heterocycloalkyl, -dialkylamino, diarylamino, -diheteroarylamino, —O-alkyl, —O-alkenyl, —O-cycloalkyl, —O-aryl, —O-heteroaryl, —O-heterocycloalkyl, —C(O)-alkyl, —C(O)-alkenyl, —C(O)-cycloalkyl, —C(O)-aryl, —C(O)-heteroaryl, —C(O)-heterocycloalkyl, —$CONH_2$, —CONH-alkyl, —CONH-alkenyl, —CONH-cycloalkyl, —CONH-aryl, —CONH-heteroaryl, —CONH-heterocycloalkyl, —$OCO_2$-alkyl, —$OCO_2$-alkenyl, —$OCO_2$-cycloalkyl, —$OCO_2$-aryl, —$OCO_2$-heteroaryl, —$OCO_2$-heterocycloalkyl, —$OCONH_2$, —OCONH-alkyl, —OCONH-alkenyl, —OCONH-cycloalkyl, —OCONH-aryl, —OCONH-heteroaryl, —OCONH-heterocycloalkyl, —NHC(O)-alkyl, —NHC(O)-alkenyl, —NHC(O)-cycloalkyl, —NHC(O)-aryl, —NHC(O)-heteroaryl, —NHC(O)-heterocycloalkyl, —$NHCO_2$-alkyl, —$NHCO_2$-alkenyl, —$NHCO_2$-cycloalkyl, —$NHCO_2$-aryl, —$NHCO_2$-heteroaryl, —$NHCO_2$-heterocycloalkyl, —NHC(O)$NH_2$, —NHC(O)NH-alkyl, —NHC(O)NH-alkenyl, —NHC(O)NH-cycloalkyl, —NHC(O)NH-aryl, —NHC(O)NH-heteroaryl, —NHC(O)NH-heterocycloalkyl, —NHC(S)$NH_2$, —NHC(S)NH-alkyl, —NHC(S)NH-alkenyl, —NHC(S)NH-cycloalkyl, —NHC(S)NH-aryl, —NHC(S)NH-heteroaryl, —NHC(S)NH-heterocycloalkyl, —NHC(NH)$NH_2$, —NHC(NH)NH-alkyl, —NHC(NH)NH-alkenyl, —NHC(NH)NH-cycloalkyl, —NHC(NH)NH-aryl, —NHC(NH)NH-heteroaryl, —NHC(NH)NH-heterocycloalkyl, —NHCNH)-alkyl, —NHC(NH)-alkenyl, —NHC(NH)-cycloalkyl, —NHC(NH)-aryl, —NHC(NH)-heteroaryl, —NHC(NH)-heterocycloalkyl, —C(NH)NH-alkyl, —C(NH)NH-alkenyl, —C(NH)NH-cycloalkyl, —C(NH)NH-aryl, —C(NH)NH-heteroaryl, —C(NH)NH-heterocycloalkyl, —S(O)-alkyl, —S(O)-alkenyl, —S(O)-cycloalkyl, —S(O)-aryl, —S(O)-heteroaryl, —S(O)-heterocycloalkyl —$SO_2NH_2$, —$SO_2NH$-alkyl, —$SO_2NH$-alkenyl, —$SO_2NH$-alkenyl, —$SO_2NH$-cycloalkyl, —$SO_2NH$-aryl, —$SO_2NH$-heteroaryl, —$SO_2NH$-heterocycloalkyl, —$NHSO_2$-alkyl, —$NHSO_2$-alkenyl, —$NHSO_2$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, heterocycloalkyl, -cycloalkyl, polyalkoxyalkyl, polyalkoxy, -methoxymethoxy, -methoxyethoxy, —SH, —S-alkyl, —S-alkenyl, —S-cycloalkyl, —S-aryl, —S-heteroaryl, —S-heterocycloalkyl, or methylthiomethyl. It is understood that the aryls, heteroaryls, alkyls, and the like can be further substituted. In some cases, each substituent in a substituted moiety is additionally optionally substituted with one or more groups, each group being independently selected from —F, —Cl, —Br, —I, —OH, —$NO_2$, —CN, —$CF_3$, or —$NH_2$.

As used herein, the term "alkyl" refers to a nonaromatic monovalent group with a saturated carbon atom as the point of attachment. An alkyl of this invention contains between 1 and 12 carbons (i.e., $C_1$ to $C_{12}$) and may be a linear or branched structure. Similarly, cycloalkyls refer to cyclic alkyls with between 3 and 12 carbon atoms (i.e., $C_3$ to $C_{12}$). The term "alkenyl" refers to a monovalent group with a nonaromatic carbon atom as the point of attachment and having at least one nonaromatic carbon-carbon double bond. An alkenyl of this invention contains between 2 and 12 carbons (i.e., $O_2$ to $O_{12}$) and may be a linear or branched structure.

As demonstrated herein, when R is a substituted or unsubstituted benzamide, phenylurea, benzenesulfonamide, pyridine-carboxamide, naphthalene-carboxamide, or benzothiazole-carboxamide group, said group is attached to the parent compound via an amide linkage.

In accordance with the invention, any of the aryls, substituted aryls, heteroaryls and substituted heteroaryls described herein, can be any aromatic group. Aromatic groups can be substituted or unsubstituted.

Compounds within the scope of Formula I, can be prepared as described herein or by conventional synthetic approaches known to those skilled in the art. Representative compounds of the invention include, but are not limited to, compounds described in the Examples. In particular embodiments, the compound of the invention is not a compound isolated from thioflavine S and primuline dye mixtures. In this respect, the compound of the invention is not T1, T2, P1, P1a, P2, P2a, P3, or P4.

Compounds of the invention can be used as is or prepared as pharmaceutically acceptable salts. As used herein, the term "pharmaceutically acceptable salt" refers to those salts of the compounds of Formula I which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. See, e.g., Berge, et al. (1977) *J. Pharmaceutical Sciences* 66:1-19. Salts can be prepared in situ during the final isolation and purification of the compounds of the invention, or separately by reacting a free base with a suitable organic acid. Examples of pharmaceutically acceptable salts include, but are not limited to, nontoxic acid addition salts formed from amino group and an inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds of Formula I, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds of Formula I which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug," as used herein means a compound which is convertible in vivo by metabolic means (e.g., by hydrolysis) to afford any compound delineated by the formula of the instant invention. Various forms of prodrugs are known in the art, for example, as discussed in Bundgaard (ed.) *Design of Prodrugs*, Elsevier (1985); Widder, et al. (ed.) *Methods in Enzymology*, vol. 4, Academic Press (1985); Krogsgaard-Larsen, et al. (ed.) *Design and Application of Prodrugs, Textbook of Drug Design and Development*, Chapter 5, 113-191 (1991); Bundgaard, et al. (1992) *J. Drug Deliv. Rev.* 8:1-38; Bundgaard (1988) *J. Pharmaceut. Sci.* 77:285; Higuchi & Stella (eds.) *Prodrugs as Novel Drug Delivery Systems*, American Chemical Society (1975).

Compounds of the present invention are of particular use in the prevention and treatment of HCV or DV. In this respect, the one or more compounds of the invention can be formulated as a pharmaceutical composition. A pharmaceutical composition contains a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

An inhibitory amount or dose of the compounds of the present invention may range from about 0.1 mg/kg to about 500 mg/kg, alternatively from about 1 to about 50 mg/kg. Inhibitory amounts or doses will also vary depending on route of administration, as well as the possibility of co-usage with other agents.

According to the methods of treatment of the present invention, viral infections are treated or prevented in a subject, such as a human or lower mammal, by administering to the subject an effective amount or an inhibitory amount of a compound of the present invention, in such amounts and for such time as is necessary to achieve the desired result. The term "effective amount" of a compound of the invention, as used herein, means a sufficient amount of the compound so as to decrease the viral load in a subject and/or decrease the subject's HCV symptoms. As is well understood in the medical arts an effective amount of a compound of this invention will be at a reasonable benefit/risk ratio applicable to any medical treatment.

It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In addition to the instant compound, treatment can include the use of another anti-viral agent such as interferon, ribavirin, amantadine, another viral protease inhibitor (e.g., HCV or DV protease inhibitor), a viral polymerase inhibitor (e.g., HCV or DV polymerase inhibitor), a HCV or DV helicase inhibitor, or an internal ribosome entry site inhibitor.

Additional methods of the present invention include the treatment of biological samples, HCV NS3 protein or DV NS3 protein with an inhibitory amount of a compound of the present invention in such amounts and for such time as is necessary to inhibit viral replication and/or reduce viral load, or inhibit NS3 helicase activity and/or NS3 protease activity. The term "inhibitory amount" means a sufficient amount to inhibit helicase activity, protease activity, viral replication and/or decrease the hepatitis C or Dengue viral load in a biological sample or inhibit helicase activity and/or protease activity of NS3. The term "biological sample(s)" as used herein means a substance of biological origin intended for administration to a subject. Examples of biological samples include, but are not limited to blood and components thereof such as plasma, platelets, subpopulations of blood cells and the like; organs such as kidney, liver, heart, lung, and the like; sperm and ova; bone marrow and components thereof, or stem cells. Thus, another embodiment of the present invention is a method of treating a biological sample by contacting said biological sample with an inhibitory amount of a compound or pharmaceutical composition of the present invention. In some embodiments, the biological sample is, or is suspected of being, contaminated with HCV or DV.

Given that the instant compounds retain their function as dyes, the present invention also features methods of using said compounds to stain viable cells in situ, detect amyloid beta protein plaques in a biopsy sample (e.g., in the diagnosis of Alzheimer's disease or a related disorder) and stain or quantify DNA in a sample.

The invention is described in greater detail by the following non-limiting examples.

Example 1

Experimental Procedures

Materials.

Thioflavine S and primuline were purchased from Sigma and MP Biomedicals, respectively. The Mechanistic Diversity Library was obtained from the National Cancer Institute. All other reagents were purchased from commercial suppliers and used as received. Methylene chloride, acetonitrile, toluene, ethyl ether and THF were dried by being passed through two packed columns of anhydrous, neutral alumina prior to use. HPLC/MS analysis was carried out with gradient elution (5% $CH_3CN$ to 100% $CH_3CN$) on an AGILENT 1200 RRLC with a photodiode array UV detector and an AGILENT 6224 TOF mass spectrometer. Compound purity was determined using RP HPLC and was measured on the basis of peak integration (area under the curve) from UV/vis absorbance (at 214 nm), and compound identity was determined on the basis of exact mass analysis. All compounds used for biological studies have purity >95% except for the following compounds: P3 (89.2%), P4 batch 2 (85.6%), 6 (90.0%), 11 (89.1%), 14 (80.4%), 17 (93.6%), 28 (93.2%), 32 (94.4%), and 36 (88.6%).

All oligonucleotides were purchased from Integrated DNA Technologies (IDT, Coralville, Iowa). The partially duplex DNA substrates used in MBHAs consisted of a helicase substrate forming 25 base pairs and consists of a 45-mer bottom strand 5'-<u>GCTCCCCGT</u> TCA TCG ATT <u>GGGGAGC</u>(T)$_{20}$-3' (SEQ ID NO:1) and the 25-mer HCV top strand 5'-Cy5-GCT CCC CAA TCG ATG AAC <u>GGGGAGC</u>-IBRQ-3' (SEQ ID NO:2). The 19 base pair RNA substrate used in MBHAs was composed of a 39 nucleotide long bottom strand 5'-AGU GCC UUG ACG AUA CAG C(U)$_{20}$-3' (SEQ ID NO:3) and the 24 nucleotide long top strand 5'-Tye$^{665}$-<u>AGUGCG</u> CUG UAU CGU CAA <u>GGCACU</u>-IBRQSp-3' (SEQ ID NO:4). Underlined areas denote hairpin-forming regions. DNA and RNA substrates were annealed and purified as described previously (Belon & Frick (2008) *BioTechniques* 45:433-40, 442).

The cloning, expression, and purification of His-tagged recombinant HCV NS3 protein have been described previously (Lam, et al. (20030 *J. Virol.* 77:3950-61; Heck, et al. (2008) *Antimicrob. Agents Chemother.* 52:1901-11; Frick et al. (2010) *Methods Mol. Biol.* 587:223-233; Belon, et al. & Frick (2009) *J. Mol. Biol.* 388:851-864).

Helicase Assays.

All molecular beacon-based helicase assays (MBHAs) were performed according to known methods (Belon & Frick (2008) supra; Belon & Frick (2009) supra). For screening the NCI library, MBHAs contained 25 mM MOPS pH 6.5, 1.25 mM MgCl$_2$, 5.0 nM MBHA substrate, 12.5 nM NS3h_1b(con1), 5 µg/mL BSA, 0.01% (v/v) TWEEN 20, 0.05 mM DTT with 20 µM each test compound (2% v/v final DMSO). In each flat, black 384-well plate, 56 compounds were tested, in triplicate, along with three negative controls (DMSO only), three positive controls (500 nM dT$_{20}$), and two wells with no enzyme. Fluorescence was read before ATP ($F_0$) addition and 30 minutes after ATP was added to 1 mM ($F_{30}$) using a Tecan Infinite M200 fluorescence microplate reader with excitation and emission wavelengths set to 643 and 670 nm, respectively. Percent inhibition was calculated with equation 1, and compound interference in the MBHA was calculated with equation 2.

$$\text{Inhibition (\%)} = \frac{\frac{Fc_0}{Fc_{30}} - \frac{F(-)_0}{F(-)_{30}}}{1 - \frac{F(-)_0}{F(-)_{30}}} \times 100 \quad \text{(Equation 1)}$$

$$\text{Interference (ratio)} = 1 - \frac{Fc_0}{F(-)_0} \quad \text{(Equation 2)}$$

In Equations 1 and 2, $Fc_0$ is the fluorescence of the reactions containing the test compound before adding ATP, $Fc_{30}$ is the fluorescence of the test compound reaction 30 minutes after adding ATP. $F(-)_0$ is the average of three DMSO-only negative control reactions before adding ATP and $F(-)_{30}$ is the average of three DMSO-only reactions 30 minutes after adding ATP.

To monitor helicase reaction kinetics and to calculate IC$_{50}$ values, MBHAs were performed in 60 µL in white ½ area 96-well plates and measured in a Thermo Varioscan Multimode reader (Thermo Scientific) using the 643 nm excitation wavelength and 667 emission wavelengths. Reactions were again performed by first incubating all components except for ATP for two minutes, then initiated by injecting in 1/10 volume of ATP such that the final concentration of all components was as noted above. Conditions were as described above except that 5% v/v DMSO was present in each assay. Initial reaction velocities were calculated by fitting first-order decay equation to data obtained after ATP addition and calculating an initial velocity form the resulting amplitude and rate constant. The concentration at which a compound caused a 50% reduction in reaction velocity (IC$_{50}$) was calculated by fitting compound concentration to initial velocity using equation 3:

$$v_i = \frac{v_0}{1 + \left(\frac{[I]}{IC_{50}}\right)^h} \quad \text{(Equation 3)}$$

where, $v_0$ is the velocity observed in DMSO-only controls inhibition, h is the Hillslope coefficient, [I] is the concentration of test compound.

DNA Binding Assays.

Fluorescent intercalation displacement (FID) assays (Boger, et al. (2001) *J. Am. Chem. Soc.* 123:5878-5891) were used to measure the ability of a compound to bind the MBHA substrate. The concentration at which half the ethidium bromide is displaced (EC$_{50}$) was determined using the different conditions as above to more closely mimic the conditions of a standard helicase assay. Each 100 µL reaction contained 25 mM MOPS pH 6.5, 0.16 µM MBHA DNA substrate (lacking Cy5 and IBQ-RQ modifications), 2 µM ethidium bromide, and various concentrations of test compound. Fluorescence of ethidium bromide was monitored using excitation and emission wavelengths of 545 and 595 nm, respectively, on a Cary Eclipse fluorescence spectrophotometer in white 96-well plates. The amount of ethidium bromide-DNA complex fluorescence was used to estimate the ability of compounds to bind DNA, and therefore displace the fluorescent intercalator (ethidium bromide).

$$\text{Binding(\%)} = \left(1 - \frac{Fc - F(+)}{F(-) - F(+)}\right) \times 100 \quad \text{(Equation 4)}$$

In Equation 4, Fc is the fluorescence in the presence of the compound, F(−) is the average DMSO-only negative controls, and F(+) is the average positive controls (100 µM berenil). EC$_{50}$ values were from a normalized dose-response curve.

A modified FID assay, in which ethidium bromide was replaced with SYBR Green I (Invitrogen), was used to estimate a compounds affinity for the MBHA substrate. Reactions were performed as described above except that the DNA substrate was present at 0.32 µM, ethidium bromide was absent, and SYBER Green was present at (0.68 µM). Data were normalized as described above and fit to concentration-response equation using GraphPad Prism software. Titrations with each compound were performed in triplicate, and EC$_{50}$ values from three independent titrations are reported ±standard deviations. Average percent bound at 100 µM is reported for compounds that did not decrease the fluorescence of SYBR Green-stained DNA more than 50% at the highest concentration tested.

ATP Hydrolysis Assays.

A modified "malachite green" assay (Lanzetta, et al. (1979) *Anal. Biochem.* 100:95-97) was used to measure ATP hydrolysis. Fifty µL reactions contained 25 mM MOPS pH 6.5, 5 mM MgCl$_2$, 2 mM ATP, 5 µg/mL BSA, 0.01% (v/v) TWEEN 20, 0.05 mM DTT, and poly(U) RNA (Saint Louis, Mo.) as indicated. Reactions were initiated by adding NS3h_1b(con1). Reactions were incubated for 15 minutes at 37° C. then stopped by mixing 40 µL of the reaction into 200 µL of the malachite green reagent (3 volumes 0.045% (w/v) malachite green, 1 volume 4.2% ammonium molybdate in 4N HCl, 0.05 volume of 20% TWEEN 20). Twenty-five µL of 34% sodium citrate was quickly added to each reaction and color allowed to develop for 15 minutes. Absorbance at 630 nm was proportional to the concentration of phosphate produced; free phosphate produced was measured against a standard curve.

HCV Subgenomic Replicon Assay.

An HCV *Renilla* luciferase reporter construct (HCV RLuc; Huang, et al. (2006) *Hepatology* 43:81-90) was used to measure the effect of each compound on cellular HCV RNA levels. In HCV RLuc, the HCV internal ribosome entry site (IRES) drives the translation of the neomycin and *Renilla* luciferase genes while the HCV nonstructural proteins (NS3 to NS5B) are translated from the Encephalomyocarditis virus IRES (Huang, et al. (2006) supra). The plasmid DNA was cleaved with ScaI, purified by phenol/chloroform extraction followed by ethanol precipitation, and used as template for RNA transcription using MEGASCRIPT T7 RNA transcription kit (Ambion, Austin, Tex.). The RNA transcripts were treated with 2 U DNase I (Ambion) at 37° C. for 30 minutes, purified by acid phenol/chloroform extraction, followed by isopropanol precipitation, and suspended in diethylpyrocarbonate-treated water. RNA concentration was determined by spectrophotometry by measuring the $A_{260}$. RNA integrity and size was checked on 1% agarose gel. Transcribed RNA was stored in aliquots at −80° C. until needed.

Huh-7.5 cells were transfected with HCV RNA by electroporation. Briefly, subconfluent Huh7.5 cells were trypsinized, suspended in complete growth medium, and centrifuged at 1,000×g for 5 minutes at 4° C. The cell pellets were then washed twice with ice-cold phosphate-buffered saline (PBS) and suspended at $1.75 \times 10^7$ cells/mL in ice-cold PBS. Replicon RNA (5 μg) was mixed with 0.4 mL of cell suspension and transferred to 2 mm gap width electroporation cuvette (EPPENDORF AG, Germany) and pulsed 5 times for 99 μsec at 820 V over 1.1 sec intervals using the ECM 830 electroporator instrument (BTX Harvard Apparatus, Holliston, Mass.). After a 5 minute recovery period at room temperature, cells were transferred to 10 ml complete growth medium, and seeded into 10 cm diameter cell culture dishes. Twenty-four hours after transfection, the medium was replaced with fresh complete DMEM supplemented with 1 mg/ml geneticin (Invitrogen) and the medium was replaced every three to four days with fresh medium containing 1 mg/mL geneticin. Geneticin-resistant colonies were selected for a period of two weeks and expanded in the presence of 250 μg/mL geneticin.

HCV RLuc replicon cells were seeded at a density of $10 \times 10^3$ cells per well in 96-well plates and incubated for 4-5 hours to allow the cells to attach to the plate. The compounds dissolved in dimethyl sulfoxide (DMSO) were added at a final concentration of 10 μM (DMSO solvent final concentration was 0.5%) and the cells were incubated for 72 hours at 37° C. under 5% $CO_2$ atmosphere. The effects of compounds on HCV replication were then assessed by measuring the *Renilla* luciferase activity in compound-treated versus DMSO-treated cells. At the end of the incubation period, the medium was aspirated and the cells were washed with 1×PBS. The *Renilla* luciferase reporter gene assay was performed using the *Renilla* luciferase assay kit (PROMEGA, Madison, Wis.) according to the manufacturer's instructions. Briefly, the cells were lysed by addition of 50 μL of 1× *Renilla* luciferase lysis buffer followed by two cycles of freeze/thaw. The luciferase activity content of the lysate was measured with a FLUOSTAR Omega microplate reader instrument (BMG Labtech, Germany) after injecting 50 μL of luciferase substrate and reading for 5 seconds.

Cell Viability Assay.

To assess compound toxicity toward Huh-7.5 cells, cells were plated and treated as above and cell viability was assessed using the CELLTITER-GLO luminescent cell viability kit (PROMEGA) following the manufacturer's instructions. Briefly, at the end of a 72 hour incubation period, the medium was aspirated and the cells were washed with 1×PBS, then an equal volume of growth medium and CELLTITER-GLO reagent was added and the lysis was initiated by mixing on an orbital shaker. The plate was incubated at 23° C. for 30 minutes and the luciferase activity was measured for 1 second using the FLUOSTAR Omega microplate reader (BMG Labtech).

Aqueous Solubility.

Solubility analysis was performed using a direct UV kinetic solubility method in a 96-well format. All liquid dispense and transfer steps were performed with the FREEDOM EVO automated liquid handler (Tecan, US). Solubility measurements were performed in an aqueous buffer solution (PRISMA HT, pION Inc.) at pH 5.0, 6.2 and 7.4, in duplicate. Solubility measurements were also performed in 1×PBS pH 7.4, and in MOPS buffer pH 6.5. Samples were incubated at room temperature for a minimum of hours to achieve equilibrium, then filtered to remove any precipitate formed. The concentration of the compounds was measured by UV absorbance (250-498 nm) using the INFINITE M200 (Tecan, US) and compared to the spectra of the precipitation-free reference solutions. Spectroscopically pure 1-Propanol (Sigma) was used as a cosolvent to suppress precipitation in the reference solutions. The solubility of each compound was determined using pSOL Evolution Plus software v3.2 (pION Inc) and was expressed as the concentration (μg/mL) of a solute in a saturated solution. Diclofenac Na (highly soluble) and Dipyridamole (poorly to moderately soluble) were used as standards. Standards and test compound stocks were made in 100% DMSO. Assay concentration of standards was 500 μM and test compounds was 100 μM, whereas the final concentration of DMSO was 1%.

Membrane Permeability.

Permeability was assessed using the Parallel Artificial Membrane Permeability Assay (PAMPA) in a 96-well format. All liquid dispensed and transfer steps were performed with the FREEDOM EVO automated liquid handler (Tecan US). Measurements were performed in an aqueous buffer solution (PRISMA HT, pION Inc.) at pH 5.0, 6.2, and 7.4, in duplicate. A "sandwich" plate (pION Inc.) composed of a donor bottom plate and an acceptor filter plate was used. The donor wells contained the compounds in 180 μl system solution, and magnetic stir bars. The filter on the bottom of each acceptor well was coated with GIT-0 lipid (pION Inc.) and filled with 200 μl of Acceptor Sink Buffer, pH 7.4 (pION Inc.) containing a surfactant to mimic the function of serum proteins. The permeation time was 30 minutes and moderate stirring (equivalent to 40 μm Aqueous Boundary Layer thickness) was applied using the GUT-BOX (pION, Inc.). After the permeation time, the sandwich was disassembled and the amount of compound present in both the donor and acceptor wells was measured by UV absorbance (250-498 nm) using the Infinite M200 (Tecan US) and compared to spectra obtained from reference standards. Mass balance was used to determine the amount of material embedded in the membrane filter. The effective permeability, Pe, was calculated using the software PAMPA Evolution Plus, version 3.2 (pION Inc). Verapamil HCl (considered highly permeable), Metoprolol (considered moderately permeable), and Ranitidine (considered poorly permeable) were used as reference standards. Permeation time was 30 minutes. Final DMSO concentration was 0.5% and standards and test compounds were assayed at 100 μM.

Hepatic Microsome Stability.

Metabolic stability was assessed in the presence of human liver microsomes (XenoTech) and mouse liver mirosomes (XenoTech). All liquid was dispensed and transfer steps were performed with the FREEDOM EVO automated liquid handler (Tecan US). NADPH, a required cofactor for CYP450 metabolism, was provided by the NADPH Regenerating System, Solutions A (BD Biosciences) and B (BD Biosciences). Compound stock solutions were initially prepared in 100% DMSO and subsequently diluted in acetonitrile for the assay. The pH of the reactions was kept at ~7.4 with potassium phosphate buffer (BD Biosciences). The reactions were started after adding NADPH to the reaction plate containing microsomes and compounds and time 0 minutes aliquots were promptly collected and mixed with ice cold acetonitrile (spiked with internal standards) to quench the reactions. The remainder of the reaction volume was incubated at 37° C. with shaking. Additional aliquots were collected 60 minutes after the start of the reaction and promptly quenched with ice cold acetonitrile (spiked with an internal standard). Samples were centrifuged at 3000 rpm for 10 minutes. The amount of compound in the supernatant was determined by LC/MS/MS (Applied Biosystems, Sciex API4000 Q-TRAP) and the percent of parent compound remaining after 60 minutes was calculated by the following formula: % parent compound remaining=[(concentration at 60 minutes/concentration at 0 minutes)×100]. All reactions were run in triplicate, except negative controls (no NADPH) which were performed as single reactions. Results reported are the mean of each reaction triplicate, normalized to the internal standard, and expressed as a percent compound remaining after the incubation time. Standards were Verapamil-HCl and Testosterone at 20 µM and 50 µM, respectively. Final DMSO concentration was ≤0.5%, ACN final concentration was and test compounds were assayed at 1 µM.

Plasma Stability.

Stability of compounds in human plasma (BioChemed Services) and mouse plasma (BioChemed Services) were determined. All liquid was dispensed and transfer steps were performed with the FREEDOM EVO automated liquid handler (Tecan US). Plasma was allowed to thaw at room temperature prior to preparing the assay solution of plasma: 1×PBS (1:1). The assay solution was warmed up at 37° C. prior of adding the compound. Immediately after compounds were added, time 0 minute aliquots were promptly collected and mixed with cold acetonitrile (spiked with an internal standard). The remainder of the reaction volume was incubated at 37° C. with shaking. Additional aliquots were collected 180 minutes after the start of the reaction and promptly quenched with cold acetonitrile (spiked with an internal standard). Samples were centrifuged at 3000 rpm for 10 minutes. The amount of compound in the supernatant was determined by LC/MS/MS (Applied Biosystems, Sciex API4000 Q-TRAP) and the percent of parent compound remaining after 180 minutes was calculated by the following formula: % parent compound remaining=[(concentration at 180 minutes/concentration at 0 minutes)×100]. Results reported are the mean of each reaction duplicate, normalized to the internal standard, and expressed as a percent of compound remaining after the incubation time. Procaine (highly unstable in human plasma) and Procainamide (highly stable in human plasma) were used as standards. Final DMSO concentration was 2.5% and standards and test compounds were assayed at 1 µM.

Plasma Protein Binding.

TEFLON Base Plate wells were rinsed with 20% ethanol for 10 minutes. Ethanol was then removed and wells were rinsed with ultrapure water and allowed to dry. RED (rapid equilibrium dialysis) inserts from Thermo Scientific (Pierce) were placed (open end up) into the wells of the base plate. All liquid was dispensed and transfer steps were performed with the FREEDOM EVO automated liquid handler (Tecan US). The sample chambers (red ring) contained 300 µl of a mixture of plasma and compound, and the buffer chambers received 500 µl of dialysis buffer (1×PBS, pH7.4). Duplicate inserts were made for each concentration tested. The base plate was covered with sealing tape and incubated at 37° C. on an orbital shaker at 350 rpm for 4 hours. After the incubation time, equal volumes from both chambers were removed and transferred to a 96 well plate containing either plasma or buffer. To precipitate proteins and release compounds, ice cold acetonitrile (with an internal standard) was added. Samples were mixed and centrifuged at 3700 rpm for 10 minutes. The amount of compound in the supernatant was determined by LC/MS/MS (Applied Biosystems, Sciex API4000 Q-Trap). The percent of free and bound compounds were calculated with the following formula: % of bound parent compound=[(amount of compound in donor-receiver/amount of compound in donor)×100]. Results reported are the mean of each reaction duplicate, normalized to the internal standard, and expressed as a percent compound bound after the incubation time. Propranolol (highly bound) and Metoprolol (poorly bound) were used as standards. Final DMSO concentration was 1% and standards and test compounds were assayed at 1 µM and 10 µM.

Hepatic Cytotoxicity.

Immortalized human hepatocytes, Fa2N-4 cells (XenoTech) were seeded at ~50,000 cells/well, and incubated with a range of concentrations (0.01-50 µM) of compound 17, in duplicate, for 24 hours at 37° C., 5% $CO_2$. Cell viability was determined by cellular ATP levels using the Luminescence ATP Detection Assay System (ATPLITE 1 step, Perkin Elmer) and the Infinite M200 µlate reader (Tecan). Camptothecin (highly toxic) and Terfenadine (highly non-toxic) were used as standards. Final DMSO concentration was 0.5%.

Chemical Stability (Hydrolytic).

The stability of compounds in 1×PBS, pH 7.4, and at room temperature, was determined. Stability was also assessed in the presence of 50% ACN. Compounds were diluted and time 0 hour aliquots were collected and transferred to acetonitrile (spiked with an internal standard). The remainder of the volume was incubated for 48 hours, with additional aliquots collected at different time points (6 total). The amount of compound was determined by LC/MS/MS. The parent compound remaining was calculated by the following formula: % parent compound remaining=[(concentration at x hour/concentration at 0 hour)×100]. Results are the mean of each reaction triplicate, normalized to the internal standard, and expressed as a percent compound remaining after 48 hours. Procaine (highly stable) was used as a control. Final DMSO concentration was 0.09% and test compounds were assayed at the solubility limit.

Example 2

Screen for HCV Helicase Inhibitors

To identify HCV helicase inhibitors, the MBHA was first used to screen the National Cancer Institute Developmental Therapeutics Program's mechanistic set library. In total, 827 compounds (at 20 µM) were screened using a MBHA with a DNA substrate (Table 1). Compounds were ranked by their ability to inhibit HCV helicase-catalyzed DNA unwinding as calculated from Equation 1.

TABLE 1

| NSC# | Inh. (%) | Int.* (Ratio) | NSC# | Inh. (%) | Int.* (Ratio) | NSC# | Inh. (%) | Int.* (Ratio) |
|---|---|---|---|---|---|---|---|---|
| 363998 | 138.7 | 0.17 | 658494 | 6.7 | 0.95 | 640638 | −7.0 | 0.93 |
| 175493 | 136.8 | 0.57 | 267033 | 6.7 | 1.04 | 56737 | −7.2 | 1.12 |
| 273829 | 105.0 | 0.26 | 293015 | 6.7 | 0.96 | 635833 | −7.3 | 0.93 |
| 34391 | 100.6 | 0.24 | 310618 | 6.6 | 1.17 | 376791 | −7.3 | 1.08 |
| 69187 | 99.2 | 0.22 | 111119 | 6.3 | 1.16 | 631152 | −7.3 | 0.94 |
| 34931 | 89.2 | 0.90 | 659999 | 6.1 | 0.44 | 682769 | −7.3 | 0.96 |
| 70845 | 84.4 | 0.59 | 146604 | 6.1 | 1.12 | 34757 | −7.4 | 0.98 |
| 154890 | 79.4 | 0.29 | 174176 | 6.0 | 1.04 | 624953 | −7.5 | 0.90 |
| 640199 | 76.4 | 0.70 | 629738 | 5.9 | 0.97 | 674495 | −7.5 | 0.98 |
| 640506 | 71.1 | 0.91 | 116535 | 5.9 | 0.93 | 98447 | −7.6 | 1.05 |
| 337766 | 70.0 | 0.65 | 4728 | 5.9 | 1.07 | 163443 | −7.6 | 0.88 |
| 85561 | 68.8 | 0.90 | 635326 | 5.9 | 1.11 | 601101 | −7.8 | 0.97 |
| 71948 | 67.5 | 0.91 | 282880 | 5.8 | 0.85 | 658709 | −7.9 | 0.90 |
| 3053 | 67.5 | 0.55 | 657799 | 5.8 | 0.98 | 683792 | −8.0 | 0.93 |
| 627168 | 64.3 | 0.53 | 521777 | 5.8 | 0.90 | 4857 | −8.0 | 1.07 |
| 44690 | 61.5 | 0.66 | 3905 | 5.7 | 0.92 | 611750 | −8.1 | 0.94 |
| 166454 | 60.4 | 0.18 | 10447 | 5.6 | 1.06 | 51812 | −8.1 | 0.99 |
| 10010 | 56.7 | 0.23 | 253272 | 5.5 | 0.97 | 624161 | −8.2 | 1.03 |
| 208734 | 56.5 | 0.56 | 7521 | 5.5 | 0.94 | 636084 | −8.2 | 1.01 |
| 638352 | 56.2 | 0.89 | 204985 | 5.4 | 1.05 | 186 | −8.3 | 1.16 |
| 87206 | 55.6 | 0.92 | 292663 | 5.1 | 0.95 | 740 | −8.3 | 1.11 |
| 526417 | 55.2 | 0.86 | 373853 | 5.1 | 0.92 | 302979 | −8.3 | 0.89 |
| 14229 | 55.1 | 1.08 | 635321 | 5.1 | 1.01 | 257473 | −8.4 | 1.08 |
| 58514 | 54.9 | 1.04 | 631583 | 5.1 | 0.98 | 99016 | −8.6 | 1.10 |
| 622124 | 54.2 | 1.11 | 311153 | 5.0 | 0.29 | 69852 | −8.6 | 1.06 |
| 51148 | 53.4 | 0.94 | 622190 | 4.9 | 1.09 | 603108 | −8.6 | 1.03 |
| 15200 | 53.4 | 0.75 | 170984 | 4.7 | 0.95 | 623059 | −8.7 | 0.94 |
| 142982 | 53.1 | 0.75 | 78365 | 4.7 | 0.98 | 263500 | −8.7 | 1.18 |
| 136044 | 47.9 | 0.33 | 175296 | 4.7 | 0.90 | 343513 | −8.7 | 0.91 |
| 258812 | 46.4 | 0.64 | 635140 | 4.6 | 1.04 | 36693 | −8.8 | 0.76 |
| 338259 | 45.5 | 0.93 | 39202 | 4.5 | 0.91 | 218439 | −8.9 | 0.46 |
| 699479 | 45.1 | 0.38 | 12825 | 4.4 | 0.95 | 148958 | −8.9 | 0.99 |
| 276299 | 42.1 | 0.54 | 636132 | 4.4 | 0.90 | 35949 | −8.9 | 1.25 |
| 219734 | 41.8 | 0.26 | 320864 | 4.4 | 0.80 | 95678 | −9.0 | 0.98 |
| 98904 | 41.2 | 0.89 | 330515 | 4.3 | 0.95 | 97338 | −9.0 | 0.96 |
| 93419 | 38.9 | 0.91 | 63446 | 4.3 | 0.76 | 62791 | −9.1 | 0.93 |
| 265450 | 38.9 | 0.54 | 634473 | 4.2 | 1.01 | 4280 | −9.2 | 1.01 |
| 96932 | 38.8 | 0.59 | 755 | 4.2 | 0.93 | 669356 | −9.2 | 1.08 |
| 5159 | 38.6 | 1.03 | 349155 | 4.1 | 0.98 | 109350 | −9.3 | 0.92 |
| 181486 | 38.3 | 0.50 | 136037 | 3.9 | 1.00 | 97703 | −9.3 | 1.11 |
| 637993 | 37.7 | 0.77 | 602617 | 3.9 | 0.97 | 169779 | −9.4 | 1.12 |
| 224124 | 37.7 | 0.93 | 1011 | 3.7 | 0.87 | 104801 | −9.5 | 1.00 |
| 245432 | 37.4 | 1.06 | 32065 | 3.7 | 1.01 | 67690 | −9.5 | 1.16 |
| 623135 | 36.6 | 0.87 | 166464 | 3.7 | 1.00 | 673622 | −9.6 | 1.08 |
| 316157 | 36.4 | 0.70 | 407335 | 3.5 | 0.88 | 643174 | −9.6 | 1.07 |
| 268986 | 36.0 | 0.81 | 622116 | 3.5 | 0.97 | 59269 | −9.7 | 0.96 |
| 24559 | 36.0 | 0.91 | 36826 | 3.4 | 0.98 | 31702 | −9.7 | 0.92 |
| 290205 | 34.9 | 1.03 | 243928 | 3.4 | 0.87 | 126771 | −9.7 | 1.12 |
| 73413 | 34.8 | 0.99 | 196524 | 3.3 | 1.02 | 65937 | −9.8 | 1.01 |
| 146397 | 34.3 | 0.67 | 319726 | 3.2 | 1.02 | 265459 | −9.8 | 1.00 |
| 70422 | 33.9 | 0.85 | 374898 | 3.2 | 0.97 | 627371 | −10.1 | 0.92 |
| 652174 | 33.4 | 0.87 | 658285 | 3.1 | 0.90 | 327697 | −10.2 | 1.22 |
| 667467 | 33.3 | 0.89 | 140911 | 3.1 | 0.99 | 349156 | −10.2 | 0.95 |
| 145366 | 33.1 | 0.53 | 249992 | 3.0 | 1.08 | 690634 | −10.3 | 0.82 |
| 329696 | 32.6 | 0.81 | 98542 | 2.9 | 0.92 | 625355 | −10.4 | 1.05 |
| 354844 | 32.6 | 0.93 | 267213 | 2.9 | 1.05 | 621486 | −10.4 | 1.16 |
| 70929 | 32.1 | 0.20 | 369317 | 2.8 | 0.95 | 689228 | −10.4 | 1.04 |
| 13973 | 31.8 | 0.28 | 750 | 2.7 | 1.07 | 640985 | −10.5 | 0.97 |
| 255109 | 31.7 | 0.77 | 634224 | 2.7 | 1.17 | 620358 | −10.5 | 0.91 |
| 267229 | 31.5 | 0.49 | 357683 | 2.7 | 0.99 | 7525 | −10.5 | 0.96 |
| 18805 | 31.0 | 0.98 | 105808 | 2.6 | 1.14 | 80396 | −10.6 | 1.12 |
| 268242 | 30.6 | 0.88 | 168597 | 2.6 | 0.98 | 664704 | −10.6 | 0.98 |
| 14574 | 30.3 | 0.85 | 191392 | 2.5 | 1.10 | 623051 | −10.9 | 0.92 |
| 85700 | 29.7 | 0.46 | 635328 | 2.5 | 0.99 | 605583 | −10.9 | 0.89 |
| 641607 | 29.4 | 1.03 | 11897 | 2.5 | 1.05 | 9706 | −10.9 | 0.76 |
| 305782 | 28.4 | 0.87 | 606532 | 2.5 | 0.99 | 637914 | −11.0 | 1.01 |
| 288010 | 28.3 | 1.01 | 253995 | 2.4 | 0.78 | 407806 | −11.1 | 1.00 |
| 305819 | 28.1 | 0.99 | 645567 | 2.4 | 1.04 | 642649 | −11.2 | 1.05 |
| 668270 | 28.1 | 0.83 | 178249 | 2.4 | 0.87 | 642048 | −11.3 | 0.99 |
| 678917 | 28.1 | 0.89 | 634471 | 2.3 | 1.06 | 145150 | −11.3 | 1.12 |
| 326231 | 28.0 | 0.94 | 155595 | 2.3 | 1.17 | 292567 | −11.3 | 0.85 |
| 18268 | 27.6 | 0.61 | 337851 | 2.3 | 0.29 | 353527 | −11.3 | 1.04 |
| 622732 | 27.4 | 0.92 | 71300 | 2.2 | 1.12 | 627708 | −11.4 | 1.03 |
| 347466 | 27.4 | 0.89 | 66300 | 2.2 | 1.21 | 329277 | −11.4 | 1.08 |
| 184403 | 27.4 | 0.42 | 620261 | 2.2 | 0.99 | 672425 | −11.4 | 0.89 |
| 28002 | 27.1 | 1.08 | 21548 | 2.1 | 0.98 | 102815 | −11.4 | 0.76 |
| 600305 | 26.6 | 0.91 | 90636 | 2.1 | 0.84 | 100856 | −11.6 | 0.98 |
| 603169 | 26.2 | 0.22 | 48151 | 2.1 | 0.98 | 687852 | −11.6 | 0.94 |

TABLE 1-continued

| NSC# | Inh. (%) | Int.* (Ratio) | NSC# | Inh. (%) | Int.* (Ratio) | NSC# | Inh. (%) | Int.* (Ratio) |
|---|---|---|---|---|---|---|---|---|
| 53908 | 26.0 | 0.82 | 371846 | 2.1 | 0.86 | 52141 | −11.6 | 0.83 |
| 22992 | 25.9 | 0.86 | 65423 | 2.0 | 1.12 | 103248 | −11.6 | 0.92 |
| 304421 | 25.6 | 0.97 | 329279 | 1.9 | 0.94 | 25149 | −11.6 | 0.93 |
| 664327 | 25.5 | 0.82 | 353648 | 1.7 | 0.94 | 625748 | −11.6 | 0.94 |
| 635366 | 25.5 | 1.05 | 406021 | 1.7 | 1.10 | 332598 | −11.7 | 0.98 |
| 351306 | 25.4 | 0.92 | 18938 | 1.7 | 1.06 | 321803 | −11.7 | 1.02 |
| 119875 | 25.1 | 0.83 | 326397 | 1.6 | 1.06 | 404241 | −11.9 | 1.06 |
| 19990 | 25.1 | 0.96 | 647889 | 1.6 | 0.89 | 79451 | −11.9 | 0.98 |
| 600300 | 24.9 | 0.91 | 175634 | 1.5 | 0.93 | 283162 | −12.0 | 1.08 |
| 54650 | 24.7 | 1.11 | 56544 | 1.5 | 0.96 | 173905 | −12.0 | 1.11 |
| 243023 | 24.2 | 0.46 | 679527 | 1.5 | 0.98 | 687330 | −12.1 | 0.91 |
| 619179 | 23.8 | 0.44 | 22842 | 1.5 | 1.10 | 173046 | −12.2 | 0.93 |
| 647613 | 23.5 | 0.91 | 642033 | 1.4 | 0.99 | 47438 | −12.2 | 1.18 |
| 633001 | 23.2 | 0.89 | 117915 | 1.4 | 1.00 | 643163 | −12.3 | 1.09 |
| 68075 | 23.1 | 1.02 | 173904 | 1.4 | 1.09 | 2979 | −12.5 | 1.00 |
| 314622 | 23.1 | 0.70 | 306864 | 1.3 | 0.86 | 616355 | −12.6 | 1.01 |
| 639828 | 23.0 | 1.05 | 630374 | 1.3 | 0.89 | 168221 | −12.6 | 0.96 |
| 382007 | 22.9 | 0.85 | 653000 | 1.2 | 0.97 | 4320 | −12.6 | 0.95 |
| 167780 | 22.8 | 1.00 | 671136 | 1.2 | 0.90 | 115538 | −12.6 | 1.02 |
| 106408 | 22.7 | 0.94 | 80756 | 1.2 | 0.97 | 24048 | −12.7 | 1.11 |
| 363182 | 22.2 | 1.08 | 286193 | 1.1 | 1.13 | 635542 | −12.7 | 0.91 |
| 215989 | 21.9 | 0.82 | 278619 | 1.1 | 1.15 | 11926 | −12.8 | 1.14 |
| 361813 | 21.8 | 1.03 | 637916 | 1.1 | 0.97 | 617989 | −12.9 | 0.96 |
| 610744 | 21.5 | 0.83 | 40212 | 1.1 | 0.95 | 643028 | −13.0 | 0.96 |
| 49660 | 21.2 | 0.93 | 302358 | 1.1 | 1.05 | 174121 | −13.1 | 0.91 |
| 637680 | 21.2 | 0.91 | 654259 | 1.1 | 0.98 | 118030 | −13.1 | 0.92 |
| 14974 | 20.9 | 0.99 | 174280 | 1.1 | 0.90 | 641233 | −13.1 | 0.91 |
| 632536 | 20.7 | 0.84 | 102811 | 1.0 | 1.08 | 90487 | −13.2 | 1.18 |
| 328166 | 20.7 | 1.04 | 604535 | 1.0 | 1.08 | 308847 | −13.3 | 1.05 |
| 299879 | 20.5 | 0.94 | 208913 | 0.9 | 1.10 | 93739 | −13.3 | 0.81 |
| 632839 | 20.4 | 0.87 | 635448 | 0.8 | 0.93 | 622640 | −13.4 | 1.10 |
| 681744 | 20.4 | 0.98 | 629301 | 0.8 | 0.91 | 32946 | −13.6 | 1.07 |
| 7364 | 20.2 | 0.86 | 678932 | 0.6 | 1.05 | 641250 | −13.6 | 0.95 |
| 68093 | 19.5 | 0.90 | 105014 | 0.4 | 0.89 | 641245 | −13.7 | 0.89 |
| 407010 | 19.4 | 0.90 | 668260 | 0.4 | 0.94 | 376265 | −13.7 | 1.02 |
| 382766 | 19.2 | 0.90 | 85236 | 0.4 | 1.20 | 26045 | −13.7 | 0.92 |
| 614928 | 19.1 | 0.99 | 176655 | 0.3 | 1.08 | 139490 | −13.8 | 0.95 |
| 30916 | 19.0 | 0.93 | 38721 | 0.3 | 0.93 | 167410 | −13.8 | 0.87 |
| 529469 | 18.9 | 0.89 | 153858 | 0.3 | 0.95 | 4644 | −13.9 | 1.32 |
| 35489 | 18.7 | 1.04 | 146268 | 0.2 | 1.15 | 135996 | −14.0 | 1.07 |
| 86100 | 18.6 | 1.00 | 268251 | 0.2 | 0.96 | 13966 | −14.1 | 1.13 |
| 339004 | 18.5 | 0.89 | 1771 | 0.2 | 0.98 | 624947 | −14.2 | 0.86 |
| 45575 | 18.4 | 0.97 | 635437 | 0.1 | 0.92 | 92510 | −14.2 | 1.00 |
| 169676 | 18.3 | 0.87 | 624206 | 0.1 | 0.81 | 165897 | −14.2 | 1.20 |
| 269754 | 18.3 | 0.98 | 107412 | 0.0 | 0.83 | 126728 | −14.3 | 1.03 |
| 670224 | 17.9 | 0.88 | 169600 | 0.0 | 0.90 | 650573 | −14.3 | 0.86 |
| 400978 | 17.9 | 1.10 | 65346 | 0.0 | 0.92 | 267461 | −14.4 | 1.01 |
| 653012 | 17.7 | 0.91 | 284356 | 0.0 | 1.10 | 697923 | −14.4 | 1.07 |
| 45388 | 17.5 | 0.95 | 643031 | −0.1 | 1.08 | 686349 | −14.4 | 0.85 |
| 296961 | 17.5 | 0.92 | 625487 | −0.1 | 1.01 | 657457 | −14.5 | 1.06 |
| 653010 | 17.5 | 0.88 | 24819 | −0.3 | 1.12 | 634926 | −14.5 | 0.92 |
| 336628 | 17.4 | 0.90 | 285116 | −0.3 | 0.90 | 104117 | −14.5 | 1.06 |
| 233872 | 17.4 | 1.00 | 256927 | −0.4 | 1.02 | 79456 | −14.5 | 0.97 |
| 644735 | 17.3 | 0.94 | 369318 | −0.4 | 0.95 | 664329 | −14.5 | 1.01 |
| 363744 | 17.2 | 1.04 | 7210 | −0.5 | 0.97 | 658139 | −14.6 | 1.06 |
| 676561 | 17.1 | 0.96 | 61805 | −0.5 | 0.95 | 293927 | −14.7 | 1.00 |
| 620277 | 17.1 | 0.93 | 616232 | −0.6 | 1.02 | 634568 | −14.8 | 0.90 |
| 11779 | 16.8 | 0.89 | 359892 | −0.7 | 0.98 | 641240 | −14.8 | 0.88 |
| 403148 | 16.8 | 0.94 | 63984 | −0.8 | 1.11 | 657598 | −14.8 | 0.94 |
| 635441 | 16.7 | 0.92 | 66914 | −0.8 | 0.91 | 622586 | −14.9 | 0.93 |
| 37364 | 16.5 | 1.01 | 328477 | −0.8 | 0.96 | 324368 | −15.0 | 0.85 |
| 274893 | 16.2 | 0.88 | 603578 | −0.8 | 0.85 | 657603 | −15.1 | 0.94 |
| 33006 | 15.9 | 0.89 | 159935 | −0.8 | 0.89 | 107415 | −15.2 | 0.97 |
| 89303 | 15.8 | 0.93 | 33004 | −0.9 | 1.00 | 623095 | −15.3 | 0.81 |
| 125066 | 15.8 | 0.79 | 226080 | −1.0 | 0.90 | 4810 | −15.4 | 1.01 |
| 634658 | 15.7 | 0.85 | 646189 | −1.0 | 0.92 | 18298 | −15.4 | 0.90 |
| 20534 | 15.7 | 0.96 | 106995 | −1.1 | 0.93 | 169774 | −15.6 | 0.92 |
| 635436 | 15.6 | 0.89 | 650792 | −1.2 | 0.86 | 3852 | −15.7 | 1.01 |
| 632841 | 15.6 | 0.81 | 76747 | −1.2 | 1.14 | 294577 | −15.9 | 0.95 |
| 24817 | 15.4 | 0.99 | 139109 | −1.2 | 1.06 | 698031 | −16.0 | 0.98 |
| 35866 | 15.3 | 0.93 | 622684 | −1.3 | 1.04 | 670225 | −16.0 | 1.04 |
| 18804 | 15.2 | 0.97 | 666526 | −1.3 | 0.97 | 67574 | −16.1 | 0.96 |
| 670140 | 15.2 | 0.95 | 328587 | −1.3 | 0.95 | 681741 | −16.2 | 0.92 |
| 626120 | 15.1 | 0.97 | 643834 | −1.3 | 0.88 | 700582 | −16.2 | 0.93 |
| 269146 | 15.0 | 0.89 | 680516 | −1.4 | 0.93 | 337612 | −16.5 | 0.97 |
| 32982 | 15.0 | 0.90 | 335142 | −1.5 | 0.95 | 625873 | −16.6 | 1.02 |
| 643164 | 14.9 | 0.86 | 1906 | −1.6 | 1.17 | 182986 | −16.6 | 1.18 |
| 145669 | 14.8 | 1.14 | 330770 | −1.6 | 0.91 | 651079 | −16.7 | 1.05 |

TABLE 1-continued

| NSC# | Inh. (%) | Int.* (Ratio) | NSC# | Inh. (%) | Int.* (Ratio) | NSC# | Inh. (%) | Int.* (Ratio) |
|---|---|---|---|---|---|---|---|---|
| 165563 | 14.6 | 0.95 | 688363 | −1.6 | 0.96 | 331757 | −16.9 | 0.93 |
| 643774 | 14.6 | 0.90 | 92339 | −1.6 | 1.04 | 26040 | −17.0 | 0.97 |
| 662825 | 14.5 | 0.93 | 676963 | −1.7 | 0.46 | 647363 | −17.1 | 0.93 |
| 664181 | 14.5 | 0.84 | 191384 | −1.8 | 1.07 | 637833 | −17.2 | 0.80 |
| 635121 | 14.5 | 0.92 | 607316 | −1.8 | 0.97 | 657298 | −17.3 | 1.01 |
| 625590 | 14.3 | 0.95 | 116693 | −1.8 | 0.92 | 36437 | −17.3 | 0.99 |
| 118732 | 14.2 | 0.89 | 682864 | −1.8 | 0.97 | 325319 | −17.4 | 0.99 |
| 605756 | 14.1 | 0.33 | 664331 | −1.8 | 1.03 | 93135 | −17.4 | 0.89 |
| 65381 | 14.1 | 0.96 | 154020 | −2.0 | 0.89 | 644794 | −17.5 | 0.96 |
| 375294 | 13.9 | 0.87 | 681730 | −2.0 | 0.88 | 648422 | −17.5 | 1.02 |
| 118976 | 13.9 | 0.96 | 56817 | −2.0 | 0.90 | 643175 | −17.5 | 0.93 |
| 330516 | 13.8 | 0.92 | 622608 | −2.1 | 1.01 | 634396 | −17.6 | 0.99 |
| 60309 | 13.6 | 0.93 | 292147 | −2.1 | 1.07 | 345647 | −17.6 | 0.80 |
| 619165 | 13.6 | 0.89 | 106997 | −2.2 | 0.96 | 615593 | −17.7 | 0.91 |
| 47147 | 13.5 | 0.40 | 643162 | −2.2 | 1.02 | 625639 | −17.7 | 1.09 |
| 635824 | 13.5 | 0.91 | 626433 | −2.2 | 0.98 | 99733 | −17.9 | 1.02 |
| 180973 | 13.5 | 0.90 | 285166 | −2.2 | 0.95 | 635312 | −18.1 | 0.93 |
| 603577 | 13.5 | 0.93 | 191389 | −2.3 | 1.06 | 677392 | −18.1 | 1.00 |
| 163088 | 13.3 | 0.87 | 292684 | −2.4 | 1.02 | 634863 | −18.2 | 0.99 |
| 695218 | 13.3 | 0.99 | 689872 | −2.4 | 1.01 | 658350 | −18.3 | 1.00 |
| 172924 | 13.3 | 1.01 | 241509 | −2.4 | 1.01 | 239375 | −18.3 | 0.90 |
| 168415 | 13.3 | 0.95 | 635975 | −2.4 | 0.97 | 626734 | −18.3 | 1.02 |
| 183359 | 13.3 | 0.83 | 679524 | −2.5 | 0.85 | 639754 | −18.3 | 1.14 |
| 149765 | 13.2 | 0.94 | 670226 | −2.6 | 1.11 | 645033 | −18.4 | 0.96 |
| 46061 | 13.2 | 0.93 | 632233 | −2.7 | 1.04 | 693053 | −18.5 | 0.93 |
| 375575 | 12.9 | 0.93 | 240419 | −2.7 | 0.94 | 174163 | −18.5 | 1.00 |
| 9856 | 12.6 | 0.84 | 24818 | −2.7 | 1.07 | 7833 | −18.7 | 1.07 |
| 71669 | 12.4 | 1.06 | 663996 | −2.7 | 1.08 | 658388 | −18.7 | 1.09 |
| 667235 | 12.3 | 1.06 | 638504 | −2.7 | 0.90 | 618332 | −18.7 | 1.03 |
| 224131 | 12.3 | 0.86 | 224117 | −2.8 | 1.01 | 11930 | −18.9 | 1.10 |
| 305222 | 12.2 | 1.03 | 61811 | −2.8 | 0.91 | 85998 | −19.0 | 1.10 |
| 621889 | 12.2 | 1.08 | 621094 | −2.8 | 0.98 | 600681 | −19.1 | 0.95 |
| 330500 | 12.0 | 1.04 | 534 | −2.8 | 1.24 | 45383 | −19.1 | 1.05 |
| 625483 | 12.0 | 0.93 | 307454 | −2.9 | 1.08 | 20514 | −19.2 | 1.06 |
| 129414 | 12.0 | 1.08 | 40666 | −2.9 | 1.09 | 643001 | −19.4 | 0.96 |
| 3970 | 11.8 | 0.95 | 328426 | −3.0 | 1.00 | 352876 | −19.4 | 1.08 |
| 749 | 11.7 | 0.89 | 640637 | −3.0 | 0.86 | 269142 | −19.6 | 1.07 |
| 697443 | 11.6 | 1.01 | 1620 | −3.0 | 1.06 | 617570 | −19.7 | 0.70 |
| 379531 | 11.6 | 0.89 | 638646 | −3.1 | 0.76 | 7530 | −19.7 | 0.98 |
| 164914 | 11.5 | 0.91 | 653558 | −3.1 | 0.98 | 236657 | −19.9 | 0.91 |
| 97911 | 11.5 | 0.95 | 128734 | −3.1 | 0.91 | 125176 | −20.2 | 0.90 |
| 376248 | 11.4 | 0.80 | 642040 | −3.2 | 0.90 | 164909 | −20.2 | 1.04 |
| 65380 | 11.3 | 1.03 | 620050 | −3.3 | 0.96 | 629713 | −20.3 | 0.90 |
| 607347 | 11.1 | 0.95 | 192965 | −3.4 | 0.89 | 643148 | −20.3 | 0.98 |
| 24113 | 11.0 | 0.81 | 7532 | −3.4 | 0.89 | 629971 | −20.4 | 0.96 |
| 265473 | 11.0 | 0.96 | 262665 | −3.4 | 0.95 | 638634 | −20.4 | 0.86 |
| 138429 | 10.9 | 1.09 | 623637 | −3.5 | 0.97 | 643351 | −20.4 | 0.89 |
| 405158 | 10.9 | 1.09 | 627666 | −3.6 | 0.87 | 268965 | −20.5 | 0.94 |
| 260610 | 10.7 | 0.27 | 646200 | −3.7 | 1.14 | 14975 | −20.8 | 1.03 |
| 323241 | 10.7 | 0.90 | 281245 | −3.7 | 1.08 | 622589 | −21.0 | 0.94 |
| 320846 | 10.7 | 0.90 | 637729 | −3.8 | 0.97 | 643186 | −21.0 | 1.04 |
| 118742 | 10.6 | 1.01 | 675593 | −3.8 | 1.04 | 623527 | −21.1 | 0.98 |
| 157389 | 10.6 | 0.88 | 313981 | −3.8 | 0.93 | 643910 | −21.3 | 1.06 |
| 640391 | 10.6 | 1.09 | 63701 | −3.8 | 0.98 | 657446 | −21.5 | 1.00 |
| 211500 | 10.6 | 0.89 | 643826 | −3.8 | 0.89 | 613009 | −21.7 | 0.94 |
| 5354 | 10.6 | 0.97 | 95580 | −3.8 | 0.93 | 635544 | −21.9 | 0.82 |
| 349438 | 10.5 | 1.01 | 18891 | −4.0 | 0.89 | 2186 | −22.0 | 1.01 |
| 76455 | 10.5 | 0.95 | 284751 | −4.0 | 1.05 | 664286 | −22.3 | 1.18 |
| 82025 | 10.4 | 0.94 | 673912 | −4.0 | 1.04 | 689857 | −22.3 | 0.87 |
| 19994 | 10.4 | 1.05 | 403883 | −4.0 | 0.93 | 65104 | −22.3 | 1.01 |
| 163501 | 10.3 | 0.91 | 54297 | −4.0 | 0.96 | 640342 | −22.4 | 0.95 |
| 71851 | 10.2 | 0.94 | 269148 | −4.1 | 0.71 | 658293 | −22.4 | 1.08 |
| 680506 | 10.2 | 0.92 | 143648 | −4.1 | 0.99 | 83265 | −22.5 | 0.98 |
| 99027 | 10.1 | 0.93 | 208914 | −4.1 | 1.09 | 631521 | −22.6 | 0.93 |
| 49842 | 9.9 | 0.98 | 623093 | −4.2 | 0.87 | 267712 | −22.8 | 1.09 |
| 633209 | 9.9 | 0.87 | 640624 | −4.2 | 1.11 | 132493 | −22.9 | 1.07 |
| 631160 | 9.9 | 0.91 | 11905 | −4.3 | 0.80 | 156215 | −23.4 | 1.02 |
| 664298 | 9.8 | 0.96 | 128305 | −4.3 | 0.99 | 5890 | −23.5 | 0.98 |
| 77021 | 9.8 | 1.00 | 634650 | −4.4 | 1.12 | 36354 | −23.7 | 1.01 |
| 169543 | 9.6 | 1.02 | 651080 | −4.4 | 0.85 | 635438 | −23.8 | 1.02 |
| 640584 | 9.6 | 0.90 | 624358 | −4.4 | 1.05 | 697468 | −23.8 | 0.97 |
| 261726 | 9.6 | 0.96 | 4960 | −4.5 | 0.90 | 267700 | −24.0 | 1.04 |
| 383468 | 9.4 | 0.98 | 662553 | −4.6 | 1.02 | 7522 | −24.0 | 0.97 |
| 140377 | 9.4 | 0.93 | 614826 | −4.8 | 1.06 | 330753 | −24.1 | 0.88 |
| 688795 | 9.3 | 1.02 | 29603 | −5.0 | 0.99 | 640335 | −24.2 | 0.91 |
| 345081 | 9.2 | 0.95 | 684845 | −5.0 | 0.91 | 647418 | −24.7 | 1.00 |
| 624158 | 9.2 | 0.90 | 175636 | −5.0 | 0.96 | 626551 | −24.9 | 0.90 |
| 177365 | 9.2 | 0.49 | 73495 | −5.1 | 1.01 | 657449 | −25.4 | 1.00 |

TABLE 1-continued

| NSC# | Inh. (%) | Int.* (Ratio) | NSC# | Inh. (%) | Int.* (Ratio) | NSC# | Inh. (%) | Int.* (Ratio) |
|---|---|---|---|---|---|---|---|---|
| 657722 | 9.1 | 0.93 | 106296 | −5.2 | 1.23 | 123115 | −25.7 | 0.96 |
| 126849 | 9.0 | 1.02 | 687849 | −5.2 | 0.93 | 640499 | −25.9 | 0.91 |
| 295156 | 9.0 | 0.99 | 118735 | −5.2 | 0.96 | 285223 | −26.2 | 1.01 |
| 635968 | 9.0 | 0.97 | 15623 | −5.2 | 1.06 | 622627 | −26.2 | 1.09 |
| 1026 | 9.0 | 0.90 | 147340 | −5.2 | 1.01 | 693632 | −26.4 | 0.98 |
| 119686 | 8.9 | 1.18 | 333856 | −5.2 | 0.95 | 185065 | −26.6 | 1.11 |
| 305884 | 8.9 | 1.04 | 129943 | −5.2 | 1.13 | 111041 | −26.9 | 0.97 |
| 265211 | 8.9 | 0.82 | 637731 | −5.3 | 1.07 | 619907 | −27.2 | 0.86 |
| 377 | 8.8 | 1.02 | 652287 | −5.4 | 0.98 | 4170 | −27.3 | 1.09 |
| 636786 | 8.8 | 0.91 | 671394 | −5.4 | 0.86 | 67580 | −27.4 | 1.12 |
| 659174 | 8.7 | 0.92 | 282752 | −5.5 | 1.00 | 294961 | −28.1 | 1.06 |
| 648419 | 8.6 | 0.90 | 76027 | −5.5 | 0.85 | 43321 | −28.3 | 1.07 |
| 72961 | 8.5 | 0.98 | 658144 | −5.5 | 0.78 | 617540 | −28.4 | 1.11 |
| 63878 | 8.3 | 0.89 | 697726 | −5.6 | 0.90 | 32992 | −28.7 | 1.04 |
| 132791 | 8.2 | 0.98 | 202000 | −5.7 | 0.99 | 33410 | −28.8 | 1.16 |
| 651084 | 8.1 | 0.95 | 603719 | −5.7 | 1.20 | 670229 | −28.8 | 1.17 |
| 41809 | 7.9 | 0.89 | 643812 | −5.7 | 0.91 | 32944 | −28.9 | 1.02 |
| 637578 | 7.9 | 0.97 | 248436 | −5.7 | 0.84 | 631529 | −28.9 | 1.06 |
| 95848 | 7.7 | 0.90 | 89671 | −5.9 | 1.04 | 687667 | −29.0 | 1.00 |
| 624169 | 7.7 | 0.96 | 90829 | −5.9 | 1.16 | 408120 | −29.4 | 1.05 |
| 757 | 7.7 | 1.00 | 266535 | −5.9 | 0.87 | 113090 | −29.5 | 1.00 |
| 154754 | 7.6 | 0.91 | 107067 | −6.0 | 0.90 | 623746 | −29.6 | 0.99 |
| 166381 | 7.6 | 0.82 | 654705 | −6.0 | 1.02 | 211489 | −30.1 | 0.82 |
| 157930 | 7.6 | 0.86 | 657456 | −6.1 | 0.85 | 636817 | −30.3 | 1.07 |
| 603624 | 7.5 | 0.92 | 74420 | −6.1 | 1.10 | 620280 | −30.3 | 1.01 |
| 79688 | 7.5 | 0.97 | 400944 | −6.2 | 0.84 | 622690 | −30.9 | 1.12 |
| 19857 | 7.4 | 1.05 | 241906 | −6.2 | 0.88 | 84074 | −31.4 | 1.11 |
| 115493 | 7.3 | 0.94 | 191393 | −6.3 | 1.05 | 634503 | −31.9 | 0.93 |
| 359463 | 7.3 | 0.45 | 618261 | −6.4 | 0.95 | 648320 | −32.6 | 1.08 |
| 4114 | 7.2 | 1.15 | 235082 | −6.4 | 1.02 | 640580 | −32.9 | 1.09 |
| 109444 | 7.2 | 1.01 | 26273 | −6.4 | 0.89 | 640974 | −33.1 | 0.87 |
| 157004 | 7.1 | 1.11 | 40341 | −6.4 | 1.09 | 641253 | −34.2 | 0.95 |
| 349644 | 7.1 | 0.91 | 622616 | −6.5 | 0.95 | 684480 | −35.3 | 1.04 |
| 352890 | 7.0 | 0.94 | 659501 | −6.6 | 1.06 | 680509 | −35.7 | 0.99 |
| 5200 | 7.0 | 1.02 | 82116 | −6.7 | 1.10 | 625641 | −37.8 | 1.20 |
| 1027 | 7.0 | 0.91 | 635306 | −6.8 | 0.96 | 184398 | −39.0 | 1.09 |
| 175274 | 7.0 | 1.09 | 176324 | −6.8 | 1.02 | 641228 | −39.7 | 0.92 |
| 338720 | 7.0 | 0.93 | 635563 | −6.8 | 0.92 | 653016 | −40.6 | 1.02 |
| 139105 | 7.0 | 0.98 | 301460 | −6.9 | 0.93 | 104129 | −42.7 | 0.92 |
| 635435 | 6.9 | 0.96 | 667251 | −7.0 | 1.09 | 264880 | −43.3 | 1.28 |
| 634928 | 6.8 | 0.97 | 80087 | −7.0 | 1.17 | 620279 | −45.1 | 1.17 |
| 185056 | 6.8 | 0.90 | 645987 | −7.0 | 0.88 | | | |

Inh., Inhibition.
Int., Interference.
*Assay interference was calculated with Equation 2.

When compound interference was plotted versus percent inhibition, it was clear that the majority of compounds in this library that would appear to inhibit HCV helicase, also interfered with the assay, with most of the interfering compounds quenching fluorescence of the MBHA substrate. Compound interference in the MBHA was evaluated by comparing the fluorescence of reactions containing each compound to the fluorescence of DMSO-only negative controls before ATP was added. Hits were therefore defined as only those compounds that did not interfere with the assays more than 20%, and twelve compounds fit these criteria.

These twelve hits were then subjected to a counterscreen designed to independently identify DNA binding compounds using a modified fluorescent intercalator displacement (FID) assay (Boger, et al. (2001) supra). The FID assay used ethidium bromide to judge a compound's ability to bind DNA and was based on the assumption that a DNA binding compound would displace a fluorescent DNA intercalating agent, leading to an observable decrease in observed fluorescence. Compounds were tested at 1.5 µM in the presence of the 25 base pair substrate used in the helicase assays. Results showed that even at a compound concentration 13-times lower than that used in the MBHA, most of the hit compounds had an ability to decrease the fluorescence of an ethidium bromide-DNA complex by more than 10%, indicative of an ability to bind DNA. The DNA minor groove-binding compound Berenil ($IC_{50}$=1.6±0.1 µM) was used a positive control in all FID assays (Boger, et al. (2001) supra).

Four compounds decreased the fluorescence of DNA-bound ethidium bromide less than 8%. The first, $CdCl_2$ is a known HCV helicase inhibitor that binds in place of the magnesium ion needed for ATP hydrolysis to fuel unwinding (Frick (2007) supra). The second, ellipticine was found to fully quench DNA-bound ethidium bromide fluorescence at higher concentrations. The $IC_{50}$ value for ellipticine in MBHAs (5.6±0.8 µM) was similar to its apparent affinity for DNA, suggesting that it inhibited the helicase by interacting with the substrate. Chromomycin A3, inhibited HCV helicase catalyzed-DNA unwinding with an $IC_{50}$ of 0.15±0.03 µM, but it had no effect on HCV helicase catalyzed RNA unwinding. This false positive could be explained by the fact that Chromomycin A3 functionally resembles ethidium bromide in that they both are fluorescent DNA binding compounds (Crissman, et al. (1976) J. Histochem. Cytochem. 24:64-71). This result also demonstrates that not all DNA binding compounds will decrease DNA-bound ethidium bromide fluorescence in an ethidium bromide-based FID assay. The final compound, thioflavine S, did not affect DNA-bound ethidium bromide fluorescence until its concentration exceeded 100 µM, where thioflavine S caused a 20% fluorescence decrease. In concentration-response experiments, thioflavine S inhibited HCV helicase-catalyzed DNA unwinding with an $IC_{50}$ of 10±1 µM, and it inhibited HCV-catalyzed RNA unwinding with an $IC_{50}$ of 12±2 µM. The related dye thioflavine T, which, like thioflavine S, is used to specifically stain Alzheimer amyloid plaques (LeVine (1999) *Methods Enzymol.* 309:274-284) had no effect on either HCV-catalyzed DNA or RNA unwinding.

Example 3

Activity of Thioflavine S Components

Thioflavine S is not a single compound but rather is a heterogeneous dye prepared from another yellow dye called primuline by successive methylation and sulfonation reactions (Conn's Biological Stains, 10th Edition). Primuline inhibited HCV helicase in MBHAs with similar potency as thioflavine S (10±4.6 µM). To better understand how these dyes inhibit HCV helicase, both mixtures were separated using preparative HPLC or combination of normal phase silica gel chromatography and reverse phase preparative HPLC.

The structure associated with the dye thioflavine S is not reported consistently or left intentionally vague, creating confusion over the chemical identity of the screening hit. For instance the MSDS (Sigma Aldrich) for thioflavine S describes the compound only as "methylated, sulfonated primuline base". In the NCI and Pubchem online databases, thioflavine S (NSC71948, SID550242) is reported as a mixture of methylated benzothiazoles having the structures:

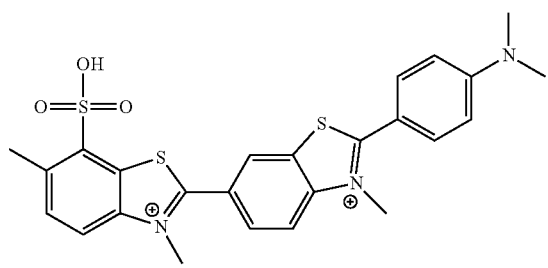

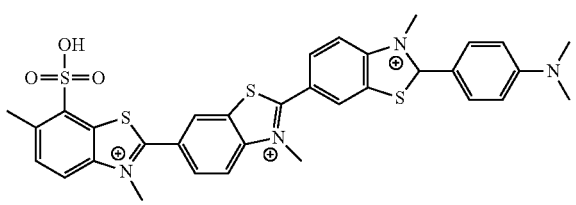

See also Sharp, et al. (2009) *J. Pharmacol. Exp. Ther.* 331:680-689; Yon, et al. (2011) *Antiviral Research* 91:233-240. Accordingly, the structure of Thioflavine S was determined using NMR and LC/MS (Frick & Belon (2010) *FASEB J.* 24:Ib202). This analysis indicated that presence of two compounds, T1 and T2.

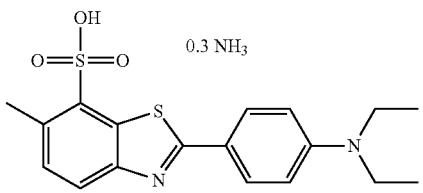

2-(4-(diethylamino)phenyl)-6-methylbenzo[d]thiazole-7-sulfonic acid (T1)

$^1$H NMR (400 MHz, DMSO) δ 7.87 (d, J=8.6 Hz, 2H), 7.72 (d, J=8.1 Hz, 1H), 7.27 (d, J=8.6 Hz, 1H), 7.21 (s, 1H), 7.08 (s, 1H), 6.95 (s, 1H), 6.81 (s, br. 2H), 3.43 (q, J=7.0, 4H), 2.66 (s, 3H), 1.14 (t, J=7.0, 6H). HRMS (m/z): calcd for $C_{18}H_{21}N_2O_3S_2$ (neutral M+H) 377.0994. found 377.0967.

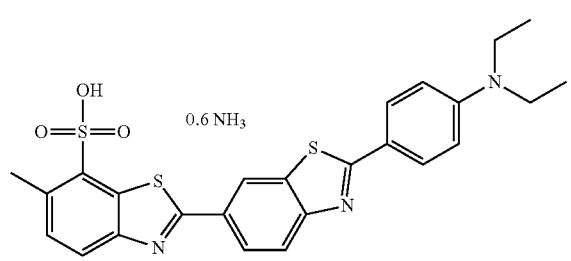

2'-(4-(diethylamino)phenyl)-6-methyl-[2,6'-bibenzo[d]thiazole]-7-sulfonic acid (T2)

$^1$H NMR (400 MHz, DMSO) δ 8.79 (d, J=1.8 Hz, 1H), 8.17 (dd, J=1.8, 8.5 Hz, 1H), 8.01 (d, J=8.4 Hz, 1H), 7.91 (d, J=9.0 Hz, 2H), 7.88 (d, J=8.1 Hz, 1H), 7.36 (d, J=8.6 Hz, 1H), 7.20 (s, 1H), 7.07 (s, 1H), 6.95 (s, 1H), 6.81 (d, J=9.0 Hz, 2H), 3.45 (q, J=7.0 Hz, 4H), 1.15 (t, J=7.0, 6H). HRMS (m/z): calcd for $C_{25}H_{24}N_3O_3S_3$ (neutral M+H) 510.0980. found 510.0957.

While the expectation was that the isolated compounds would be methylated primuline derivatives, analytical data showed the isolated compounds T1 and T2 to be the N,N-diethylation products of the primuline monomeric and dimeric benzothiazoles. Both T1 and T2 manifested some inhibitory activity against helicase-catalyzed DNA unwinding (Table 2), but neither was as potent as thioflavine S or primuline, suggesting that a minor component of the dye was inhibiting HCV helicase action.

TABLE 2

| Compound | Helicase* $IC_{50}$ (µM) | DNA Binding* (Ethidium Bromide) $EC_{50}$ (µM) | DNA Binding* (SYBR Green I) $EC_{50}$ (µM) | ATPase* $IC_{50}$ (µM) |
|---|---|---|---|---|
| Thioflavine S | 24 ± 1.3 | >100 | 61 ± 36 | 50 ± 17 |
| T1 | 33 ± 24 | >100 | ND | >100 |
| T2 | 26 ± 21[#] | >100 | ND | ND |

*Helicase (MBHA), DNA binding (FID), and ATP hydrolysis were monitored in the presence of eight different concentrations of each compound (2-fold dilution series starting at 100 µM). $IC_{50}$ values were determined from dose-response curves. All values are means ± standard deviations from three independents titrations with inhibitor.
N.D., not determined.
[#]Average value from three different batches of compound.

Based upon these results, the dye primuline was also purchased and 100 mg was purified by reverse phase preparative HPLC. In total, six compounds were purified from primuline. The two major components, P1a (9.2 mg) and P2a (7.6 mg), were separated via direct reverse-phase preparative HPLC in 9.2% and 7.6% isolated yield (by weight of P1a and P2a, respectively).

from the silica gel chromatography of commercial primuline upon elution with 20% DCM/MeOH. Subsequent reverse-phase preparative HPLC purification afforded the relatively minor components P1b, P2b, P3 and P4, where P3 and P4 represented 0.49% and 0.23% isolated yield (by weight) of the dye, respectively. All purified compounds were composed of a central benzothiazole oligomer of 1-4 units terminating with a p-aminobenzene group.

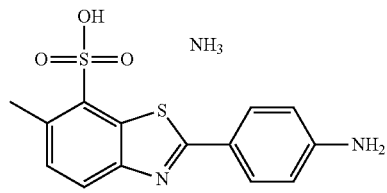

2-(4-aminophenyl)-6-methylbenzo[d]thiazole-7-sulfonic acid (P1a)

$^1$H NMR (400 MHz, DMSO) δ 7.76 (d, J=8.7 Hz, 2H), 7.72 (d, J=8.3 Hz, 1H), 7.26 (d, J=8.3 Hz, 1H), 7.23 (s, 1H), 7.10 (s, 1H), 6.98 (s, 1H), 6.69 (d, J=8.7 Hz, 2H), 2.65 (s, 3H). HRMS (m/z): calcd for $C_{14}H_{13}N_2O_3S_2$ (neutral M+H) 321.0367. found 321.0355.

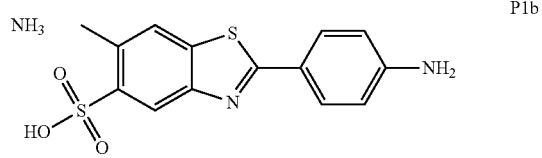

2-(4-aminophenyl)-6-methylbenzo[d]thiazole-5-sulfonic acid (P1b)

$^1$H NMR (400 MHz, DMSO) δ 8.21 (s, 1H), 7.76 (s, 1H), 7.75-7.71 (m, 2H), 7.23 (s, 1H), 7.10 (s, 1H), 6.98 (s, 1H), 6.66 (d, J=8.7 Hz, 2H), 5.87 (s, 2H), 2.64 (s, 3H). HRMS (m/z): calcd for $C_{14}H_{13}N_2O_3S_2$ (neutral M+H) 321.0367. found 321.0355.

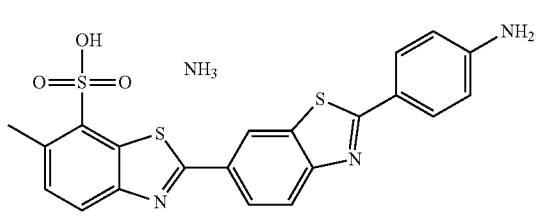

2'-(4-aminophenyl)-6-methyl-[2,6'-bibenzo[d]thiazole]-7-sulfonic acid (P2a)

$^1$H NMR (400 MHz, DMSO) δ 8.57 (d, J=1.8 Hz, 1H), 7.94 (dd, J=1.8, 8.5 Hz, 1H), 7.78 (d, J=8.5 Hz, 1H), 7.66 (d, J=8.6 Hz, 1H), 7.61 (d, J=8.7 Hz, 2H), 7.14 (d, J=8.6 Hz, 1H), 6.99 (s, 1H), 6.86 (s, 1H), 6.73 (s, 1H), 6.51 (d, J=8.7 Hz, 2H), 2.48 (s, 3H). $^{13}$C NMR (101 MHz, DMSO) δ 170.5, 168.8, 155.6, 152.4, 152.2, 140.1, 134.8, 133.0, 132.2, 130.1, 129.4, 129.0, 125.1, 122.5, 122.1, 120.7, 119.9, 113.7, 20.3. HRMS (m/z): calcd for $C_{21}H_{16}N_3O_3S_3$ (neutral M+H) 454.0354. found 454.0345.

In the MBHA, P2a was significantly less potent then the primuline mixture, while P1a was effectively inactive (Table 3). That the purified major component P2a did not possess increased potency compared to the mixture containing the inactive P1a was unexpected and hinted that perhaps highly potent components could be present in the primuline mixture in small amounts. The direct isolation of minor components via reverse-phase preparative HPLC of the dye mixture was not successful. Hence, the purification procedure was modified, enabling the isolation of four minor components.

The modified procedure included absorbing 1.0 g of primuline on 5.0 g of silica gel and collecting fractions from elution of the silica gel with 20% DCM/MeOH. Four chromatographic bands (UV and LC-MS) were obtained

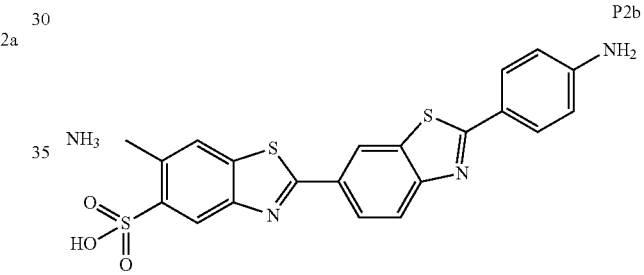

2'-(4-aminophenyl)-6-methyl-[2,6'-bibenzo[d]thiazole]-5-sulfonic acid (P2b)

$^1$H NMR (400 MHz, DMSO) δ 8.80 (d, J=1.8 Hz, 1H), 8.35 (s, 1H), 8.15 (dd, J=1.9, 8.5 Hz, 1H), 8.01 (d, J=8.5 Hz, 1H), 7.90 (s, 1H), 7.81 (d, J=8.7 Hz, 2H), 7.20 (s, 1H), 7.08 (s, 1H), 6.95 (s, 1H), 6.69 (d, J=8.7 Hz, 2H), 6.02 (s, 2H), 2.68 (s, 3H). HRMS (m/z): calcd for $C_{21}H_{16}N_3O_3S_3$ (neutral M+H) 454.0354. found 454.0347.

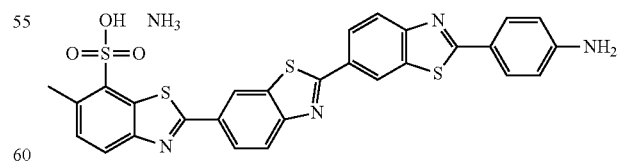

2''-(4-aminophenyl)-6-methyl-[2,6':2',6''-terbenzo[d]thiazole]-7-sulfonic acid (P3)

$^1$H NMR (400 MHz, DMSO) δ 8.96 (s, 1H), 8.88 (d, J=1.9 Hz, 1H), 8.30-8.25 (m, 1H), 8.25-8.20 (m, 1H), 8.18 (d,

J=8.5 Hz, 1H), 8.04 (d, J=8.5 Hz, 1H), 7.91 (d, J=8.1 Hz, 1H), 7.84 (d, J=8.7 Hz, 2H), 7.38 (d, J=8.6 Hz, 1H), 7.21 (s, 1H), 7.08 (s, 1H), 6.95 (s, 1H), 6.72 (d, J=8.7 Hz, 2H), 2.71 (s, 3H). HRMS (m/z): calcd for $C_{28}H_{19}N_4O_3S_4$ (neutral M+H) 587.0340. found 587.0332.

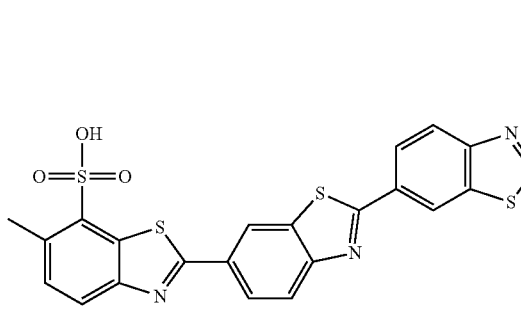
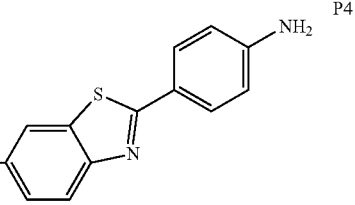

2'''-(4-aminophenyl)-6-methyl-[2,6':2'',6'''-quaterbenzo[d]thiazole]-7-sulfonic acid (P4)

$^1$H NMR (500 MHz, DMSO) δ 8.98 (s, 1H), 8.92 (s, 1H), 8.82 (s, 1H), 8.26 (d, J=8.5, 1H), 8.22 (d, J=8.5, 1H), 8.15 (t, J=8.5, 3H), 7.98 (d, J=8.5, 1H), 7.84 (d, J=8.1, 1H), 7.76 (d, J=8.6, 2H), 7.31 (d, J=8.2, 1H), 6.63 (d, J=8.6, 2H), 5.99 (s, 2H), 2.65 (s, 3H). HRMS (m/z): calcd for $C_{35}H_{22}N_5O_3S_5$ (neutral M+H) 720.0326. found 720.0319.

In the MBHA, all of the compounds purified from primuline were helicase inhibitors although P1a and P1b only partially inhibited unwinding at the highest concentrations tested (Table 3). Potency correlated with the length of the benzothiazole chain. For P3 or P4, only about 1 μM of either was needed to reduce the rate of helicase catalyzed DNA unwinding by 50%.

TABLE 3

| Compound | Helicase* IC$_{50}$ (μM) | DNA Binding* (Ethidium Bromide) EC$_{50}$ (μM) | DNA Binding* (SYBR Green I) EC$_{50}$ (μM) | ATPase* IC$_{50}$ (μM) |
|---|---|---|---|---|
| Primuline | 12 ± 1 | >100 | 43 ± 14 | 67 ± 27 |
| P1a | 70 ± 31 | >100 | >100 | >100 |
| P1b | 122 ± 5 | >100 | >100 | >100 |
| P2a | 49 ± 45# | >100 | N.D. | N.D. |
| P2b | 10 ± 4.6 | 73 ± 36 | 32 ± 3 | >100 |
| P3 | 0.9 ± 0.1 | 55 ± 20 | N.D. | 15 ± 4 |
| P4 | 0.8 ± 0.2† | 15 ± 3 | 15 ± 8 | 5 ± 3 |

*Helicase (MBHA), DNA binding (FID), and ATP hydrolysis were monitored in the presence of eight different concentrations of each compound (2-fold dilution series starting at 100 μM). IC$_{50}$ values were determined from dose-response curves. All values are means ± standard deviations from three independents titrations with inhibitor.
N.D., not determined.
Average value from three different batches of compound.
†Average value from two different batches of compound.

The purified compounds resembled compounds known to bind DNA, typically along the minor groove, such as the cyanine dye known as BEBO (Bengtsson, et al. (2003) Nucleic Acids Res. 31:e45), but unlike many DNA binding benzothiazoles, these helicase inhibitors were not positively charged. Instead they were anionic due to the sulfonate groups on the terminal benzothiazole rings. FID assays with the purified compounds revealed that they possessed some ability to bind DNA. Like thioflavine S, all compounds, except T1, P1a and P1b, decreased the fluorescence of ethidium bromide-bound DNA by at least 10% when present at 100 μM. However, only compounds P3 and P4 decreased ethidium bromide-bound DNA fluorescence more than 50% at the highest concentration tested (100 μM). P3 decreased the fluorescence of ethidium bromide-bound DNA with an EC$_{50}$ of 55±20 μM, and P4 decreased fluorescence with an EC$_{50}$ of 15±3 μM.

Because P3 and P4 clearly interacted with ethidium bromide-stained DNA, it was contemplated that the other benzothiazoles might also bind DNA, but in ways that do not displace the intercalated ethidium bromide. The effect of each compound on DNA stained with other dyes was examined, and it was found that most compounds decreased the fluorescence of DNA stained with SYBR Green I. The affinity of primuline, thioflavine S and the purified compounds for the MBHA substrate DNA was therefore estimated using a modified FID assay where ethidium bromide was replaced with SYBER Green I. The results were less drastic compared to those seen with ethidium bromide, with P4 binding slightly more tightly than all other compounds (Table 3).

It should be noted that, assuming that IC$_{50}$ values in MBHA reflect dissociation constants for a compound-helicase-DNA complex, it appears thioflavine S and primuline bind the helicase complex more tightly than they bind DNA alone, and P4 binds DNA 17-times more weakly. These data indicate that little, if any, compound was bound to DNA in MBHAs at concentrations needed to inhibit helicase action, indicating that the yellow dye-derived benzothiazoles inhibit HCV helicase directly.

If the purified benzothiazoles inhibited helicase-catalyzed nucleic acid unwinding by directly binding NS3, then they might also inhibit other functions of NS3, namely ATP hydrolysis in the presence and absence of stimulating nucleic acids. The most potent compound, P4 was therefore added to NS3 ATPase assays. The compound inhibited both assays in a dose-dependent manner. P4 inhibited ATP hydrolysis both in the presence and absence of RNA, indicating that the compound was not simply sequestering RNA and preventing activation of ATP hydrolysis. It was also interesting to note that far more P4 was needed to inhibit ATP hydrolysis in the absence of RNA, indicating that the presence of nucleic acid might enhance the affinity of the compound for the enzyme. It is not uncommon for helicase inhibitors to inhibit the protein's ability to hydrolyze ATP since ATP hydrolysis is needed to fuel unwinding. When ATPase assays were performed with compounds isolated from thioflavine S and primuline (Tables 2 and 3) the same pattern was observed that was seen in the MBHAs and FIDs (i.e., the longer benzothiazole oligomers were always more potent in all assays than the shorter oligomers).

Most of the compounds isolated from the two yellow dyes were fluorescent, absorbing light around 340 nm, and emitting near 420 nm. Their extinction coefficient and peak absorption wavelengths increased as the length of the benzothiazole oligomer increased. Their relative fluorescence decreased with the length of the benzothiazole chain. None of the compounds absorbed light near either the absorption or emission wavelengths of the Cy5-labeled MBHA substrate, or the wavelengths where the fluorescence of ethidium bromide stained DNA, SYBER green I-stained DNA, NS3-catalyzed peptide cleavage, or ATP hydrolysis were measured.

To determine if the above identified compounds might be useful as HCV antiviral agents, they were added to cells harboring HCV subgenomic RNA replicon. The HCV replicon chosen was derived from the same HCV strain (genotype 1b) as the NS3 protein used for screening and enzyme assays. The replicon was a variant of the replicon first reported by Lohmann, et al. (1999) *Science* 285:110-113) with two cell culture adaptive mutations (E1202G and S2204I; Krieger, et al. (2001) *J. Virol.* 75:4614-4624; Blight, et al. (2002) *J. Virol.* 76:13001-13014). The subgenomic replicon used here also had a *Renilla* luciferase gene fused to the 5' end of the neomycin phosphotransferase gene used for selection, such that, the cellular levels of *Renilla* luciferase correlated with the amount of HCV RNA present in cells (Huang, et al. (2006) supra). After replicon transfection and selection, cells were treated in parallel with one of the compounds purified from thioflavine S and primuline, or one of four recently reported HCV helicase inhibitors 1-4 (Gemma, et al. (2011) *Bioorg. Med. Chem. Lett.* 21:2776-2779; Stankiewicz-Drogon, et al. (2010) *J. Med. Chem.* 53:3117-3126; Chen, et al. (2009) *J. Med. Chem.* 52:2716-2723; Najda-Bernatowicz, et al. (2010) *Bioorg. Med. Chem.* 18:5129-5136), in two triplicate sets.

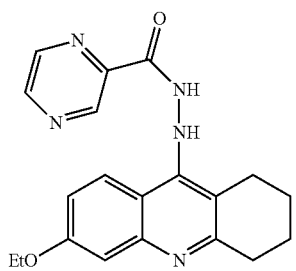

1

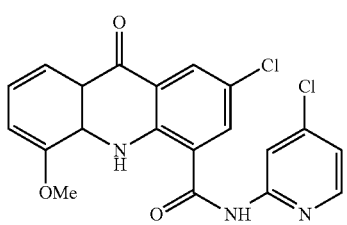

2

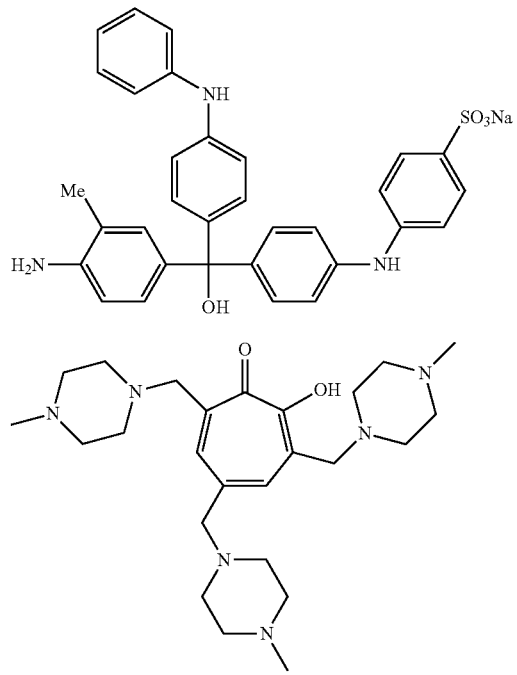

3

4

One set of cells was used for *Renilla* luciferase assays and the other set was used to determine cell viability using a firefly luciferase-based assay and all compounds were tested at 10 μM. While none of the compounds isolated from the yellow dyes were notably toxic to cells, only P3 and P4 showed any ability to decrease the amount of HCV RNA present in the cultures (Table 4). The ability of P3 and P4 to inhibit HCV replication was similar to that of the helicase inhibitors tested. None of the comparison helicase inhibitors were particularly toxic at 10 μM except for 1. Only compound 3 inhibited MBHAs with a potency similar to the yellow dyes, although the precise effects of compounds 3 and 4 on HCV helicase action were difficult to assess because both interfered with the MBHA.

TABLE 4

| Compound | Helicase* $IC_{50}$ (μM) | DNA Binding* (Ethidium Bromide) $EC_{50}$ (μM) | DNA Binding* (SYBR Green I) $EC_{50}$ (μM) | ATPase* $IC_{50}$ (μM) |
| --- | --- | --- | --- | --- |
| 1 | >100 | >100 | >100 | >100 |
| 2 | 25 ± 6 | >100 | >100 | >100 |
| 3 | 17 ± 7 | 4 ± 2 | 20 ± 2 | >100 |
| 4 | 19 ± 8 | >100 | 74 ± 21 | >100 |

*Helicase (MBHA), DNA binding (FID), and ATP hydrolysis were monitored in the presence of eight different concentrations of each compound (2-fold dilution series starting at 100 μM). $IC_{50}$ values were determined from dose-response curves. All values are means ± standard deviations from three independents titrations with inhibitor.
N.D., not determined.

Example 4

Derivatives of P2

Only a very small quantity of P3 or P4 could be isolated from primuline (0.49% for P3 and 0.23% for P4), complicating the further investigation of these compounds in cell-based assays. In an effort to mimic the trimeric structure of P3, a semi-synthetic route was designed using the more abundant P1a or P2a as a starting material. All P2a derivatives were analyzed in assays measuring their inhibition of HCV helicase-catalyzed DNA unwinding, their affinity for DNA in the absence of helicase, their ability to inhibit the HCV replicon, and their effect on cell viability (Tables 5 and 6). In DNA binding assays, none of the P2a derivatives decreased the fluorescence of DNA-bound ethidium bromide by more than 10% even at 100 µM. However, like P3 and P4, many of the derivatives appeared to bind SYBR Green I-stained DNA, and these apparent $K_d$'s in SYBR green-based FIDs are reported. These dissociation constants should be interpreted with caution because it is possible that some derivatives bind DNA is such a way that they fail to displace SYBR green I.

Focus was also placed on the modification of amino group on the terminus of P2a as a convenient site to extend P2a in a manner consistent with the structure of P3. The range of P2a derivatives synthesized is summarized in Tables 5 and 6. It was envisioned that an appropriately rigid linker could substitute for the third benzothiazole ring of P3. Thus, the terminal amine of P2a was acylated to give amides, reacted with isocyanates or sulfonyl chlorides to give urea analogs and sulfonamides, respectively (Scheme 1).

SCHEME 1

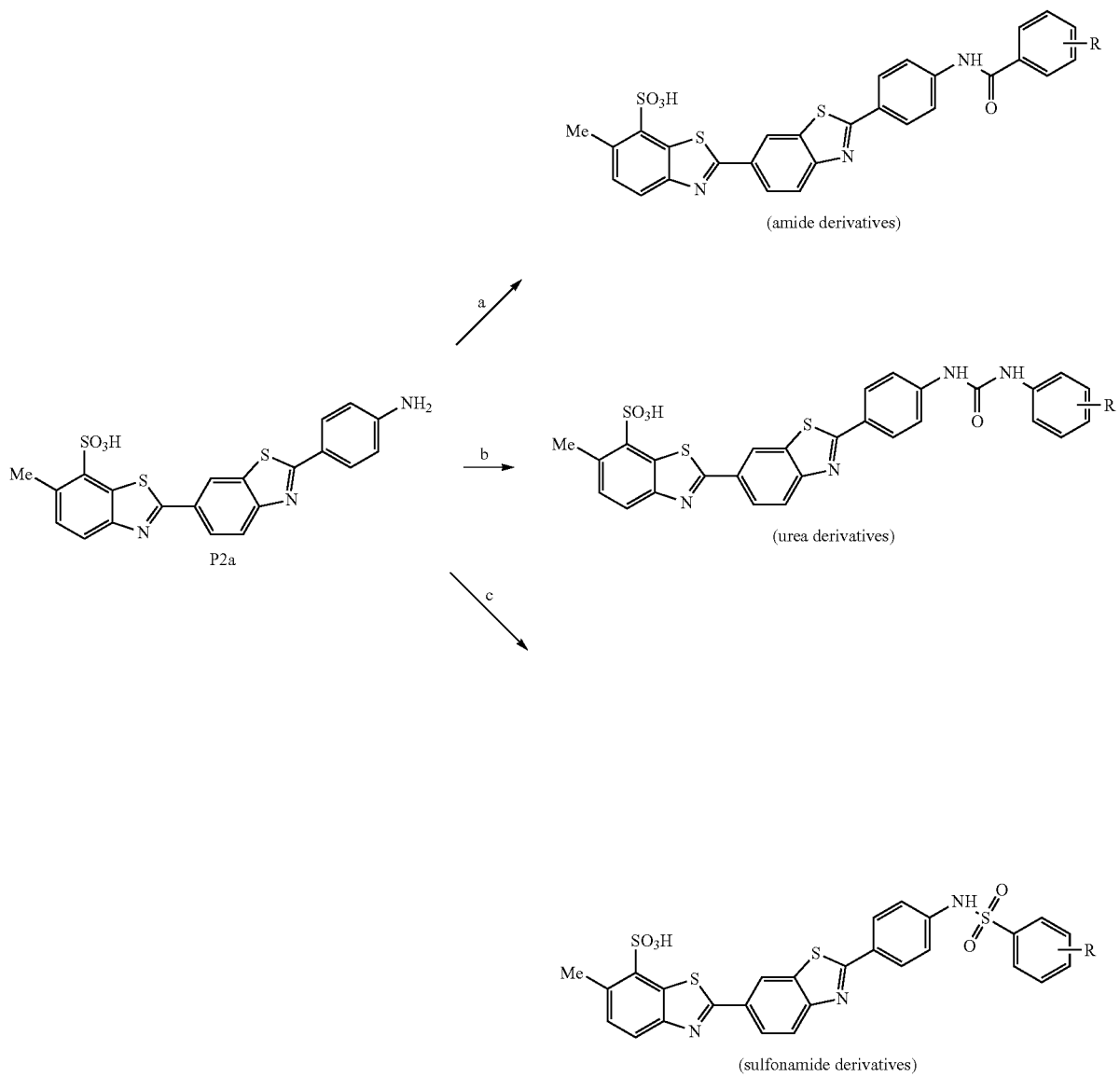

(a) substituted benzoyl chloride, pyridine, 80° C.; (b) arylisocyanate, DMF, 80 ° C.; (c) arylsulfonyl chloride, pyridine 80° C.

Table 5 illustrates the effect of different functional groups on substituted phenyl amide derivatives. This included electron-donating and electron-withdrawing groups as well as aliphatic groups.

TABLE 5

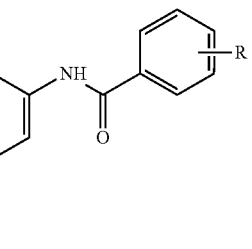

| Cmpd | R | Helicase IC$_{50}$ (µM)$^a$ | DNA binding (%)$^{a,b}$ | HCV replication (% Inh.)$^c$ | Cell viability (% viable)$^c$ |
|---|---|---|---|---|---|
| 5 | H | 11 ± 1.5 | 31 ± 13 | 45 ± 5 | 88 ± 2 |
| 6 | 4-NH$_2$ | 10 ± 2.4 | 63 ± 15 | 33 ± 1 | 93 ± 4 |
| 7 | 4-F | 5.2 ± 0.6 | 35 ± 15 | 50 ± 5 | 94 ± 2 |
| 8 | 4-OCH$_3$ | 10 ± 2.6 | 35 ± 10 | 64 ± 4 | 85 ± 5 |
| 9 | 4-CO$_2$CH$_3$ | 9.7 ± 4.6 | 28 ± 10 | 40 ± 1 | 101 ± 8 |
| 10 | 4-Cl | 3.4 ± 0.3 | 67 ± 17 | 42 ± 9 | 84 ± 6 |
| 11 | 4-CH$_3$ | 3.3 ± 0.3 | 50 ± 15 | 52 ± 12 | 87 ± 4 |
| 12 | 4-CF$_3$ | 1.8 ± 0.4 | 69 ± 9 | 44 ± 12 | 90 ± 4 |
| 13 | 4-t-Bu | 8.2 ± 1 | 72 ± 19 | 51 ± 9 | 87 ± 4 |
| 14 | 4-N(CH$_3$)$_2$ | 11 ± 6.7 | 44 ± 4 | 22 ± 2 | 94 ± 5 |
| 15 | 4-Br | 5.2 ± 4 | 70 ± 9 | 7 ± 18 | 113 ± 5 |
| 16 | 4-NHFmoc | 5.4 ± 1 | 76 ± 5 | 57 ± 21 | 92 ± 4 |
| 17 | 3-Cl | 2.6 ± 1 | 41 ± 11 | 54 ± 10 | 112 ± 4 |
| 18 | 3,4-di-Cl | 3.7 ± 1 | 67 ± 12 | 43 ± 15 | 114 ± 7 |
| 19 | 2-CF$_3$ | 14 ± 1 | 30 ± 15 | 0 ± 9 | 112 ± 1 |
| 20 | 3-CF$_3$ | 20 ± 12 | 46 ± 10 | 41 ± 8 | 121 ± 3 |
| 21 | 2-F, 6-CF$_3$ | 17 ± 6 | 66 ± 40 | 55 ± 7 | 122 ± 2 |
| 22 | 2-F, 3-CF$_3$ | 9.2 ± 3 | 49 ± 27 | 48 ± 18 | 122 ± 1 |
| 23 | 3-F, 4-CF$_3$ | 17 ± 17 | 66 ± 18 | 48 ± 4 | 129 ± 2 |
| 24 | 3,5-di-CF$_3$ | 22 ± 4 | 43 ± 13 | 60 ± 4 | 122 ± 5 |
| 25 | 2-F, 5-CF$_3$ | 6.4 ± 2 | 35 ± 26 | 39 ± 4 | 132 ± 14 |
| 26 | 3-F, 6-CF$_3$ | 19 ± 15 | 35 ± 21 | 61 ± 14 | 118 ± 4 |
| 27 | 3-F, 5-CF$_3$ | 28 ± 7 | 48 ± 17 | 51 ± 9 | 113 ± 1 |

$^a$Helicase (MBHA), DNA binding (SYBR Green I-FID) were monitored in the presence of eight different concentrations of each compound (2-fold dilution series starting at 100 µM). IC$_{50}$ values were determined from concentration-response curves. All values are means ± standard deviations from three independent titrations with inhibitor.
$^b$Average (±SD) percent bound at 100 µM.
$^c$Cell viability and HCV replicon assays were performed in triplicate in the presence of 10 µM compound. Average (±SD) percent inhibition or viability is reported.

While replacing the para substitution R=H with NH$_2$, OCH$_3$, CO$_2$CH$_3$, t-Bu and N(CH$_3$)$_2$ had no significant effect on the potency of helicase inhibition, replacement with F, Br and NHFmoc groups led to slightly more potent analogues (2-fold, compared to R—H). Even better analogs (3-5-fold) were obtained when Cl, CH$_3$, CF$_3$ and 2-naphthalene groups were used (compound 33, Table 6). The increased size of alkyl substitution from Me to t-Bu resulted in an approximately 3-fold activity loss. Altering the Cl position from para to meta had no change on helicase inhibition, although the meta substitution displayed weaker DNA binding. Increasing the number of chloro groups as in 18 showed no improvement across the assays. Moving the CF$_3$ group from para position to ortho or meta position showed a reduction in activity (7-10 fold, compounds 12, 19 and 20). Introducing additional fluorine groups to the derivatives had no effect on the helicase inhibition compared to 12 (see 21 to 27). In fact, depending on the position of fluorine substitution, a significant decrease in potency was observed. In DNA-binding assays, none of the P2a derivatives decreased the fluorescence of DNA-bound ethidium bromide by more than 10%, even at 100 µM. Like P3 and P4, many of the derivatives appeared to bind SYBR Green I-stained DNA. However, unlike P3 and P4, many of the derivatives did not displace more than 50% SYBR Green I at the highest concentration tested (100 µM). Therefore, to compare the DNA-binding potential of all derivatives, the percent SYBR Green I displaced at the highest concentration tested (100 µM) was compared rather than EC$_{50}$ values (Tables 5 and 6). Most of the amide derivatives were at least a 10-fold more potent in the MBHA than the DNA binding assay.

Solubility was also determined for several compounds. Solubility measurements were performed using a mock assay matrix (25 mM MOPS, 1.25 mM MgCl$_2$, 0.05 mM DTT, 5 µg/mL BSA, 0.01% v/v final TWEEN 20 concentration, and 5% v/v final DMSO concentration) at pH 6.5. This analysis indicated that compounds 7, 17, 18, and 24 had solubilities of 129.4, 29.2, 2.6 and 180.1, respectively.

Two additional types of derivatives were also explored. The urea analogs, which were synthesized from P2a by reacting P2a with different isocyanates and the sulfonamide analogs prepared via the sulfonation of P2a with sulfonyl chlorides (Table 6).

TABLE 6

[Core structure: 6-methyl-7-sulfo-benzothiazole linked at 2-position to 6-position of a second benzothiazole, which bears a 4-R-phenyl group at its 2-position]

| Cmpd | R | Helicase IC$_{50}$ (μM)$^a$ | DNA binding (%)$^{a,b}$ | HCV replication (% Inh.)$^c$ | Cell viability (% Viable)$^c$ |
|---|---|---|---|---|---|
| 28 | —NHC(O)NH-(4-methylphenyl) | 5.3 ± 0.9 | 90 ± 9 | 43 ± 9 | 93 ± 1 |
| 29 | —NHS(O)$_2$-(4-methoxyphenyl) | 24 ± 2.2 | 69 ± 4 | 44 ± 5 | 75 ± 3 |
| 30 | NHC(O)Me | >100 | 48 ± 5 | 1 ± 12 | 100 ± 6 |
| 31 | —NHC(O)-(3-pyridyl) | 22 ± 2 | 15 ± 10 | 51 ± 22 | 113 ± 6 |
| 32 | —NHC(O)-(4-pyridyl) | 52 ± 20 | 19 ± 7 | 59 ± 13 | 117 ± 5 |
| 33 | —NHC(O)-(2-naphthyl) | 2.7 ± 0.7 | 64 ± 7 | 61 ± 10 | 87 ± 4 |
| 34 | —N(Me)C(O)-(2-naphthyl) | 14 ± 0.1 | 35 ± 23 | −30 ± 30 | 98 ± 0.7 |
| 35 | —NHC(O)-[2-(4-aminophenyl)benzothiazol-6-yl] | 5.5 ± 2.1 | 59 ± 4 | 37 ± 4 | 85 ± 2 |

TABLE 6-continued

[Structure: Me-substituted benzothiazole with SO3H group connected to another benzothiazole connected to phenyl-R]

| Cmpd | R | Helicase IC$_{50}$ (μM)$^a$ | DNA binding (%)$^{a,b}$ | HCV replication (% Inh.)$^c$ | Cell viability (% Viable)$^c$ |
|---|---|---|---|---|---|
| 36 | [amide-linked benzothiazole-phenyl-NHFmoc structure] | 4.0 ± 2.4 | 67 ± 5 | 42 ± 5 | 90 ± 4 |

$^a$Helicase (MBHA), DNA binding (SYBER Green I-FID) were monitored in the presence of eight different concentrations of each compound (2-fold dilution series starting at 100 μM). IC$_{50}$ values were determined from concentration-response curves. All values are means ± standard deviations from three independent titrations with inhibitor.
$^b$Average (±SD) percent bound at 100 μM.
$^c$Cell viability and HCV replicon assays were performed in triplicate in the presence of 10 μM compound. Average (±SD) percent inhibition or viability is reported.

The urea analog 28 (DNA binding was 13 μM) had comparative potency in the MBHA as the amide analog 11, although increased DNA binding was observed (13 μM for 28 compared to >100 μM for 11). Less potent analogs were achieved via sulfonation (e.g., 29, 2-fold activity drop) compared to 11. Replacing substituted phenyl with methyl (30) resulted in the loss of activity. Analogs targeting improved solubility by replacing the phenyl ring of 5 with pyridine ring, produced less potent analogs (2-5 fold decrease in helicase activity, 31, 32). N-methylation of the naphythyl analog 33 also caused a significant drop in activity (5-fold, 34) which could indicate the loss of a key hydrogen bond interaction.

Solubility measurements for compound 33 were performed using a mock assay matrix (25 mM MOPS, 1.25 mM MgCl$_2$, 0.05 mM DTT, 5 μg/mL BSA, 0.01% v/v final TWEEN 20 concentration, and 5% v/v final DMSO concentration) at pH 6.5. The results indicated that compound 33 had a solubility of 3.7 μM. Solubility measurements for compound 31 were performed using MOPS buffer (25 mM MOPS, 1.25 mM MgCl$_2$, 2% v/v final DMSO concentration) at pH 6.5. This analysis indicated a solubility of >100 μM.

In an effort to mimic the tetrameric structure of P4, the more elaborate amide derivatives 35 and 36 were synthesized. No improvements in potency were observed for the tetrameric analogues 35 and 36 over the previous trimeric analogues. The simple one-step synthesis of the trimeric analogues compared to the tetrameric analogues prompted focus to be placed on the former for future studies targeting more potent inhibitors of helicase function and HCV replication.

When all derivatives (5-36) were compared with the purified compounds and the recently reported helicase inhibitors (1-4), it was clear that most compounds that bound DNA in the FID assay also interfered with the MBHA by quenching substrate fluorescence. The most potent benzothiazoles were notably more effective than the recently reported helicase inhibitors used for comparison, two of which appeared to function primarily by interacting with the DNA substrate (compounds 3 and 4). Compound 17 was the most potent compound that did not interfere with the MBHA, and it eliminated the HCV replicon without apparent toxicity, similar to both P3 and P4. Also, like P4, compound 17 inhibited HCV helicase-catalyzed RNA-unwinding and ATP hydrolysis.

The pharmacokinetic (PK) properties of compound 17 were profiled using a standard panel of assays (Tables 7 and 8). The most striking result was the solubility variation depending on the buffer system used. While the aqueous solubility was low in the PBS-based solvent system (Table 7), in both the detergent-containing (TWEEN 20) assay matrix and the proprietary PRISMA HT buffer system, the compound was readily soluble. The unknown identity of the components in the PRISMA HT buffer system complicated further speculation into the solubility discrepancy. Compound 17 was, however, highly stable under the various conditions screened and possessed no detectable hepatic toxicity (Table 8).

TABLE 7

| Aqueous Solubility (μg/ml)$^a$ (at pH) | | | PAMPA Pe |
|---|---|---|---|
| Prisma HT buffer$^a$ | PBS$^b$ | Assay Matrix$^c$ | (×10$^{-6}$ cm/s)$^d$ (at pH) |
| 36.7 (5.0) | | | 0 (5.0) |
| >60 (6.2) | 0.12 (7.4) | 17.8 (6.5) | 0.22 (6.2) |
| >60 (7.4) | | | 0 (7.4) |

$^a$In aqueous pION's PRISMA HT buffer, pHs 5.0/6.2/7.4.
$^b$In aqueous PBS, pH 7.4.
$^c$In a mock assay matrix (25 mM MOPS, 1.25 mM MgCl$_2$, 0.05 mM DTT, 5 μg/mL BSA, 0.01% v/v final TWEEN 20 concentration, and 5% v/v final DMSO concentration) at pH 6.5.
$^d$In aqueous buffer; donor compartment pH's 5.0/6.2/7.4; acceptor compartment pH 7.4.

TABLE 8

| Plasma Protein Binding (% Bound) | | Plasma Stability[a] | | Hepatic Microsome Stability[c] | | Hepatic Toxicity[d] |
|---|---|---|---|---|---|---|
| Human | Mouse | Human/ | Aqueous | | | |
| 1 μM/10 μM | 1 μM/10 μM | Mouse | Stability[b] | Human | Mouse | LC$_{50}$ (μM) |
| 98/99 | 98/99 | 96.6/95.0 | 100 | 83.57 | 83.11 | >50 |

[a]Percent remaining at 3 hours.
[b]In aqueous PBS buffer with 50% acetonitrile, pH 7.4; % remaining after 48 hours at room temperature.
[c]Percent remaining at 1 hour.
[d]Toward Fa2N-4 immortalized human hepatocytes.

Example 5

Synthesis of Inhibitors

Synthesis of T2 from P2a.

To a suspension of sodium hydride (6.2 mg, 0.154 mmol) in DMF (2 mL), was added 2'-(4-aminophenyl)-6-methyl-2,6'-bibenzo[d]thiazole-7-sulfonic acid (20 mg, 0.044 mmol) (P2a) at room temperature. After no bubble evolved, iodoethane (35.5 μl, 0.44 mmol) was added dropwise. The mixture was stirred at room temperature for 3 days. The reaction mixture was purified via reverse phase combiflash (C18 RediSep Rf column) to give T2 (4.0 mg, 19% yield) and the monoethyl primuline derivative 2'-(4-(ethylamino) phenyl)-6-methyl-2,6'-bibenzo[d]thiazole-7-sulfonic acid (11.9 mg, 56.0% yield).

Representative Procedure for the Synthesis of Trimer Amide Analogs.

To a solution of P2a (20 mg, 0.044 mmoL) in pyridine (1 mL) at 80° C., was added benzoyl chloride (7.7 mmL, 0.066 mmoL, 1.5 equiv.). The reaction mixture was stirred at 80° C. overnight. The product was isolated via reverse phase preparative HPLC Yield: 10.1 mg, 41%. The same procedure was used to synthesize the following compounds 5, 7-27, 31-33 and 36.

5

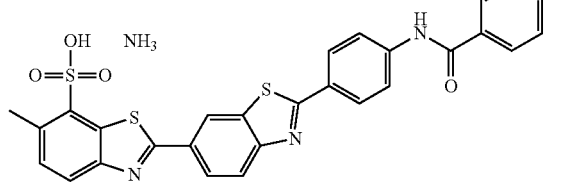

2'-(4-benzamidophenyl)-6-methyl-[2,6'-bibenzo[d]thiazole]-7-sulfonic acid (5)

Yield: 10.1 mg, 41%. $^1$H NMR (400 MHz, DMSO) δ 10.61 (s, 1H), 8.93 (d, J=1.8 Hz, 1H), 8.26 (dd, J=1.8, 8.5 Hz, 1H), 8.18-8.15 (m, 3H), 8.06 (d, J=8.9 Hz, 2H), 8.04-7.96 (m, 2H), 7.92 (d, J=8.0 Hz, 1H), 7.66-7.62 (m, 1H), 7.58 (t, J=7.3 Hz, 2H), 7.39 (d, J=8.6 Hz, 1H), 7.22 (s, 1H), 7.10 (s, 1H), 6.97 (s, 1H), 2.72 (s, 3H). $^{13}$C NMR (101 MHz, 13C ATP DMSO) δ 169.3, 168.6, 165.9, 155.2, 152.2, 142.4, 140.1, 135.4, 134.6, 133.2, 132.3, 131.9, 130.3, 130.1, 128.4, 128.1, 127.8, 127.7, 125.4, 123.0, 122.6, 121.2, 120.4, 20.3. HRMS (m/z): calcd for C$_{28}$H$_{20}$N$_3$O$_4$S$_3$ (M+H) 558.0616. found 558.0615.

6

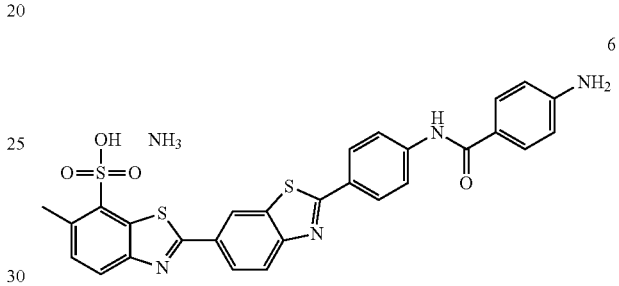

2'-(4-(4-aminobenzamido)phenyl)-6-methyl-[2,6'-bibenzo[d]thiazole]-7-sulfonic acid (6)

To a solution of P2a (24 mg, 0.053 mmol) in pyridine (3 mL), was added (9H-Fluoren-9-yl)methyl 4-(chlorocarbonyl)phenylcarbamate (30.0 mg, 0.079 mmol) at 80° C. The reaction mixture was stirred at 80° C. overnight. Solvents were removed under vacuum, and the residue was dissolved in DMF (6 mL). Morpholine (41 μL, 0.46 mmol) was added. The mixture was stirred at room temperature for 16 hours. The product was purified by reverse phase preparative HPLC. Yield: 8.2 mg, 31% (2 steps). $^1$H NMR (400 MHz, DMSO) δ 10.08 (s, 1H), 8.84 (d, J=1.8 Hz, 1H), 8.22-8.13 (m, 1H), 8.13-8.01 (m, 3H), 7.95 (d, J=8.9 Hz, 2H), 7.84 (d, J=8.1 Hz, 1H), 7.73 (d, J=8.7 Hz, 2H), 7.32 (d, J=8.6 Hz, 1H), 7.16 (s, 1H), 7.03 (s, 1H), 6.90 (s, 1H), 6.62 (d, J=8.7 Hz, 2H), 2.65 (s, 3H). $^{13}$C NMR (101 MHz, DMSO) δ 169.5, 168.6, 165.5, 155.2, 152.2, 143.1, 140.1, 135.4, 133.2, 132.3, 130.2, 130.1, 129.6, 129.0, 128.0, 127.0, 125.4, 122.9, 122.6, 121.3, 121.1, 120.1, 113.2, 20.3. HRMS (m/z): calcd for C$_{28}$H$_{21}$N$_4$O$_4$S$_3$ (M+H) 573.0725. found 573.0719.

7

2'-(4-(4-fluorobenzamido)phenyl)-6-methyl-[2, bibenzo[d]thiazole]-7-sulfonic acid (7)

Yield: 9.2 mg, 36%. $^1$H NMR (400 MHz, DMSO) δ 10.61 (s, 1H), 8.93 (d, J=1.8 Hz, 1H), 8.26 (dd, J=1.8, 8.5 Hz, 1H), 8.21-8.13 (m, 3H), 8.13-8.07 (m, 2H), 8.07-8.00 (m, 2H), 7.92 (d, J=8.0 Hz, 1H), 7.43-7.38 (m, 3H), 7.22 (s, 1H), 7.10 (s, 1H), 6.97 (s, 1H), 2.72 (s, 3H). $^{13}$C NMR (101 MHz, DMSO) δ 169.3, 168.6, 164.7, 163.0, 155.2, 152.2, 142.3, 140.1, 135.4, 133.2, 132.3, 131.04, 131.01, 130.6, 130.5, 130.3, 130.1, 128.1, 127.8, 125.4, 123.0, 122.6, 121.2, 120.4, 115.5, 115.3, 20.3. HRMS (m/z): calcd for $C_{28}H_{19}FN_3O_4S_3$ (M+H) 576.0522. found 576.0509.

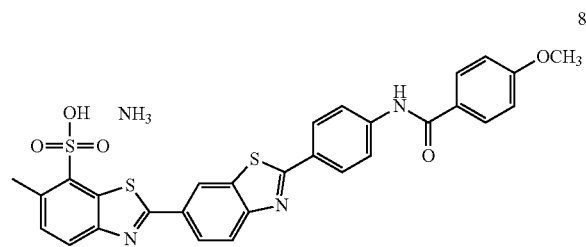

2'-(4-(4-methoxybenzamido)phenyl)-6-methyl-[2,6'-bibenzo[d]thiazole]-7-sulfonic acid (8)

Yield: 6.7 mg, 26%. $^1$H NMR (400 MHz, DMSO) δ 10.44 (s, 1H), 8.93 (dd, J=1.8 Hz, 1H), 8.26 (dd, J=1.8, 8.5 Hz, 1H), 8.17-8.14 (m, 3H), 8.10-7.97 (m, 4H), 7.92 (d, J=8.0 Hz, 1H), 7.39 (d, J=8.6 Hz, 1H), 7.22 (s, 1H), 7.12-7.09 (m, 2H), 7.09 (s, 1H), 6.96 (s, 1H), 3.87 (s, 3H), 2.72 (s, 3H). $^{13}$C NMR (101 MHz, DMSO) δ 169.4, 168.6, 165.2, 162.1, 155.2, 152.2, 142.7, 140.1, 135.4, 133.2, 132.3, 130.3, 130.1, 129.8, 128.0, 127.5, 126.6, 125.4, 123.0, 122.6, 121.2, 120.3, 113.7, 55.5, 20.3. HRMS (m/z): calcd for $C_{29}H_{22}N_3O_5S_3$ (M+H) 588.0722. found 588.0706.

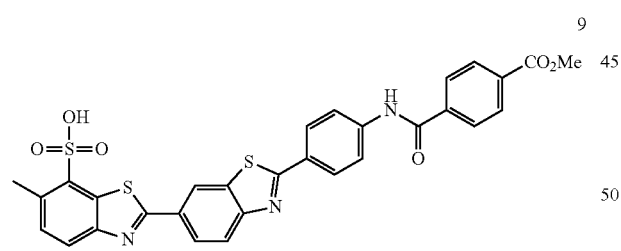

2'-(4-(4-(methoxycarbonyl)benzamido)phenyl)-6-methyl-[2,6'-bibenzo[d]thiazole]-7-sulfonic acid (9)

Yield: 5.5 mg, 41%. $^1$H NMR (500 MHz, DMSO) δ 10.79 (s, 1H), 8.93 (d, J=1.8 Hz, 1H), 8.25 (dd, J=1.8, 8.5 Hz, 1H), 8.18-8.15 (m, 3H), 8.12 (s, br. 4H), 8.05 (d, J=8.8 Hz, 2H), 7.91 (d, J=8.0 Hz, 1H), 7.38 (d, J=8.6 Hz, 1H), 7.20 (s, 1H), 7.09 (s, 1H), 6.99 (s, 1H), 3.91 (s, 3H), 2.71 (s, 3H). $^{13}$C NMR (126 MHz, DMSO) δ 169.3, 168.6, 165.6, 165.0, 155.2, 152.2, 142.1, 140.1, 138.7, 135.4, 133.2, 132.3, 132.2, 130.3, 130.1, 129.2, 128.2, 128.1, 128.0, 125.4, 123.0, 122.6, 121.2, 120.5, 52.5, 20.2. HRMS (m/z): calcd for $C_{30}H_{22}N_3O_6S_3$ (M+H) 616.0671. found 616.0658.

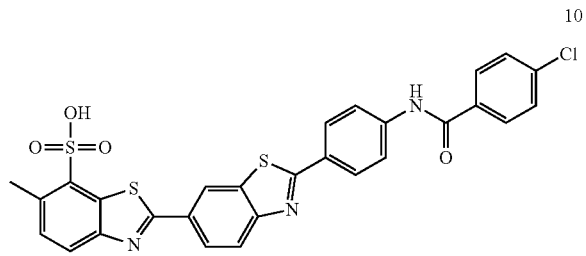 [SMILES: Cc1ccc2nc(-c3ccc4nc(-c5ccc(NC(=O)c6ccc(Cl)cc6)cc5)sc4c3)sc2c1S(=O)(=O)O]

2'-(4-(4-chlorobenzamido)phenyl)-6-methyl-[2,6'-bibenzo[d]thiazole]-7-sulfonic acid (10)

Yield: 6.5 mg, 50%. $^1$H NMR (400 MHz, DMSO) δ 10.67 (s, 1H), 8.94 (d, J=1.8 Hz, 1H), 8.26 (dd, J=1.8, 8.6 Hz, 1H), 8.19-8.15 (m, 3H), 8.06-8.04 (m, 4H), 7.91 (d, J=8.0 Hz, 1H), 7.66 (d, J=8.7 Hz, 2H), 7.39 (d, J=8.7 Hz, 1H), 7.06 (s, br. 3H), 2.72 (s, 3H). $^{13}$C NMR (126 MHz, DMSO) δ 169.29, 168.6, 164.8, 155.2, 152.2, 142.2, 140.1, 136.7, 135.4, 133.3, 133.2, 132.3, 130.3, 130.1, 129.8, 128.5, 128.1, 127.9, 125.4, 123.0, 122.6, 121.2, 120.5, 20.2. HRMS (m/z): calcd for $C_{28}H_{19}ClN_3O_4S_3$ (M+H) 592.0226. found 592.0211.

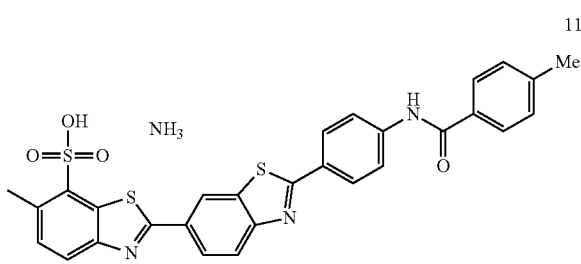

6-methyl-2'-(4-(4-methylbenzamido)phenyl)-[2,6'-bibenzo[d]thiazole]-7-sulfonic acid (11)

Yield: 2.3 mg, 18%. $^1$H NMR (500 MHz, DMSO) δ 10.52 (s, 1H), 8.92 (d, J=1.8 Hz, 1H), 8.28-8.22 (m, 1H), 8.16-8.15 (m, 3H), 8.05 (d, J=8.9 Hz, 2H), 7.93-7.90 (m, 3H), 7.42-7.33 (m, 3H), 7.20 (s, 1H), 7.10 (s, 1H), 6.99 (s, 1H), 2.71 (s, 3H), 2.41 (s, 3H). $^{13}$C NMR (126 MHz, DMSO) δ 169.4, 168.6, 165.7, 155.2, 152.1, 142.5, 142.0, 140.1, 135.4, 133.2, 132.3, 131.7, 130.3, 130.2, 129.0, 128.1, 127.8, 127.6, 125.4, 123.0, 122.6, 121.2, 120.4, 21.0, 20.2. HRMS (m/z): calcd for $C_{29}H_{22}N_3O_4S_3$ (M+H) 572.0772. found 572.0760.

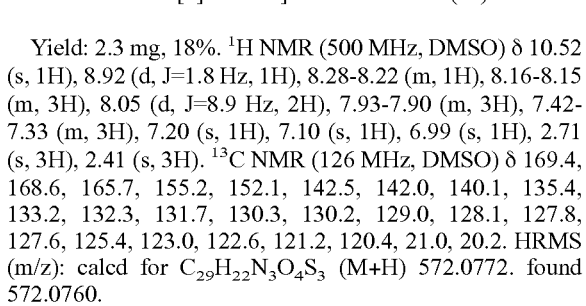

6-methyl-2'-(4-(4-(trifluoromethyl)benzamido)phenyl)-[2,6'-bibenzo[d]thiazole]-7-sulfonic acid (12)

Yield: 7.5 mg, 54%. $^1$H NMR (500 MHz, DMSO) δ 10.81 (s, 1H), 8.93 (d, J=1.8 Hz, 1H), 8.25 (dd, J=1.8, 8.5 Hz, 1H), 8.23-8.13 (m, 5H), 8.05 (d, J=8.8 Hz, 2H), 7.95 (d, J=8.3 Hz, 2H), 7.91 (d, J=8.0 Hz, 1H), 7.38 (d, J=8.5 Hz, 1H), 7.19 (s, 1H), 7.09 (s, 1H), 6.99 (s, 1H), 2.71 (s, 3H). $^{13}$C NMR (126 MHz, DMSO) δ 169.2, 168.6, 164.7, 155.2, 152.2, 142.0, 140.1, 138.4, 135.4, 133.2, 132.3, 131.9, 131.7, 131.4, 131.2, 130.3, 130.1, 128.7, 128.12, 128.07, 125.48, 125.45, 125.42, 125.39, 125.0, 123.1, 122.8, 122.6, 121.2, 120.5, 20.2. HRMS (m/z): calcd for C$_{29}$H$_{19}$F$_3$N$_3$O$_4$S$_3$ (M+H) 626.0490. found 626.0476.

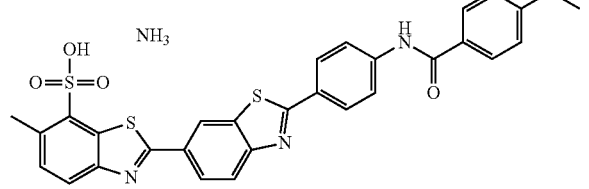

2'-(4-(4-(tert-butyl)benzamido)phenyl)-6-methyl-[2,6'-bibenzo[d]thiazole]-7-sulfonic acid (13)

Yield: 7.8 mg, 58%. $^1$H NMR (500 MHz, DMSO) δ 10.53 (s, 1H), 8.93 (d, J=1.8 Hz, 1H), 8.25 (dd, J=1.8, 8.5 Hz, 1H), 8.16-8.15 (m, 3H), 8.04 (d, J=8.8 Hz, 2H), 7.95-7.90 (m, 3H), 7.58 (d, J=8.6 Hz, 2H), 7.38 (d, J=8.5 Hz, 1H), 7.20 (s, 1H), 7.09 (s, 1H), 6.99 (s, 1H), 2.71 (s, 3H), 1.34 (s, 9H). $^{13}$C NMR (126 MHz, DMSO) δ 169.4, 168.6, 165.8, 155.2, 154.7, 152.2, 142.5, 140.1, 135.4, 133.2, 132.3, 131.9, 130.3, 130.1, 128.1, 127.7, 127.6, 125.4, 125.2, 123.0, 122.6, 121.2, 120.3, 34.7, 30.9, 20.3. HRMS (m/z): calcd for C$_{32}$H$_{28}$N$_3$O$_4$S$_3$ (M+H) 614.1242. found 614.1235.

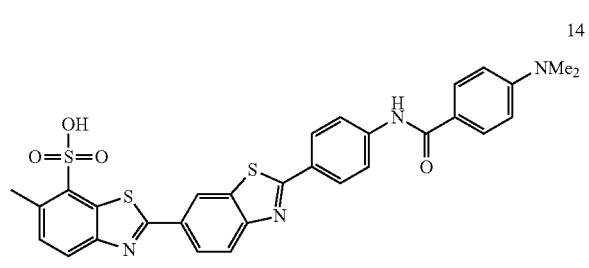 [SMILES: Cc1ccc2nc(-c3ccc4nc(-c5ccc(NC(=O)c6ccc(N(C)C)cc6)cc5)sc4c3)sc2c1S(=O)(=O)O]

2'-(4-(4-(dimethylamino)benzamido)phenyl)-6-methyl-[2,6'-bibenzo[d]thiazole]-7-sulfonic acid (14)

Yield: 10.7 mg, 54%. $^1$H NMR (500 MHz, DMSO) δ 10.22 (s, 1H), 8.92 (d, J=1.8 Hz, 1H), 8.25 (dd, J=1.8, 8.5 Hz, 1H), 8.17-8.09 (m, 3H), 8.04 (d, J=8.9 Hz, 2H), 7.93-7.90 (m, 3H), 7.38 (d, J=8.6 Hz, 1H), 7.19 (s, 1H), 7.09 (s, 1H), 6.98 (s, 1H), 6.79 (d, J=9.1 Hz, 2H), 3.02 (s, 6H), 2.71 (s, 3H). $^{13}$C NMR (126 MHz, DMSO) δ 169.5, 168.6, 165.4, 155.2, 152.6, 152.2, 143.1, 140.1, 135.4, 133.1, 132.3, 130.2, 130.1, 129.3, 128.0, 127.0, 125.4, 122.9, 122.6, 121.2, 120.5, 120.1, 110.7, 39.7, 20.2. HRMS (m/z): calcd for C$_{30}$H$_{25}$N$_4$O$_4$S$_3$ (M+H) 601.1038. found 601.1042.

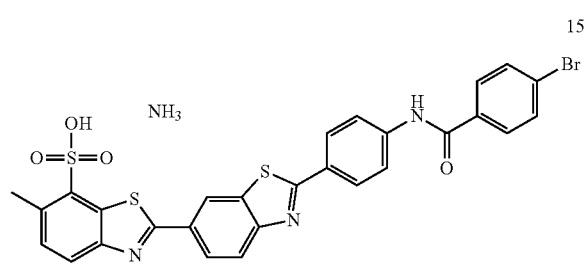

2'-(4-(4-bromobenzamido)phenyl)-6-methyl-[2,6'-bibenzo[d]thiazole]-7-sulfonic acid (15)

Yield: 7.6 mg, 54%. 1H $^1$H NMR (400 MHz, DMSO) δ 10.58 (s, 1H), 8.89-8.82 (m, 1H), 8.18 (dd, J=1.8, 8.5 Hz, 1H), 8.14-8.04 (m, 3H), 7.96 (d, J=8.9 Hz, 2H), 7.93-7.86 (m, 2H), 7.83 (d, J=8.0 Hz, 1H), 7.76-7.67 (m, 2H), 7.31 (d, J=8.6 Hz, 1H), 7.14 (s, 1H), 7.01 (s, 1H), 6.89 (s, 1H), 2.64 (s, 3H). $^{13}$C NMR (126 MHz, DMSO) δ 169.3, 168.6, 164.9, 155.2, 152.2, 142.2, 140.1, 135.4, 133.6, 133.2, 132.3, 131.5, 130.3, 130.1, 129.9, 128.1, 127.9, 125.7, 125.4, 123.0, 122.6, 121.2, 120.5, 20.3. HRMS (m/z): calcd for C$_{28}$H$_{19}$BrN$_3$O$_4$S$_3$ (M+H) 635.9721. found 637.9695.

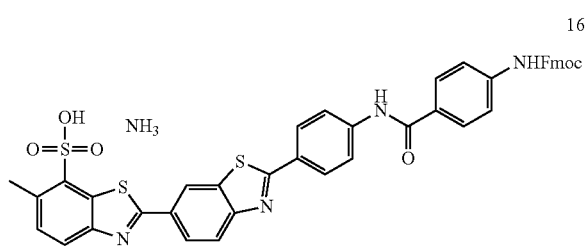

2'-(4-(4-((((9H-fluoren-9-yl)methoxy)carbonyl)amino)benzamido)phenyl)-6-methyl-[2,6'-bibenzo[d]thiazole]-7-sulfonic acid (16)

A suspension of 4-(((9H-fluoren-9-yl)methoxy)carbonylamino)benzoic acid (1 g, 2.78 mmol) in thionyl chloride (10 ml, 137 mmol) was refluxed for 2 hours. Solvents were removed under vacuum to give (9H-fluoren-9-yl)methyl 4-(chlorocarbonyl)phenylcarbamate (0.97 g, 92% yield) as a white solid. The material was used directly without purification. (9H-Fluoren-9-yl)methyl 4-(chlorocarbonyl)phenylcarbamate (12.1 mg, 0.033 mmol) was added to a solution of P2a (10 mg, 0.022 mmoL) in pyridine (1 mL) at 80° C. The reaction mixture was stirred at 80° C. overnight. The product was purified by reverse phase preparative HPLC.

Yield: 5.1 mg, 29%. $^1$H NMR (400 MHz, DMSO) δ 10.46 (s, 1H), 10.08 (s, 1H), 8.93 (d, J=2.3 Hz, 1H), 8.26 (dd, J=1.8, 8.6 Hz, 1H), 8.16 (d, J=8.8 Hz, 3H), 8.04 (d, J=8.9 Hz, 2H), 8.00-7.88 (m, 5H), 7.79 (d, J 7.4 Hz, 2H), 7.63 (s, br. 2H), 7.45 (t, J=7.2 Hz, 2H), 7.40-7.36 (m, 3H), 7.22 (s, 1H), 7.10 (s, 1H), 6.97 (s, 1H), 4.56 (d, J=6.5 Hz, 2H), 4.36 (d, J=6.6 Hz, 1H), 2.72 (s, 3H). $^{13}$C NMR (126 MHz, DMSO) δ 169.4, 168.6, 165.2, 155.2, 153.3, 152.2, 143.7, 142.6, 142.4, 140.8, 140.1, 135.4, 133.2, 132.3, 130.3, 130.1, 128.9, 128.12, 128.06, 127.7, 127.5, 127.1, 125.4, 125.1, 123.0, 122.6, 121.2, 120.3, 120.2, 117.4, 65.8, 46.5, 20.2. HRMS (m/z): calcd for $C_{43}H_{31}N_4O_6S_3$ (M+H) 795.1406. found 795.1381.

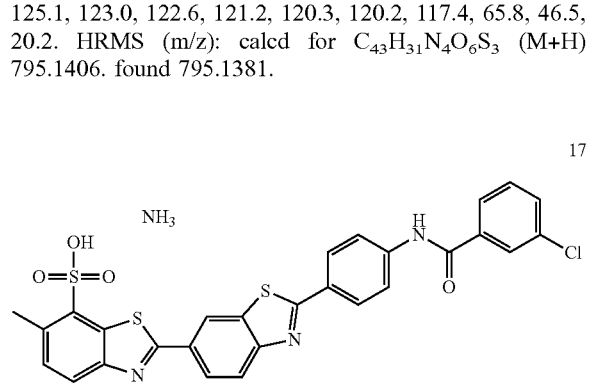

2'-(4-(3-chlorobenzamido)phenyl)-6-methyl-[2,6'-bibenzo[d]thiazole]-7-sulfonic acid (17)

Yield: 6.6 mg, 51% $^1$H NMR (500 MHz, DMSO) δ 10.69 (s, 1H), 8.93 (d, J=1.8 Hz, 1H), 8.26 (dd, J=1.8, 8.5 Hz, 1H), 8.18-8.15 (m, 3H), 8.08-8.01 (m, 3H), 7.97 (d, J=8.2 Hz, 1H), 7.91 (d, J=8.0 Hz, 1H), 7.74-7.67 (m, 1H), 7.61 (t, J=7.9 Hz, 1H), 7.38 (d, J=8.6 Hz, 1H), 7.19 (s, 1H), 7.09 (s, 1H), 6.99 (s, 1H), 2.71 (s, 3H). $^{13}$C NMR (126 MHz, DMSO) δ 169.3, 168.6, 164.4, 155.2, 152.2, 142.1, 140.1, 136.5, 135.4, 133.23, 133.17, 132.3, 131.7, 130.5, 130.3, 130.1, 128.1, 128.0, 127.5, 126.6, 125.4, 123.0, 122.6, 121.2, 120.5, 20.3. HRMS (m/z): calcd for $C_{28}H_{19}ClN_3O_4S_3$ (M+H) 592.0226. found 592.0228.

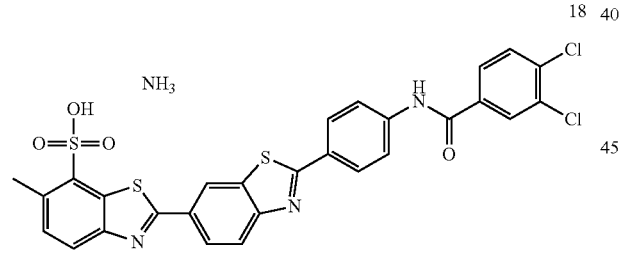

2'-(4-(3,4-dichlorobenzamido)phenyl)-6-methyl-[2,6'-bibenzo[d]thiazole]-7-sulfonic acid (18)

Yield: 12 mg, 87%. $^1$H NMR (500 MHz, DMSO) δ 10.71 (s, 1H), 8.92 (d, J=1.8 Hz, 1H), 8.30-8.21 (m, 2H), 8.17-8.14 (m, 3H), 8.02 (d, J=8.8 Hz, 2H), 7.98 (dd, J=2.1, 8.4 Hz, 1H), 7.90 (d, J=8.0 Hz, 1H), 7.84 (d, J=8.4 Hz, 1H), 7.38 (d, J 8.6 Hz, 1H), 7.20 (s, 1H), 7.10 (s, 1H), 7.00 (s, 1H), 2.71 (s, 3H). $^{13}$C NMR (126 MHz, DMSO) δ 169.2, 168.6, 163.5, 155.2, 152.2, 141.9, 140.1, 135.4, 134.8, 134.6, 133.2, 132.3, 131.3, 130.8, 130.3, 130.1, 129.7, 128.2, 128.09, 128.06, 125.4, 123.0, 122.6, 121.2, 120.5, 20.3. HRMS (m/z): calcd for $C_{28}H_{18}Cl_2N_3O_4S_3$ (M+H) 625.9836. found 625.9833.

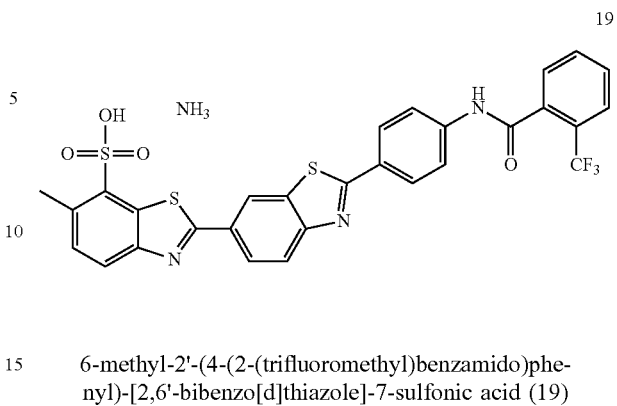

6-methyl-2'-(4-(2-(trifluoromethyl)benzamido)phenyl)-[2,6'-bibenzo[d]thiazole]-7-sulfonic acid (19)

Yield: 9.9 mg, 72%. $^1$H NMR (500 MHz, DMSO) δ 10.96 (s, 1H), 8.94 (d, J=1.8 Hz, 1H), 8.26 (dd, J=1.8, 8.5 Hz, 1H), 8.18-8.16 (m, 3H), 7.95-7.91 (m, 3H), 7.89 (d, J=7.9 Hz, 1H), 7.84 (t, J=7.4 Hz, 1H), 7.78-7.74 (m, 2H), 7.39 (d, J=8.5 Hz, 1H), 7.20 (s, 1H), 7.09 (s, 1H), 6.99 (s, 1H), 2.72 (s, 3H). $^{13}$C NMR (126 MHz, DMSO) δ 169.2, 168.6, 165.9, 155.2, 152.2, 141.9, 140.1, 135.78, 135.76, 135.4, 133.2, 132.7, 132.3, 130.33, 130.28, 130.1, 128.6, 128.3, 128.0, 126.44, 126.40, 126.37, 126.3, 125.9, 125.7, 125.4, 124.8, 123.1, 122.6, 121.2, 119.9, 20.3. HRMS (m/z): calcd for $C_{29}H_{19}F_3N_3O_4S_3$ (M+H) 626.0490. found 626.0497.

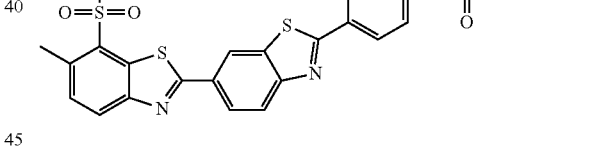

6-methyl-2'-(4-(3-(trifluoromethyl)benzamido)phenyl)-[2,6'-bibenzo[d]thiazole]-7-sulfonic acid (20)

Yield: 7.5 mg, 54%. $^1$H NMR (500 MHz, DMSO) δ 10.81 (s, 1H), 8.94 (d, J=1.5 Hz, 1H), 8.35 (s, 1H), 8.32 (d, J=7.9 Hz, 1H), 8.26 (dd, J=1.8, 8.5 Hz, 1H), 8.20-8.15 (m, 3H), 8.05 (d, J=8.8 Hz, 2H), 8.01 (d, J=7.8 Hz, 1H), 7.91 (d, J=8.0 Hz, 1H), 7.83 (t, J=7.8 Hz, 1H), 7.38 (d, J=8.6 Hz, 1H), 7.19 (s, 1H), 7.09 (s, 1H), 6.99 (s, 1H), 2.71 (s, 3H). $^{13}$C NMR (126 MHz, DMSO) δ 169.3, 168.6, 164.4, 155.2, 152.2, 142.0, 140.1, 135.5, 135.4, 133.2, 132.3, 132.0, 130.3, 130.1, 129.8, 129.3, 129.1, 128.4, 128.3, 128.2, 128.12, 128.07, 127.20, 127.15, 125.4, 125.0, 124.38, 124.35, 123.1, 122.9, 122.6, 121.2, 120.6, 20.2. HRMS (m/z): calcd for $C_{29}H_{19}F_3N_3O_4S_3$ (M+H) 626.0490. found 626.0492.

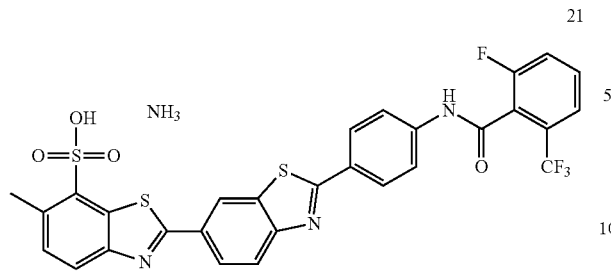

21

2'-(4-(2-fluoro-6-(trifluoromethyl)benzamido)phenyl)-6-methyl-[2,6'-bibenzo[d]thiazole]-7-sulfonic acid (21)

Yield: 1.8 mg, 13%. $^1$H NMR (500 MHz, DMSO) δ 11.21 (s, 1H), 8.95 (d, J=1.8 Hz, 1H), 8.26 (dd, J=1.8, 8.5 Hz, 1H), 8.19-8.16 (m, 3H), 7.92-7.88 (m, 3H), 7.85-7.73 (m, 3H), 7.38 (d, J=8.6 Hz, 1H), 7.19 (s, 1H), 7.08 (s, 1H), 6.98 (s, 1H), 2.71 (s, 3H). $^{13}$C NMR (126 MHz, DMSO) δ 169.1, 168.6, 160.6, 159.4, 157.5, 155.1, 152.2, 141.3, 140.2, 135.5, 133.2, 132.3, 132.2, 130.4, 130.1, 128.5, 128.4, 125.4, 124.1, 123.9, 123.1, 122.6, 121.2, 120.6, 120.4, 119.8, 20.2. HRMS (m/z): calcd for $C_{29}H_{18}F_4N_3O_4S_3$ (M+H) 644.0396. found 644.0407.

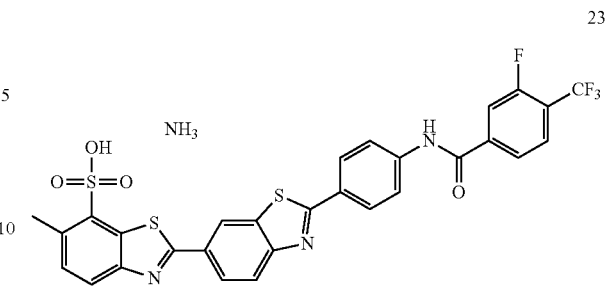

23

2'-(4-(3-fluoro-4-(trifluoromethyl)benzamido)phenyl)-6-methyl-[2,6'-bibenzo[d]thiazole]-7-sulfonic acid (23)

Yield: 6.4 mg, 45%. $^1$H NMR (500 MHz, DMSO) δ 10.83 (s, 1H), 8.93 (d, J=1.8 Hz, 1H), 8.25 (dd, J=1.8, 8.5 Hz, 1H), 8.19-8.15 (m, 3H), 8.11 (d, J=11.6 Hz, 1H), 8.04-7.99 (m, 4H), 7.90 (d, J=8.0 Hz, 1H), 7.38 (d, J=8.5 Hz, 1H), 7.19 (s, 1H), 7.09 (s, 1H), 6.99 (s, 1H), 2.71 (s, 3H). $^{13}$C NMR (126 MHz, DMSO) δ 169.2, 168.6, 163.3, 159.6, 157.6, 155.2, 152.2, 141.7, 141.12, 141.06, 140.1, 135.4, 133.2, 132.3, 130.4, 130.1, 128.3, 128.1, 127.80, 127.77, 125.6, 125.4, 124.5, 124.4, 123.4, 123.1, 122.6, 121.2, 120.6, 119.2, 119.1, 119.0, 118.9, 116.6, 116.4, 20.2. HRMS (m/z): calcd for $C_{29}H_{18}F_4N_3O_4S_3$ (M+H) 644.0396. found 644.0381.

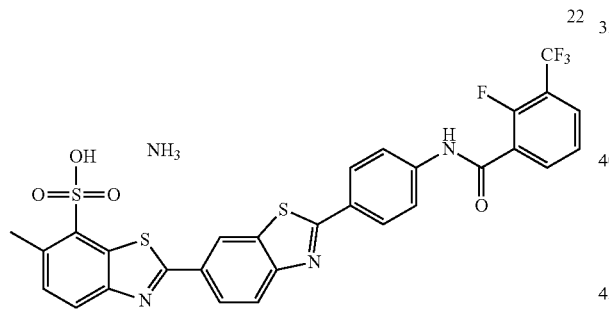

22

2'-(4-(2-fluoro-3-(trifluoromethyl)benzamido)phenyl)-6-methyl-[2,6'-bibenzo[d]thiazole]-7-sulfonic acid (22)

Yield: 8.5 mg, 60%. $^1$H NMR (500 MHz, DMSO) δ 11.02 (s, 1H), 8.94 (d, J=1.8 Hz, 1H), 8.26 (dd, J=1.8, 8.5 Hz, 1H), 8.20-8.16 (m, 3H), 8.07 (t, J=6.5 Hz, 1H), 8.00 (t, J=7.4 Hz, 1H), 7.96 (d, J=8.7 Hz, 2H), 7.91 (d, J=8.0 Hz, 1H), 7.58 (t, J=7.8 Hz, 1H), 7.38 (d, J=8.6 Hz, 1H), 7.19 (s, 1H), 7.09 (s, 1H), 6.99 (s, 1H), 2.71 (s, 3H). $^{13}$C NMR (126 MHz, DMSO) δ 169.2, 168.6, 161.7, 156.9, 155.2, 154.8, 152.2, 141.6, 140.1, 135.4, 134.7, 133.2, 132.3, 130.4, 130.1, 129.4, 128.31, 128.28, 126.4, 126.3, 125.7, 125.3, 125.2, 123.5, 123.1, 122.6, 121.4, 121.2, 120.1, 117.3, 117.2, 117.1, 117.0, 20.3. HRMS (m/z): calcd for $C_{29}H_{18}F_4N_3O_4S_3$ (M+H) 644.0396. found 644.0389.

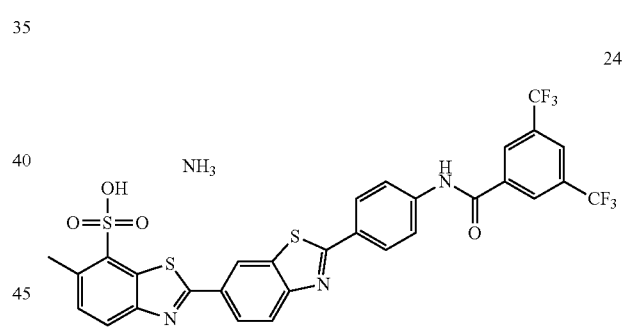

24

2'-(4-(3,5-bis(trifluoromethyl)benzamido)phenyl)-6-methyl-[2,6'-bibenzo[d]thiazole]-7-sulfonic acid (24)

Yield: 10.1 mg, 66%. $^1$H NMR (500 MHz, DMSO) δ 10.96 (s, 1H), 8.94 (d, J=2.2 Hz, 1H), 8.66 (s, 2H), 8.41 (s, 1H), 8.26 (dd, J=1.8, 8.5 Hz, 1H), 8.21 (d, J=8.8 Hz, 2H), 8.16 (d, J=8.7 Hz, 1H), 8.04 (d, J=8.8 Hz, 2H), 7.91 (d, J=8.0 Hz, 1H), 7.38 (d, J=8.5 Hz, 1H), 7.19 (s, 1H), 7.09 (s, 1H), 6.99 (s, 1H), 2.71 (s, 3H). $^{13}$C NMR (126 MHz, DMSO) δ 169.2, 168.6, 162.9, 155.2, 152.2, 141.6, 140.1, 136.8, 135.4, 133.2, 132.3, 130.9, 130.6, 130.4, 130.3, 130.13, 130.06, 128.7, 128.4, 128.2, 126.4, 125.4, 124.2, 123.1, 122.6, 122.0, 121.2, 120.7, 20.2. HRMS (m/z): calcd for $C_{30}H_{18}F_6N_3O_4S_3$ (M+H) 694.0364. found 694.0340.

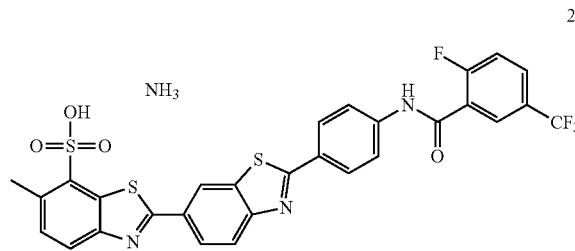

2'-(4-(2-fluoro-5-(trifluoromethyl)benzamido)phenyl)-6-methyl-[2,6'-bibenzo[d]thiazole]-7-sulfonic acid (25)

Yield: 9.5 mg, 67%. $^1$H NMR (500 MHz, DMSO) δ 10.98 (s, 1H), 8.94 (d, J=1.8 Hz, 1H), 8.26 (dd, J=1.8, 8.5 Hz, 1H), 8.22-8.12 (m, 4H), 8.05-8.02 (m, 1H), 7.96 (d, J 8.7 Hz, 2H), 7.91 (d, J=8.0 Hz, 1H), 7.66 (t, J=9.1 Hz, 1H), 7.39 (d, J=8.6 Hz, 1H), 7.19 (s, 1H), 7.09 (s, 1H), 6.99 (s, 1H), 2.71 (s, 3H). $^{13}$C NMR (126 MHz, DMSO) δ 169.2, 168.6, 162.0, 161.6, 159.9, 155.2, 152.2, 141.6, 140.1, 135.4, 133.2, 132.3, 130.4, 130.1, 128.29, 128.25, 127.5, 125.7, 125.5, 125.4, 125.31, 125.29, 124.6, 123.1, 122.6, 122.4, 121.2, 120.1, 117.8, 117.6, 20.2. HRMS (m/z): calcd for $C_{29}H_{18}F_4N_3O_4S_3$ (M+H) 644.0396. found 644.0405.

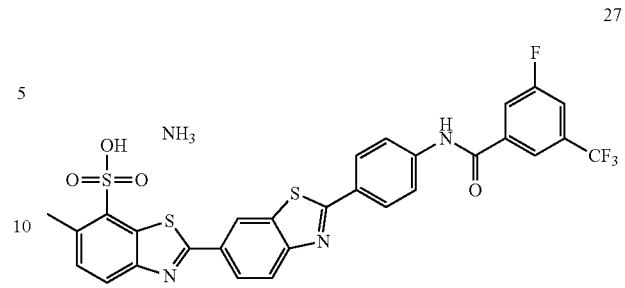

2'-(4-(3-fluoro-5-(trifluoromethyl)benzamido)phenyl)-6-methyl-[2,6'-bibenzo[d]thiazole]-7-sulfonic acid (27)

Yield: 6.9 mg, 49%. $^1$H NMR (500 MHz, DMSO) δ 10.83 (s, 1H), 8.94 (d, J=1.7 Hz, 1H), 8.26 (dd, J=1.8, 8.5 Hz, 1H), 8.24-8.13 (m, 5H), 8.04-8.00 (m, 3H), 7.91 (d, J=8.0 Hz, 1H), 7.38 (d, J=8.6 Hz, 1H), 7.19 (s, 1H), 7.09 (s, 1H), 6.99 (s, 1H), 2.71 (s, 3H). $^{13}$C NMR (126 MHz, DMSO) δ 169.2, 168.6, 163.0, 162.8, 160.9, 155.2, 152.2, 141.7, 140.1, 138.1, 138.0, 135.4, 133.2, 132.3, 131.32, 131.25, 131.1, 131.0, 130.4, 130.1, 128.3, 128.2, 125.4, 124.2, 123.1, 122.6, 122.0, 121.2, 120.74, 120.67, 119.3, 119.1, 116.2, 116.1, 20.2. HRMS (m/z): calcd for $C_{29}H_{18}F_4N_3O_4S_3$ (M+H) 644.0396. found 644.0374.

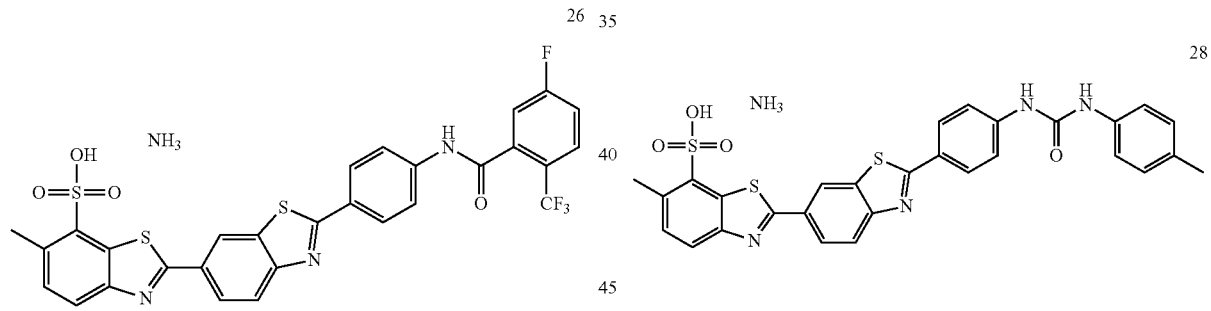

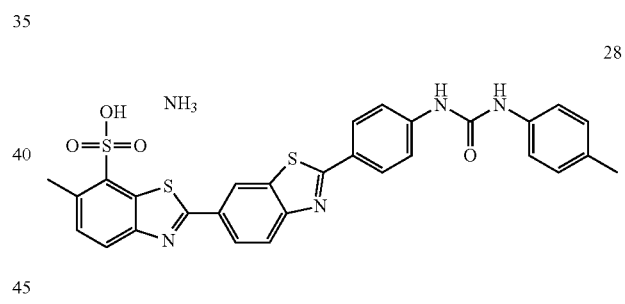

2'-(4-(5-fluoro-2-(trifluoromethyl)benzamido)phenyl)-6-methyl-[2,6'-bibenzo[d]thiazole]-7-sulfonic acid (26)

Yield: 8.6 mg, 61%. $^1$H NMR (400 MHz, DMSO) δ 11.01 (s, 1H), 8.94 (d, J=1.8 Hz, 1H), 8.26 (dd, J=1.8, 8.5 Hz, 1H), 8.20-8.16 (m, 3H), 7.99 (dd, J=5.1, 8.9 Hz, 1H), 7.94-7.91 (m, 3H), 7.81 (d, J=6.1 Hz, 1H), 7.62 (t, J=8.3 Hz, 1H), 7.39 (d, J=8.6 Hz, 1H), 7.22 (s, 1H), 7.09 (s, 1H), 6.96 (s, 1H), 2.72 (s, 3H). $^{13}$C NMR (126 MHz, DMSO) δ 169.2, 168.6, 164.6, 164.3, 162.6, 155.2, 152.2, 141.7, 140.1, 138.5, 138.4, 135.4, 133.2, 132.3, 130.4, 130.1, 129.7, 129.63, 129.59, 129.56, 128.3, 128.2, 125.4, 124.5, 123.1, 122.6, 122.5, 122.30, 122.26, 121.2, 119.9, 117.3, 117.1, 116.4, 116.2, 20.2. HRMS (m/z): calcd for $C_{29}H_{18}F_4N_3O_4S_3$ (M+H) 644.0396. found 644.0413.

6-methyl-2'-(4-(3-(p-tolyl)ureido)phenyl)-[2,6'-bibenzo[d]thiazole]-7-sulfonic acid (28)

To a solution of P2a (10 mg, 0.022 mmol) in DMF (1 mL) at 80° C., was added phenyl isocyanate (28 μL, 0.22 mmol, 10 equiv.). The reaction mixture was stirred at 80° C. overnight. The product was isolated via reverse phase preparative HPLC. Yield: 3.3 mg, 26%. $^1$H NMR (400 MHz, DMSO) δ 9.09 (s, 1H), 8.91 (d, J=1.8 Hz, 1H), 8.72 (s, 1H), 8.27-8.21 (m, 1H), 8.13 (d, J=8.5 Hz, 1H), 8.08 (d, J=8.8 Hz, 2H), 7.91 (d, J=8.0 Hz, 1H), 7.69 (d, J=8.8 Hz, 2H), 7.39 7.37 (m, 3H), 7.21 (s, 1H), 7.12 (d, J=8.4 Hz, 2H), 7.09 (s, 1H), 6.96 (s, 1H), 2.72 (s, 3H), 2.27 (s, 3H). $^{13}$C NMR (101 MHz, DMSO) δ 169.5, 168.6, 155.3, 152.2, 152.2, 143.3, 140.2, 136.8, 135.3, 133.1, 132.3, 131.0, 130.1, 129.2, 128.4, 125.9, 125.3, 122.8, 122.6, 121.1, 118.5, 118.1, 20.34, 20.25. HRMS (m/z): calcd for $C_{29}H_{23}N_4O_4S_3$ (M+H) 587.0881. found 587.0875.

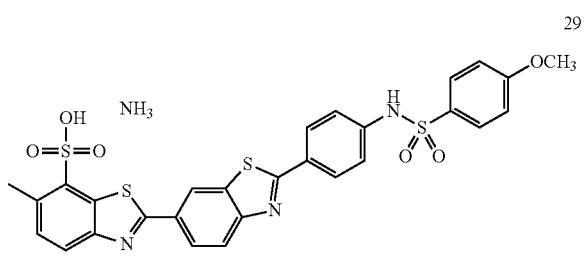

2'-(4-(4-methoxyphenylsulfonamido)phenyl)-6-methyl-[2,6'-bibenzo[d]thiazole]-7-sulfonic acid (29)

To a solution of P2a (10 mg, 0.022 mmoL) in pyridine (1 mL) at 80° C., was added 4-methoxybenzenesulfonyl chloride (10.3 mg, 0.033 mmol, 1.5 equiv.). The reaction mixture was stirred at 80° C. overnight. Half of the crude material was purified by reverse phase combiflash. Yield: 4.2 mg, 41%. $^1$H NMR (500 MHz, DMSO) δ 8.90 (d, J=1.8 Hz, 1H), 8.23 (dd, J=1.8, 8.6 Hz, 1H), 8.11 (d, J=8.7 Hz, 1H), 8.02 (d, J=8.8 Hz, 2H), 7.90 (d, J=8.1 Hz, 1H), 7.79 (d, J=9.0 Hz, 2H), 7.37 (d, J=8.6 Hz, 1H), 7.30 (d, J=8.8 Hz, 2H), 7.10 (d, J=9.0 Hz, 2H), 3.80 (s, 3H), 2.70 (s, 3H). $^{13}$C NMR (126 MHz, DMSO) δ 169.0, 168.5, 162.6, 155.1, 152.1, 141.3, 140.1, 135.4, 133.2, 132.3, 130.9, 130.3, 130.1, 128.9, 128.6, 127.6, 125.4, 123.0, 122.6, 121.2, 119.1, 114.5, 55.6, 20.2. HRMS (m/z): calcd for $C_{28}H_{22}N_3O_6S_4$ (M+H) 624.0391. found 624.0378.

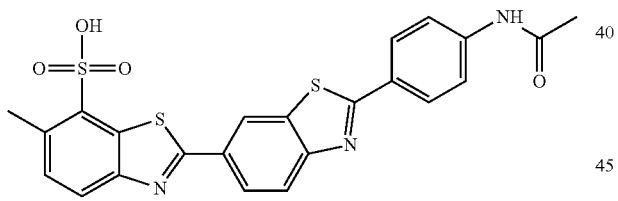

2'-(4-acetamidophenyl)-6-methyl-[2,6'-bibenzo[d]thiazole]-7-sulfonic acid (30)

To a suspension of P2a (40 mg, 0.088 mmol) in DMA (1 mL), was added thionyl chloride (0.013 ml, 0.176 mmol) dropwise. The reaction mixture was stirred at 80° C. for 16 hours. The product was purified by RP preparative HPLC. Yield: 31.7 mg, 73%. $^1$H NMR (400 MHz, DMSO) δ 10.32 (s, 1H), 8.92 (d, J=1.8, 1H), 8.25 (dd, J=1.8, 8.6, 1H), 8.14 (d, J=9.0, 1H), 8.10 (d, J=8.8, 2H), 7.91 (d, J=8.0, 1H), 7.82 (d, J=8.8, 2H), 7.38 (d, J=8.7, 1H), 7.22 (s, 1H), 7.09 (s, 1H), 6.96 (s, 1H), 2.72 (s, 3H), 2.12 (s, 3H). $^{13}$C NMR (126 MHz, DMSO) δ 169.4, 168.8, 168.6, 155.2, 152.2, 142.5, 140.1, 135.3, 133.1, 132.3, 130.2, 130.1, 128.2, 127.1, 125.4, 123.0, 122.6, 121.2, 119.1, 24.2, 20.2. HRMS (m/z): calcd for $C_{23}H_{18}N_3O_4S_3$ (neutral M+H) 496.0459. found 496.0457.

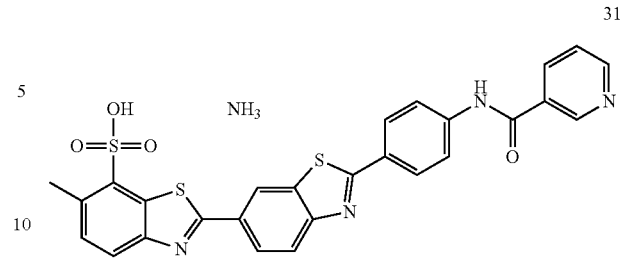

6-methyl-2'-(4-(nicotinamido)phenyl)-[2,6'-bibenzo[d]thiazole]-7-sulfonic acid (31)

Yield: 14.8 mg, 100%. $^1$H NMR (400 MHz, DMSO) δ 10.75 (s, 1H), 9.13 (d, J 2.2 Hz, 1H), 8.85 (d, J=1.8 Hz, 1H), 8.77 (dd, J=1.8, 5.0 Hz, 1H), 8.44-8.35 (m, 1H), 8.18 (dd, J=1.8, 8.5 Hz, 1H), 8.11-8.07 (m, 3H), 8.00-7.90 (m, 2H), 7.84 (d, J=8.0 Hz, 1H), 7.68-7.57 (m, 1H), 7.31 (d, J=8.6 Hz, 1H), 7.15 (s, 1H), 7.02 (s, 1H), 6.90 (s, 1H), 2.65 (s, 3H). $^{13}$C NMR (126 MHz, DMSO) δ 169.2, 168.6, 164.0, 155.2, 152.2, 151.2, 147.9, 141.9, 140.1, 136.8, 135.4, 133.2, 132.3, 130.7, 130.3, 130.1, 128.14, 128.08, 125.4, 124.0, 123.0, 122.6, 121.2, 120.4, 20.3. HRMS (m/z): calcd for $C_{27}H_{19}N_4O_4S_3$ (M+H) 559.0568. found 559.0579.

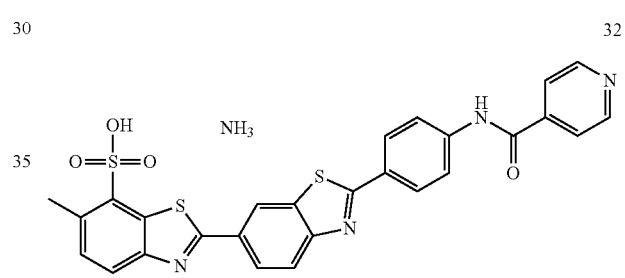

2'-(4-(isonicotinamido)phenyl)-6-methyl-[2,6'-bibenzo[d]thiazole]-7-sulfonic acid (32)

Yield: 2.4 mg, 20%. $^1$H NMR (500 MHz, DMSO) δ 10.9 (s, 1H), 8.94 (d, J=1.7 Hz, 1H), 8.87 (d, J=6.2 Hz, 2H), 8.31-8.23 (m, 1H), 8.20 (d, J=8.9 Hz, 2H), 8.16 (d, J=8.7 Hz, 1H), 8.04 (d, J=8.9 Hz, 2H), 7.99 (d, J=6.2 Hz, 2H), 7.91 (d, J=8.3 Hz, 1H), 7.38 (d, J=8.3 Hz, 1H), 7.18 (s, 1H), 7.08 (s, 1H), 6.98 (s, 1H), 2.71 (s, 3H). $^{13}$C NMR (126 MHz, DMSO) δ 169.2, 168.6, 164.0, 155.2, 152.1, 149.4, 141.7, 140.2, 135.5, 133.2, 132.3, 130.4, 130.1, 128.3, 128.2, 125.4, 123.1, 122.6, 122.1, 121.2, 120.6, 20.2. HRMS (m/z): calcd for $C_{27}H_{19}N_4O_4S_3$ (M+H) 559.0568. found 559.0576.

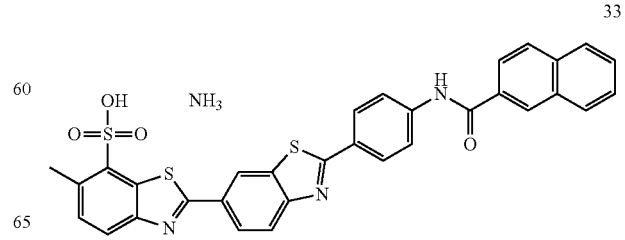

2'-(4-(2-naphthamido)phenyl)-6-methyl-[2,6'-bibenzo[d]thiazole]-7-sulfonic acid (33)

Yield: 5.6 mg, 42%. $^1$H NMR (500 MHz, DMSO) δ 10.79 (s, 1H), 8.94 (d, J=1.8 Hz, 1H), 8.65 (s, 1H), 8.26 (dd, J=1.8, 8.5 Hz, 1H), 8.20-8.16 (m, 3H), 8.15-8.02 (m, 6H), 7.91 (d, J=8.0 Hz, 1H), 7.69-7.64 (m, 2H), 7.39 (d, J=8.5 Hz, 1H), 7.19 (s, 1H), 7.09 (s, 1H), 6.99 (s, 1H), 2.72 (s, 3H). $^{13}$C NMR (126 MHz, DMSO) δ 169.4, 168.6, 165.9, 155.2, 152.2, 142.5, 140.1, 135.4, 134.4, 133.2, 132.3, 132.0, 131.9, 130.3, 130.1, 129.0, 128.2, 128.13, 128.10, 128.0, 127.8, 127.7, 126.9, 125.4, 124.4, 123.0, 122.6, 121.2, 120.4, 20.3. HRMS (m/z): calcd for $C_{32}H_{22}N_3O_4S_3$ (M+H) 608.0772. found 608.0760.

34

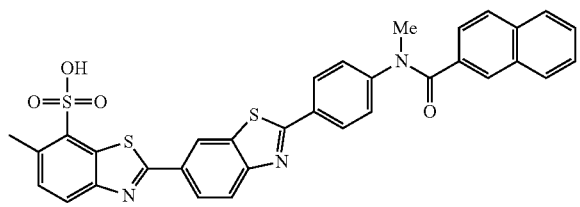

6-methyl-2'-(4-(N-methyl-2-naphthamido)phenyl)-[2,6'-bibenzo[d]thiazole]-7-sulfonic acid (34)

To a suspension of sodium hydride (1.7 mg, 0.041 mmol) in DMF (Volume: 2 ml), was added 2'-(4-(2-naphthamido)phenyl)-6-methyl-2,6'-bibenzo[d]thiazole-7-sulfonic acid (0.010 g, 0.016 mmol) at 0° C. After 2 hours, iodomethane (1.5 μl, 0.025 mmol) was added. The mixture was allowed to stir at room temperature for 16 hours. The product was isolated via reverse phase preparative HPLC. Yield: 7.6 mg, 74%. $^1$H NMR (500 MHz, DMSO) δ 8.90 (d, J=1.7 Hz, 1H), 8.23 (dd, J=1.8, 8.6 Hz, 1H), 8.12 (d, J=8.5 Hz, 1H), 8.01-7.99 (m, 3H), 7.90-7.85 (m, 3H), 7.79 (d, J=8.6 Hz, 1H), 7.58-7.48 (m, 2H), 7.42 (d, J=8.6 Hz, 2H), 7.41-7.37 (m, 2H), 3.52 (s, 3H), 2.70 (s, 3H). $^{13}$C NMR (126 MHz, DMSO) δ 169.5, 168.6, 168.5, 155.0, 152.1, 147.4, 140.1, 135.6, 133.4, 133.2, 133.1, 132.3, 131.9, 130.5, 130.1, 128.6, 128.4, 128.0, 127.6, 127.4, 126.7, 125.4, 125.2, 123.3, 122.6, 121.3, 120.6, 112.4, 111.9, 37.7, 20.2. HRMS (m/z): calcd for $C_{33}H_{24}N_3O_4S_3$ (M+H) 622.0929. found 622.0898.

Tetramer Analogs.

The general procedure for tetramer analogs is shown in Scheme 2.

SCHEME 2

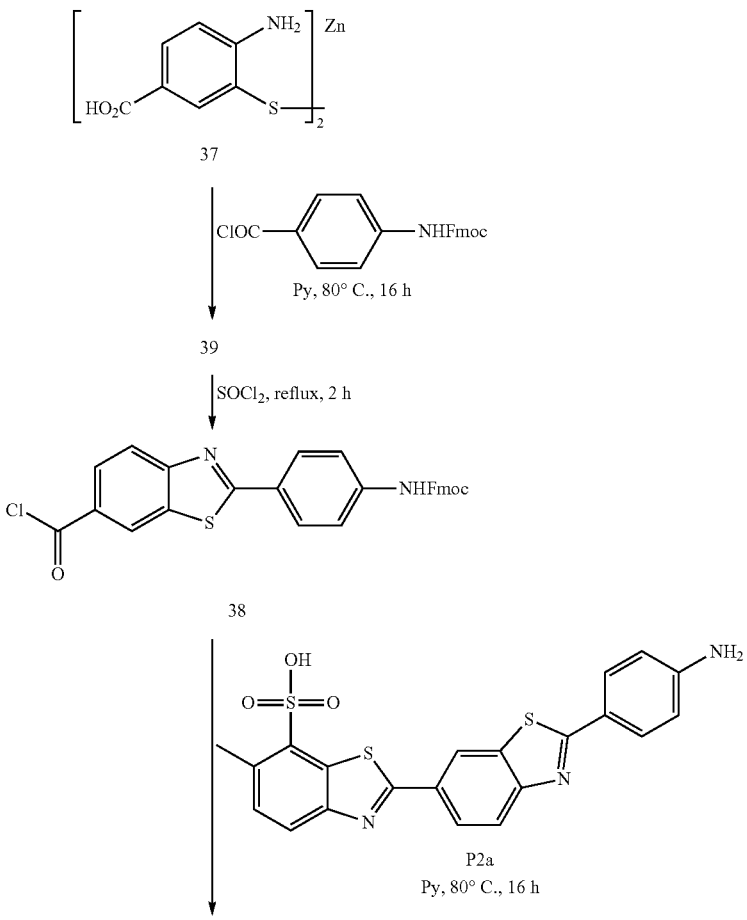

-continued

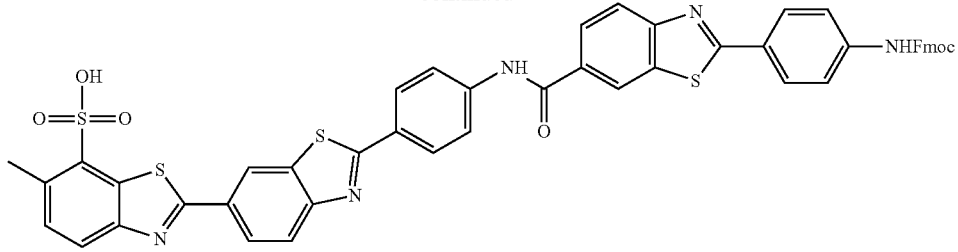

36

Morpholine
DMF, rt, 16 h

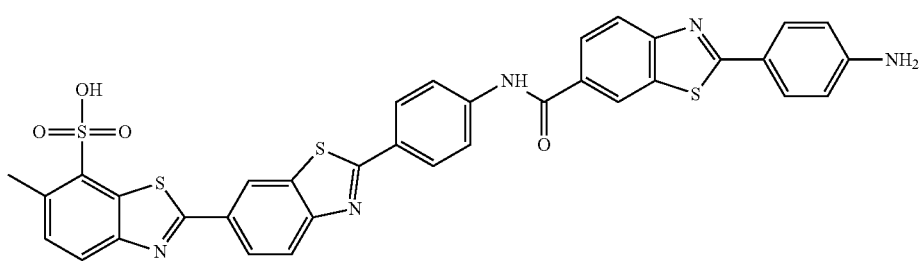

35

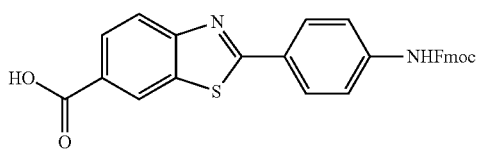

2-(4-(M9H-fluoren-9-yl)methoxy)carbonyl)amino)
phenyl)benzo[d]thiazole-6-carboxylic acid (39)

To a suspension of zinc salt 37 (Wu et al. (2007) *Bioorg. Med. Chem.* 15:2789-2796) (266 mg, 0.66 mmol) in pyridine (5 mL) at 80° C., was added (9H-fluoren-9-yl)methyl (4-(chlorocarbonyl)phenyl)carbamate (500 mg, 1.32 mmol), which was prepared from 4-((((9H-fluoren-9-yl)methoxy)carbonyl)amino)benzoic acid refluxed with SOCl$_2$ for 2 hours. The reaction mixture was stirred at 80° C. for hours. The resulting residue after evaporation was purified by reverse phase HPLC. Yield: 196 mg, 30%. $^1$H NMR (400 MHz, DMSO) δ 10.15 (s, 1H), 8.74 (s, 1H), 8.07-8.05 (m, 4H), 7.93 (d, J=7.5 Hz, 2H), 7.78 (d, J=7.5 Hz, 2H), 7.69 (s, br. 2H), 7.45 (t, J=7.3 Hz, 2H), 7.37 (t, J=7.3 Hz, 2H), 4.56 (d, J=6.5 Hz, 2H), 4.36 (d, J=6.5 Hz, 1H). $^{13}$C NMR (101 MHz, DMSO) δ 170.5, 166.9, 156.4, 153.2, 143.7, 142.5, 140.8, 134.4, 128.4, 127.7, 127.5, 127.4, 127.1, 126.6, 125.1, 124.2, 122.2, 120.2, 118.4, 65.8, 46.6. HRMS (m/z): calcd for C$_{29}$H$_{21}$N$_2$O$_4$S (neutral M+H) 493.1222. found 493.1221.

2'-(4-(2-(4-(M9H-fluoren-9-yl)methoxy)carbonyl)amino)phenyl)benzo[d]thiazole-6-carboxamido)phenyl)-6-methyl-[2,6'-bibenzo[d]thiazole]-7-sulfonic acid (36)

To a solution of P2a (113.3 mg, 0.25 mmoL) in pyridine (4 mL) at 80° C., was added (9H-fluoren-9-yl)methyl (4-(6-(chlorocarbonyl)benzo[d]thiazol-2-yl)phenyl) (38) (127.6 mg, 0.25 mmol) obtained via treating 39 with SOCl$_2$ under refluxing for 2 hours. The reaction mixture was stirred at 80° C. overnight. Solvents were removed, and the residue was purified by reverse phase preparative HPLC. Yield: 5.5 mg, 2.4%. 1H NMR (400 MHz, DMSO) δ 10.75 (s, 1H), 10.15 (s, 1H), 8.94 (d, J=2.3 Hz, 1H), 8.78 (s, 1H), 8.31-8.23 (m, 1H), 8.20-8.15 (m, 4H), 8.10-8.07 (m, 4H), 7.98-7.88 (m, 3H), 7.79 (d, J=7.4 Hz, 2H), 7.70 (s, br. 2H), 7.46 (t, J=7.2 Hz, 2H), 7.40-7.37 (m, 3H), 7.22 (s, 1H), 7.09 (s, 1H), 6.97 (s, 1H), 4.56 (d, J=6.5 Hz, 2H), 4.36 (t, J=6.5 Hz, 1H), 2.72 (s, 3H). 13C NMR (126 MHz, DMSO) δ 170.0, 169.3, 168.6, 165.3, 155.7, 155.2, 153.2, 152.2, 143.7, 142.5, 142.4, 140.8, 140.1, 135.4, 134.3, 133.2, 132.3, 131.2, 130.3, 130.1, 128.4, 128.1, 127.8, 127.7, 127.2, 126.6, 126.4, 125.4, 125.1, 123.0, 122.6, 122.4, 122.2, 121.2, 120.4, 120.2, 118.4, 65.8, 46.6, 20.3. HRMS (m/z): calcd for C$_{50}$H$_{34}$N$_5$O$_6$S$_4$ (neutral M+H) 928.1392. found 928.1381.

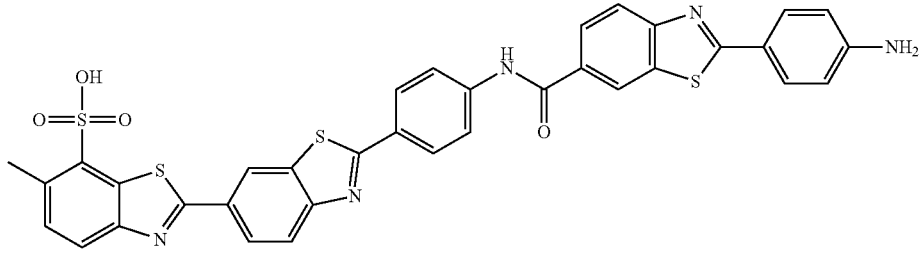

2'-(4-(2-(4-aminophenyl)benzo[d]thiazole-6-carboxamido)phenyl)-6-methyl-[2,6'-bibenzo[d]thiazole]-7-sulfonic acid (35)

To a solution of P2a (50.6 mg, 0.11 mmoL) in pyridine (4 mL) at 80° C., was added 38 (57 mg, 0.11 mmol). The reaction mixture was stirred at 80° C. overnight. Solvents were removed, and the residue was dissolved in DMF (10 mL). Morpholine (42 μL, 0.48 mmol) was added. The mixture was stirred at room temperature for 16 hours. The product was purified by reverse phase preparative HPLC. Yield: 1.5 mg, 1.9% (2 steps). $^1$H NMR (400 MHz, DMSO) δ 10.70 (s, 1H), 8.94 (s, 1H), 8.70 (s, 1H), 8.26 (m, 1H), 8.20-8.16 (m, 3H), 8.09-8.07 (m, 3H), 8.03 (d, J=8.5 Hz, 1H), 7.92 (d, J=8.1 Hz, 2H), 7.83 (d, J=8.6 Hz, 2H), 7.39 (d, J=8.3 Hz, 1H), 6.70 (d, J=8.7 Hz, 2H), 6.04 (s, 1H), 2.72 (s, 3H). $^{13}$C NMR (126 MHz, DMSO) δ 171.2, 169.4, 168.6, 165.4, 156.1, 155.2, 152.7, 152.2, 142.5, 140.1, 135.4, 133.7, 133.2, 132.3, 130.3, 130.3, 130.1, 129.2, 128.1, 127.7, 126.2, 125.4, 123.0, 122.6, 122.0, 121.3, 121.2, 120.4, 119.6, 113.6, 20.2. HRMS (m/z): calcd for $C_{35}H_{24}N_5O_4S_4$ (M+H) 706.0711. found 706.0698.

Example 6

Analysis of HCV NS3 Helicase Inhibitors Using Binding Assay

The *Escherichia coli* SSB assay was performed in a total volume of 20.2 μl in 384-well, flat-bottom, low volume, black microplates (Greiner Bio-One). First, 20 μl of a assay solution (5 nM Cy5-TTTTTTTTTTTTTTT-3' (Cy5-dT$_{15}$, SEQ ID NO:5), 20 nM *E. coli* SSB (Promega), 25 mM MOPS, pH 7.5, 1.25 mM MgCl$_2$, 0.0025 mg/ml BSA, 0.005% (v/v) TWEEN 20 and 0.025 mM DTT) was dispensed in each well, then 0.2 μl of dimethylsulfoxide (DMSO) or compound dissolved in DMSO was added by pin transfer, such that the final concentration of DMSO was 1% (v/v) in each assay.

For IC$_{50}$ determination, assays were performed with 60 μl total volume in black flat bottomed 384-well microplates (Corning). First, 3.0 μl of DMSO or compound dissolved in DMSO was added, such that the final concentration of DMSO was 5% (v/v) in each assay. Then 57 μl of a assay solution (5 nM Cy5-dT$_{15}$, 20 nM SSB, 25 mM MOPS, pH

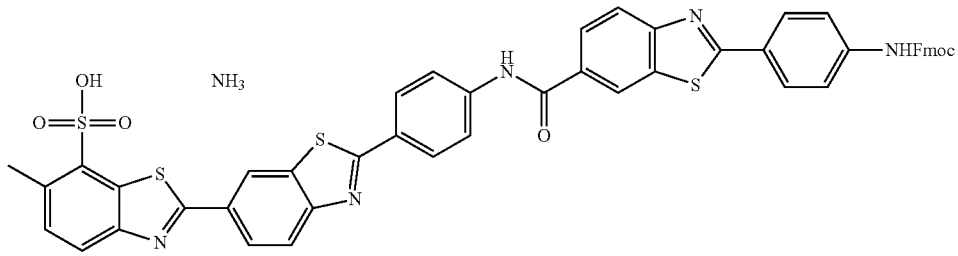

$^1$H NMR (400 MHz, DMSO) δ 10.75 (s, 1H), 10.15 (s, 1H), 8.94 (d, J=2.3 Hz, 1H), 8.78 (s, 1H), 8.31-8.23 (m, 1H), 8.20-8.15 (m, 4H), 8.10-8.07 (m, 4H), 7.98-7.88 (m, 3H), 7.79 (d, J=7.4 Hz, 2H), 7.70 (s, br. 2H), 7.46 (t, J=7.2 Hz, 2H), 7.40-7.37 (m, 3H), 7.22 (s, 1H), 7.09 (s, 1H), 6.97 (s, 1H), 4.56 (d, J=6.5 Hz, 2H), 4.36 (t, J=6.5 Hz, 1H), 2.72 (s, 3H). $^{13}$C NMR (126 MHz, DMSO) δ 170.0, 169.3, 168.6, 165.3, 155.7, 155.2, 153.2, 152.2, 143.7, 142.5, 142.4, 140.8, 140.1, 135.4, 134.3, 133.2, 132.3, 131.2, 130.3, 130.1, 128.4, 128.1, 127.8, 127.7, 127.2, 126.6, 126.4, 125.4, 125.1, 123.0, 122.6, 122.4, 122.2, 121.2, 120.4, 120.2, 118.4, 65.8, 46.6, 20.3. HRMS (m/z): calcd for $C_{50}H_{34}N_5O_6S_4$ (M+H) 928.1392. found 928.1381.

7.5, 1.25 mM MgCl$_2$, 0.0025 mg/ml BSA, 0.005% (v/v) TWEEN 20 and 0.025 mM DTT) was dispensed in each well. Polarization was monitored with a TECAN Infinite M1000 PRO multi-mode microplate reader by exciting at 635 nm (5 nm bandwidth) and measuring total fluorescence intensity, parallel and perpendicular polarized light at 667 nm (20 nm bandwidth).

As demonstrated herein, Thioflavine S, primuline and related derivatives inhibit HCV helicase in an MBHA-based screen of the NCI Mechanistic Set of compounds. Therefore, the entire primuline derivative collection was screened for more specific compounds. To this end, the ability of the compounds synthesized from the main component of primuline to disrupt the Cy5-dT$_{15}$-SSB complex were compared with their ability to inhibit the HCV helicase in a standard HCV helicase MBHA (Table 9).

TABLE 9

| Cmpd | Structure | DNA Unwinding IC$_{50}$, μM | Cy5-dT$_{15}$-SSB Binding IC$_{50}$, μM |
|---|---|---|---|
| 17 | 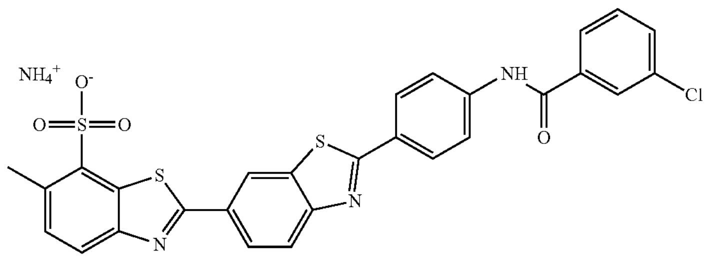 [SMILES: Cc1ccc2nc(-c3ccc4nc(-c5ccc(NC(=O)c6cccc(Cl)c6)cc5)sc4c3)sc2c1S(=O)(=O)[O-] ; [NH4+]] | 3 ± 1 | 201 ± 119 |
| 16 | 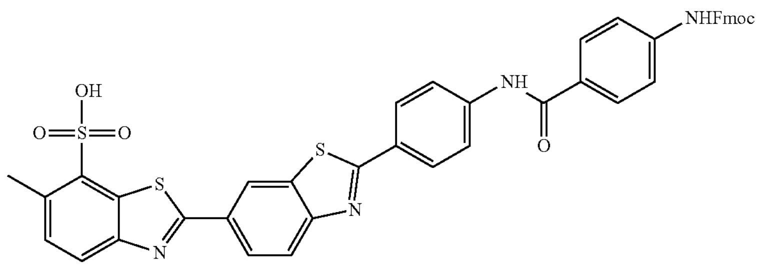 | 5 ± 1 | 179 ± 239 |
| 31 | 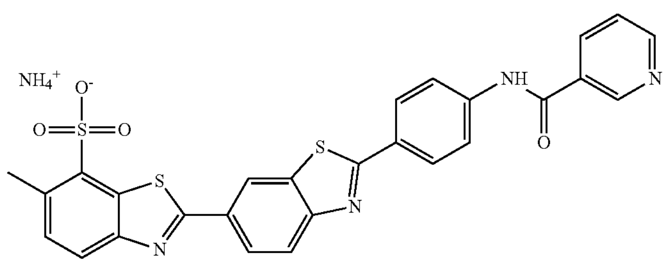 | 22 ± 2 | 173 ± 354 |
| 18 | 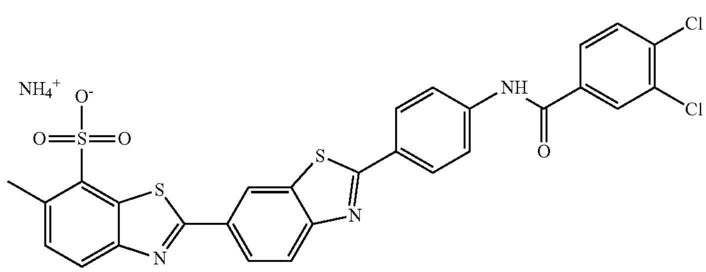 [SMILES: Cc1ccc2nc(-c3ccc4nc(-c5ccc(NC(=O)c6ccc(Cl)c(Cl)c6)cc5)sc4c3)sc2c1S(=O)(=O)[O-] ; [NH4+]] | 4 ± 1 | 128 ± 57 |
| 22 | 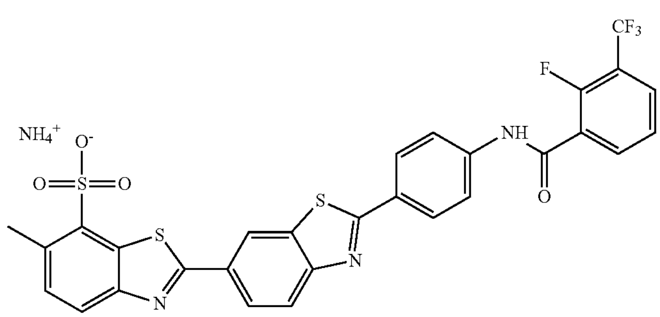 [SMILES: Cc1ccc2nc(-c3ccc4nc(-c5ccc(NC(=O)c6cccc(C(F)(F)F)c6F)cc5)sc4c3)sc2c1S(=O)(=O)[O-] ; [NH4+]] | 9 ± 3 | 71 ± 13 |

TABLE 9-continued

| Cmpd | Structure | DNA Unwinding IC$_{50}$, μM | Cy5-dT$_{15}$-SSB Binding IC$_{50}$, μM |
|---|---|---|---|
| 40 | 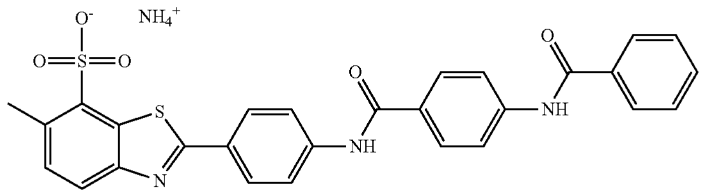 [SMILES: [NH4+] ; Cc1ccc2nc(-c3ccc(NC(=O)c4ccc(NC(=O)c5ccccc5)cc4)cc3)sc2c1S(=O)(=O)[O-]] | 81 ± 22 | 57 ± 13 |
| 41 | 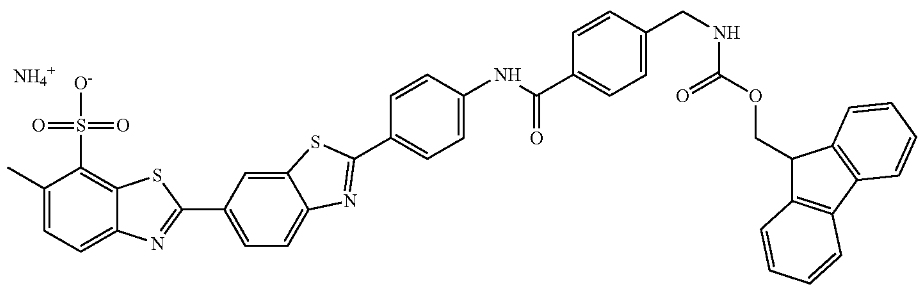 [SMILES: Cc1ccc2nc(-c3ccc4nc(-c5ccc(NC(=O)c6ccc(CNC(=O)OCC7c8ccccc8-c8ccccc87)cc6)cc5)sc4c3)sc2c1S(=O)(=O)[O-] ; [NH4+]] | 4 ± 0 | 57 ± 16 |
| 32 | 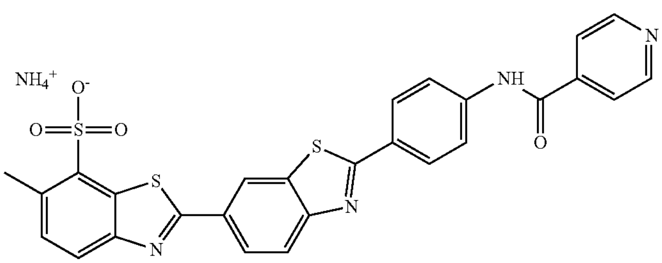 [SMILES: Cc1ccc2nc(-c3ccc4nc(-c5ccc(NC(=O)c6ccncc6)cc5)sc4c3)sc2c1S(=O)(=O)[O-] ; [NH4+]] | 52 ± 20 | 55 ± 20 |
| 10 | 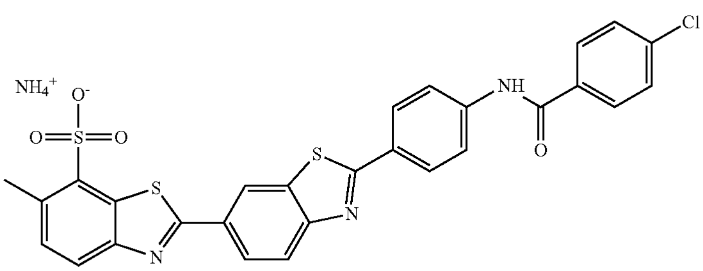 [SMILES: Cc1ccc2nc(-c3ccc4nc(-c5ccc(NC(=O)c6ccc(Cl)cc6)cc5)sc4c3)sc2c1S(=O)(=O)[O-] ; [NH4+]] | 3 ± 0 | 46 ± 52 |
| 24 | 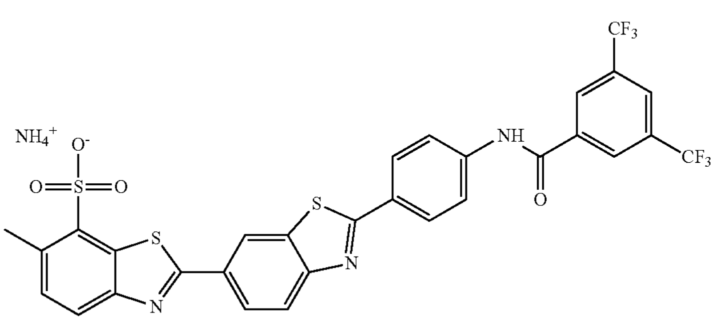 [SMILES: Cc1ccc2nc(-c3ccc4nc(-c5ccc(NC(=O)c6cc(C(F)(F)F)cc(C(F)(F)F)c6)cc5)sc4c3)sc2c1S(=O)(=O)[O-] ; [NH4+]] | 22 ± 4 | 36 ± 7 |

TABLE 9-continued

| Cmpd | Structure | DNA Unwinding IC$_{50}$, μM | Cy5-dT$_{15}$-SSB Binding IC$_{50}$, μM |
|---|---|---|---|
| 13 | 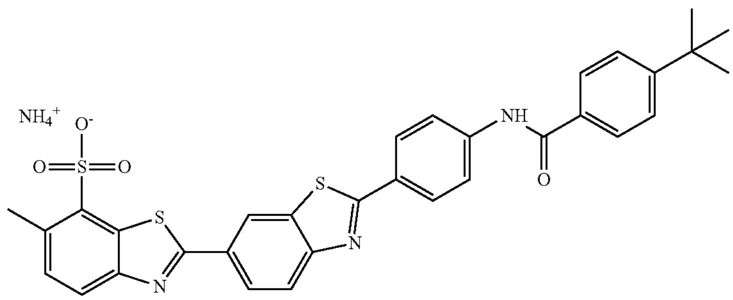 [SMILES: Cc1ccc2nc(-c3ccc4nc(-c5ccc(NC(=O)c6ccc(C(C)(C)C)cc6)cc5)sc4c3)sc2c1S(=O)(=O)[O-] ; [NH4+]] | 8 ± 1 | 32 ± 7 |
| 33 | 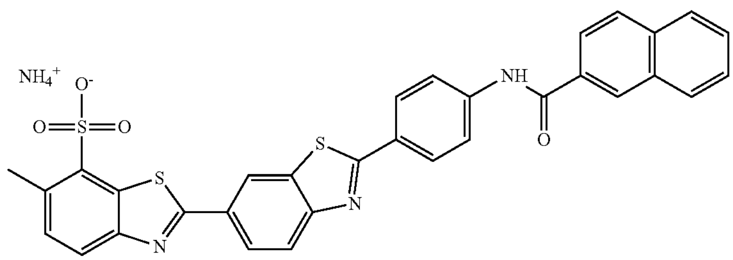 [SMILES: Cc1ccc2nc(-c3ccc4nc(-c5ccc(NC(=O)c6ccc7ccccc7c6)cc5)sc4c3)sc2c1S(=O)(=O)[O-] ; [NH4+]] | 4 ± 0 | 28 ± 9 |
| 15 | 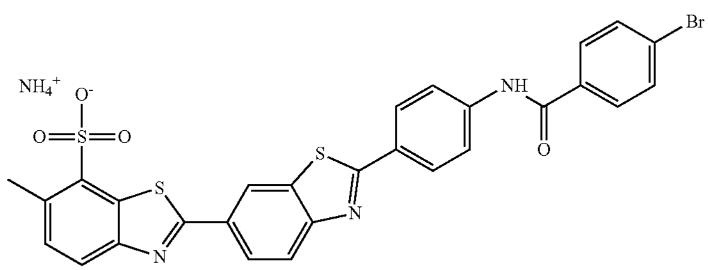 [SMILES: Cc1ccc2nc(-c3ccc4nc(-c5ccc(NC(=O)c6ccc(Br)cc6)cc5)sc4c3)sc2c1S(=O)(=O)[O-] ; [NH4+]] | 5 ± 4 | 27 ± 6 |
| 42 | 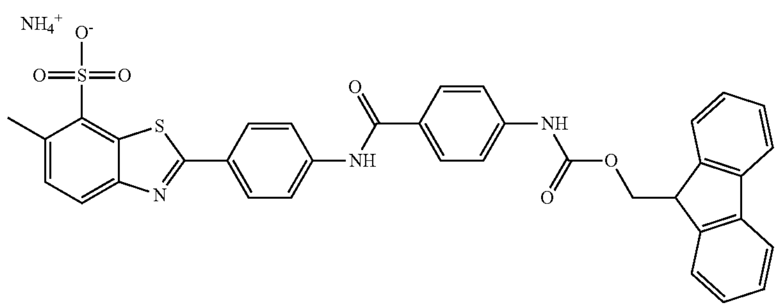 [SMILES: [NH4+] ; Cc1ccc2nc(-c3ccc(NC(=O)c4ccc(NC(=O)OCC5c6ccccc6-c6ccccc65)cc4)cc3)sc2c1S(=O)(=O)[O-]] | 12 ± 4 | 27 ± 5 |
| 43 | 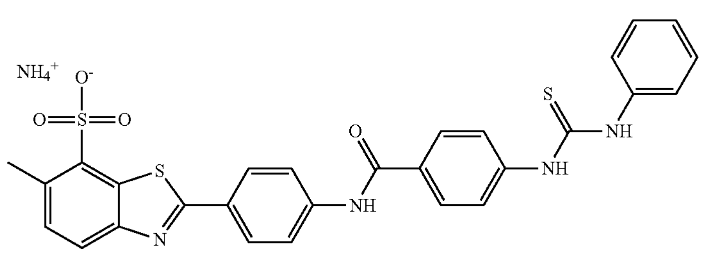 [SMILES: Cc1ccc2nc(-c3ccc(NC(=O)c4ccc(NC(=S)Nc5ccccc5)cc4)cc3)sc2c1S(=O)(=O)[O-] ; [NH4+]] | 29 ± 7 | 23 ± 5 |

TABLE 9-continued

| Cmpd | Structure | DNA Unwinding IC$_{50}$, μM | Cy5-dT$_{15}$-SSB Binding IC$_{50}$, μM |
|---|---|---|---|
| 44 | 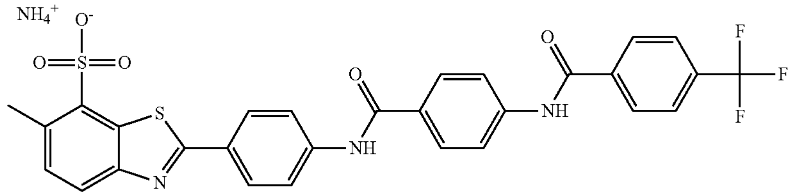 [SMILES: [NH4+] ; Cc1ccc2nc(-c3ccc(NC(=O)c4ccc(NC(=O)c5ccc(C(F)(F)F)cc5)cc4)cc3)sc2c1S(=O)(=O)[O-]] | 10 ± 2 | 23 ± 6 |
| 45 | 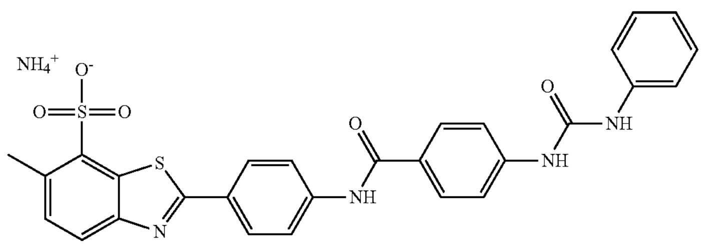 | 44 ± 12 | 20 ± 4 |
| P1b | 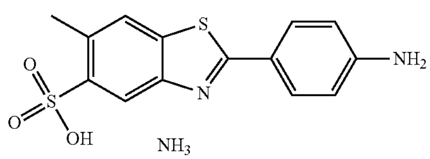 | 122 ± 5 | 19 ± 8 |
| 46 | 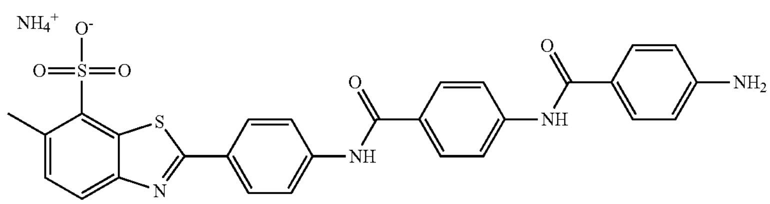 [SMILES: [NH4+] ; Cc1ccc2nc(-c3ccc(NC(=O)c4ccc(NC(=O)c5ccc(N)cc5)cc4)cc3)sc2c1S(=O)(=O)[O-]] | 29 ± 4 | 17 ± 5 |
| 30 | 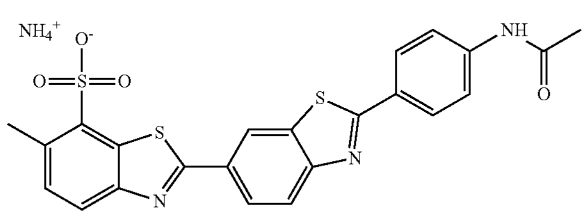 [SMILES: CC(=O)Nc1ccc(-c2nc3ccc(-c4nc5ccc(C)c(S(=O)(=O)[O-])c5s4)cc3s2)cc1 ; [NH4+]] | 227 ± 107 | 17 ± 4 |
| 47 | 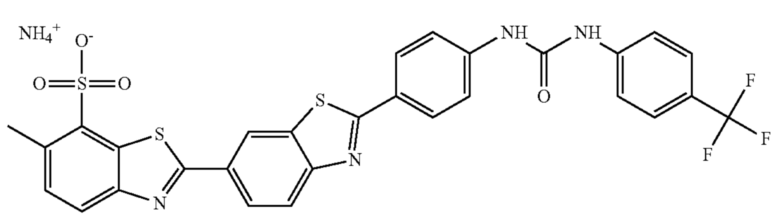 [SMILES: Cc1ccc2nc(-c3ccc4nc(-c5ccc(NC(=O)Nc6ccc(C(F)(F)F)cc6)cc5)sc4c3)sc2c1S(=O)(=O)[O-] ; [NH4+]] | 5 ± 3 | 15 ± 3 |

TABLE 9-continued

| Cmpd | Structure | DNA Unwinding IC$_{50}$, μM | Cy5-dT$_{15}$-SSB Binding IC$_{50}$, μM |
|---|---|---|---|
| 26 | 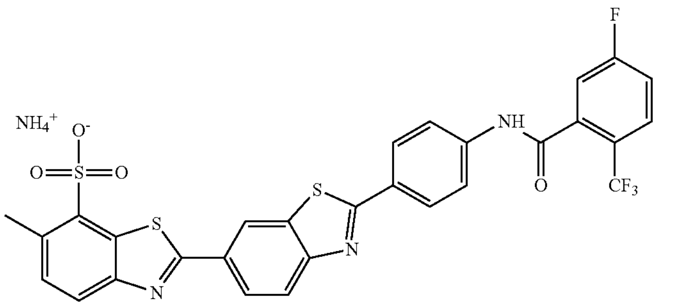 [SMILES: Cc1ccc2nc(-c3ccc4nc(-c5ccc(NC(=O)c6cc(F)ccc6C(F)(F)F)cc5)sc4c3)sc2c1S(=O)(=O)[O-] ; [NH4+]] | 19 ± 15 | 14 ± 2 |
| 7 | 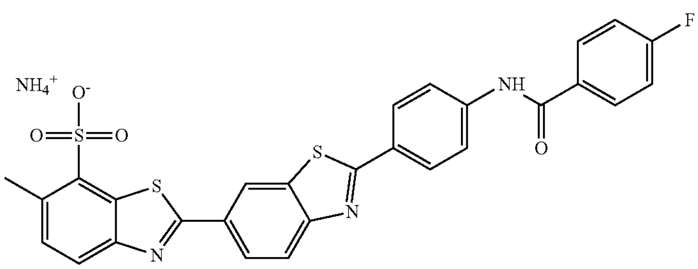 [SMILES: Cc1ccc2nc(-c3ccc4nc(-c5ccc(NC(=O)c6ccc(F)cc6)cc5)sc4c3)sc2c1S(=O)(=O)[O-] ; [NH4+]] | 5 ± 1 | 14 ± 4 |
| 21 | 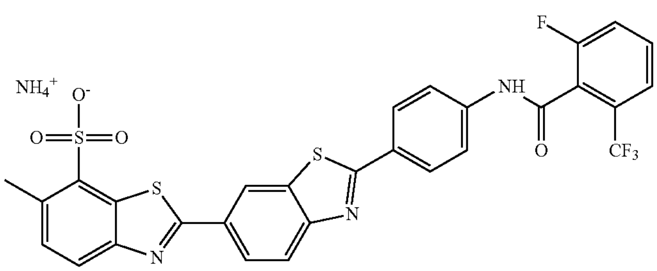 [SMILES: Cc1ccc2nc(-c3ccc4nc(-c5ccc(NC(=O)c6c(F)cccc6C(F)(F)F)cc5)sc4c3)sc2c1S(=O)(=O)[O-] ; [NH4+]] | 17 ± 6 | 13 ± 1 |
| 19 | 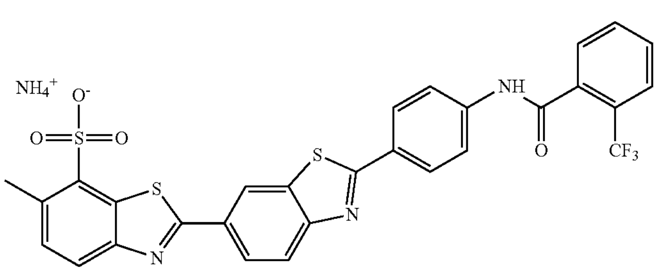 [SMILES: Cc1ccc2nc(-c3ccc4nc(-c5ccc(NC(=O)c6ccccc6C(F)(F)F)cc5)sc4c3)sc2c1S(=O)(=O)[O-] ; [NH4+]] | 14 ± 1 | 13 ± 2 |
| P1a | 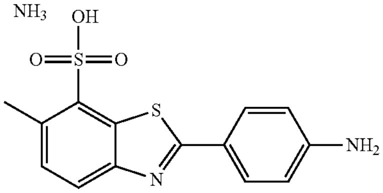 | 70 ± 31 | 13 ± 4 |

TABLE 9-continued

| Cmpd | Structure | DNA Unwinding IC$_{50}$, μM | Cy5-dT$_{15}$-SSB Binding IC$_{50}$, μM |
|---|---|---|---|
| 25 | 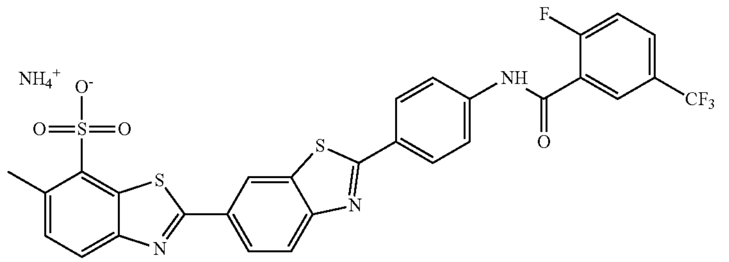 [SMILES: Cc1ccc2nc(-c3ccc4nc(-c5ccc(NC(=O)c6cc(C(F)(F)F)ccc6F)cc5)sc4c3)sc2c1S(=O)(=O)[O-] ; [NH4+]] | 6 ± 2 | 12 ± 8 |
| 48 | 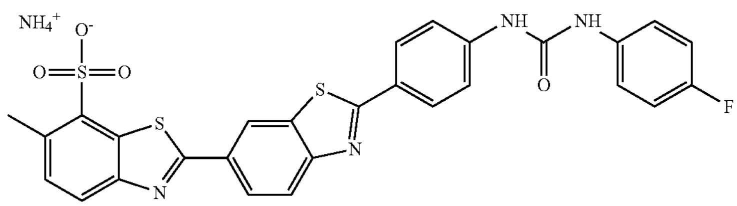 [SMILES: Cc1ccc2nc(-c3ccc4nc(-c5ccc(NC(=O)Nc6ccc(F)cc6)cc5)sc4c3)sc2c1S(=O)(=O)[O-] ; [NH4+]] | 8 ± 2 | 11 ± 2 |
| 28 | 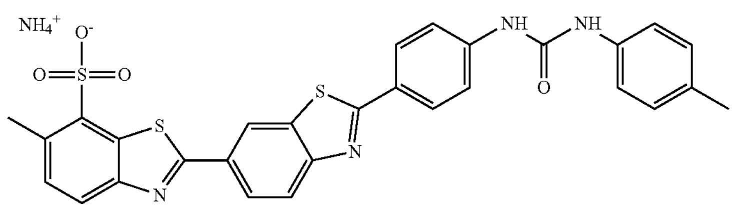 | 5 ± 1 | 10 ± 3 |
| 23 | 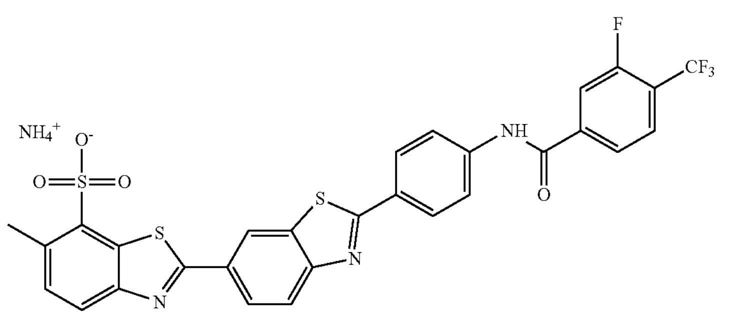 [SMILES: Cc1ccc2nc(-c3ccc4nc(-c5ccc(NC(=O)c6ccc(C(F)(F)F)c(F)c6)cc5)sc4c3)sc2c1S(=O)(=O)[O-] ; [NH4+]] | 17 ± 17 | 10 ± 1 |
| 29 | 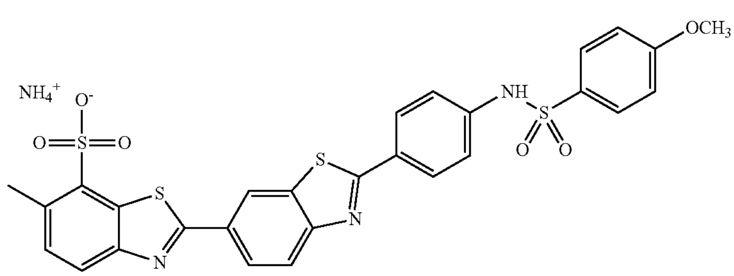 [SMILES: COc1ccc(S(=O)(=O)Nc2ccc(-c3nc4ccc(-c5nc6ccc(C)c(S(=O)(=O)[O-])c6s5)cc4s3)cc2)cc1 ; [NH4+]] | 24 ± 2 | 10 ± 2 |

TABLE 9-continued

| Cmpd | Structure | DNA Un-winding IC$_{50}$, μM | Cy5-dT$_{15}$-SSB Binding IC$_{50}$, μM |
|---|---|---|---|
| 49 | 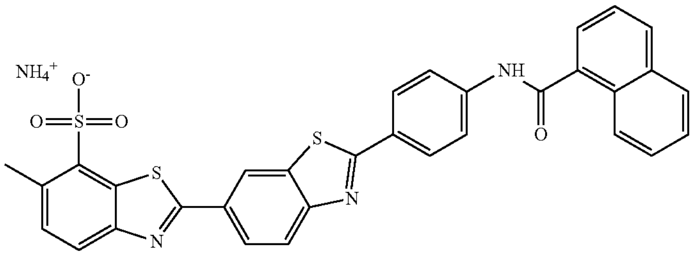 [SMILES: Cc1ccc2nc(-c3ccc4nc(-c5ccc(NC(=O)c6cccc7ccccc67)cc5)sc4c3)sc2c1S(=O)(=O)[O-] ; [NH4+]] | 5 ± 0 | 9 ± 2 |
| 34 | 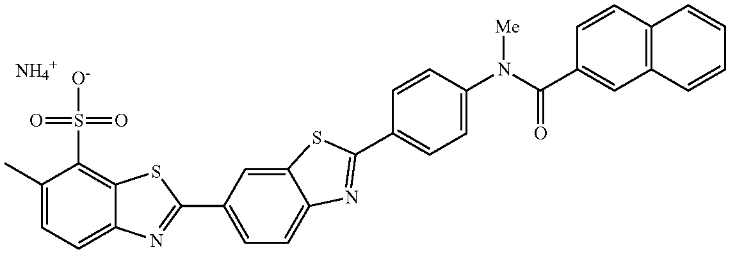 [SMILES: Cc1ccc2nc(-c3ccc4nc(-c5ccc(N(C)C(=O)c6ccc7ccccc7c6)cc5)sc4c3)sc2c1S(=O)(=O)[O-] ; [NH4+]] | 14 ± 0 | 9 ± 2 |
| 50 | 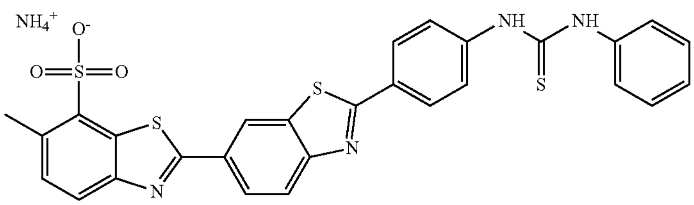 [SMILES: Cc1ccc2nc(-c3ccc4nc(-c5ccc(NC(=S)Nc6ccccc6)cc5)sc4c3)sc2c1S(=O)(=O)[O-] ; [NH4+]] | 9 ± 4 | 7 ± 1 |
| 51 | 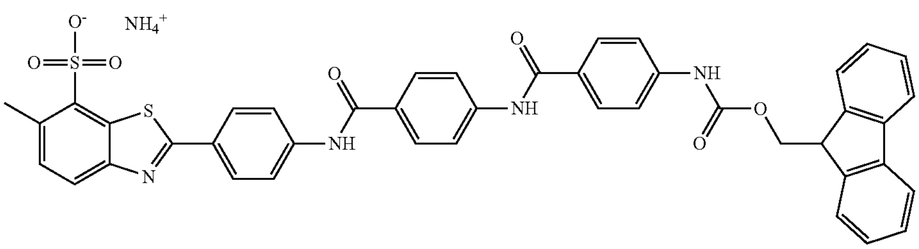 [SMILES: Cc1ccc2nc(-c3ccc(NC(=O)c4ccc(NC(=O)c5ccc(NC(=O)OCC6c7ccccc7-c7ccccc76)cc5)cc4)cc3)sc2c1S(=O)(=O)[O-] ; [NH4+]] | 3 ± 0 | 7 ± 3 |
| T1 | 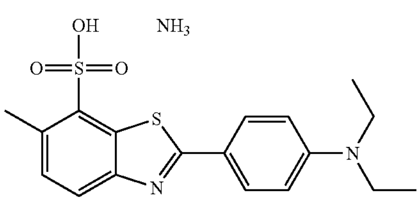 | 33 ± 24 | 7 ± 2 |
| 52 | 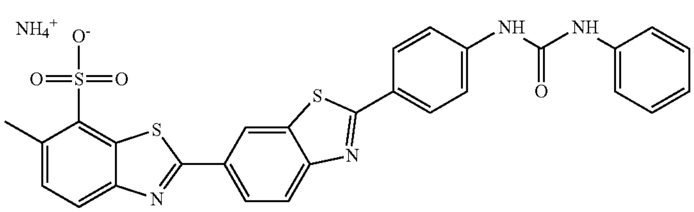 | 4 ± 1 | 6 ± 1 |

TABLE 9-continued

| Cmpd | Structure | DNA Unwinding IC$_{50}$, μM | Cy5-dT$_{15}$-SSB Binding IC$_{50}$, μM |
|---|---|---|---|
| 36 | 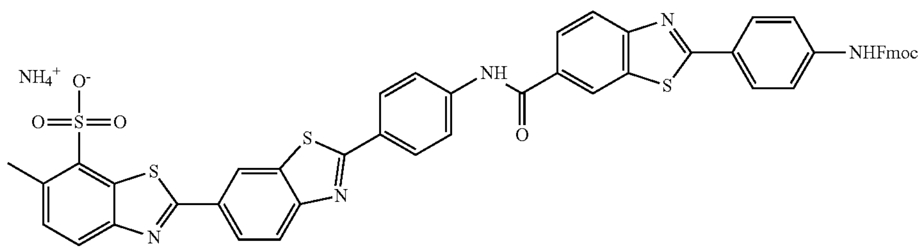 | 4 ± 2 | 5 ± 1 |
| 53 | 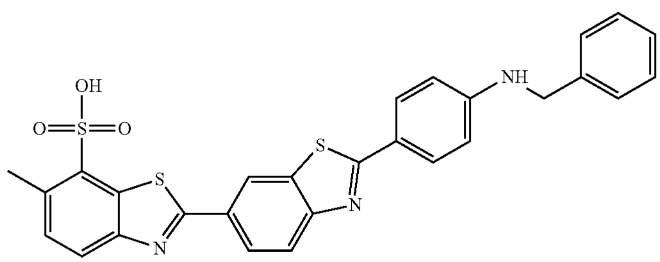 [SMILES: Cc1ccc2nc(-c3ccc4nc(-c5ccc(NCc6ccccc6)cc5)sc4c3)sc2c1S(=O)(=O)O] | 11 ± 2 | 5 ± 1 |
| Primuline | | 12 ± 1 | 5 ± 1 |
| 54 | 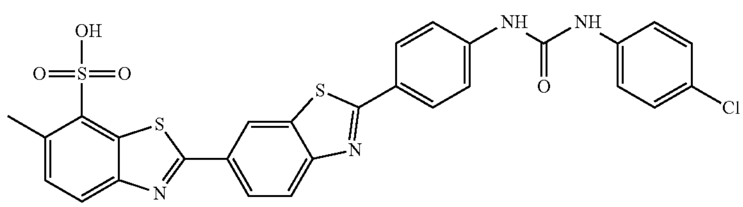 [SMILES: Cc1ccc2nc(-c3ccc4nc(-c5ccc(NC(=O)Nc6ccc(Cl)cc6)cc5)sc4c3)sc2c1S(=O)(=O)O] | 4 ± 1 | 5 ± 1 |
| 11 | 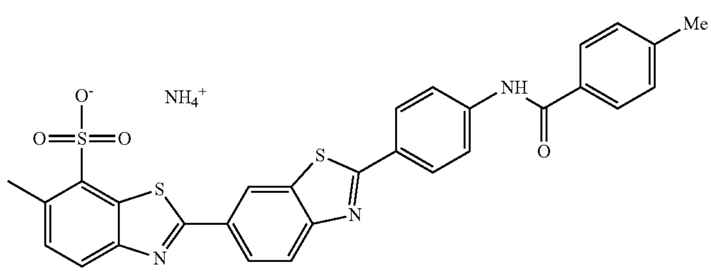 [SMILES: Cc1ccc(C(=O)Nc2ccc(-c3nc4ccc(-c5nc6ccc(C)c(S(=O)(=O)[O-])c6s5)cc4s3)cc2)cc1 ; [NH4+]] | 3 ± 0 | 5 ± 2 |
| 14 | 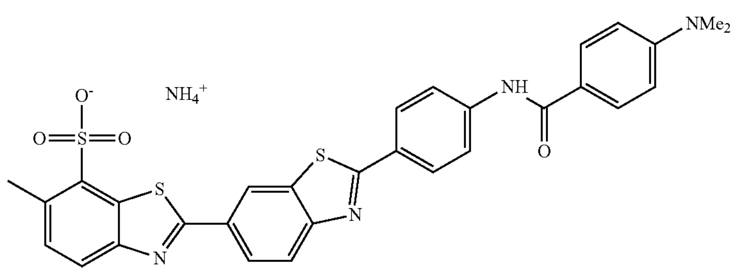 [SMILES: Cc1ccc2nc(-c3ccc4nc(-c5ccc(NC(=O)c6ccc(N(C)C)cc6)cc5)sc4c3)sc2c1S(=O)(=O)[O-] ; [NH4+]] | 11 ± 7 | 4 ± 1 |

TABLE 9-continued

| Cmpd | Structure | DNA Unwinding IC$_{50}$, μM | Cy5-dT$_{15}$-SSB Binding IC$_{50}$, μM |
|---|---|---|---|
| 5 | 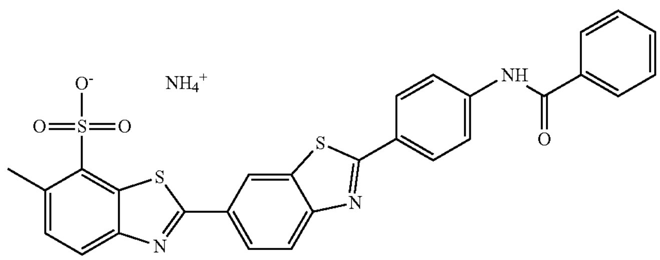 [SMILES: Cc1ccc2nc(-c3ccc4nc(-c5ccc(NC(=O)c6ccccc6)cc5)sc4c3)sc2c1S(=O)(=O)[O-] ; [NH4+]] | 11 ± 2 | 4 ± 1 |
| 55 | 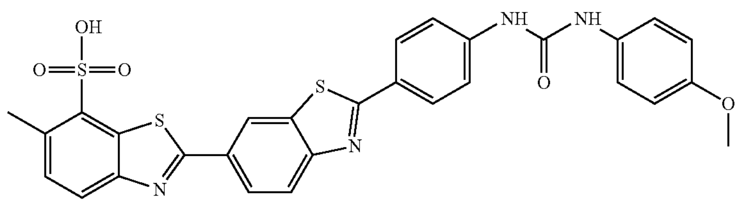 | 5 ± 2 | 4 ± 1 |
| 12 | 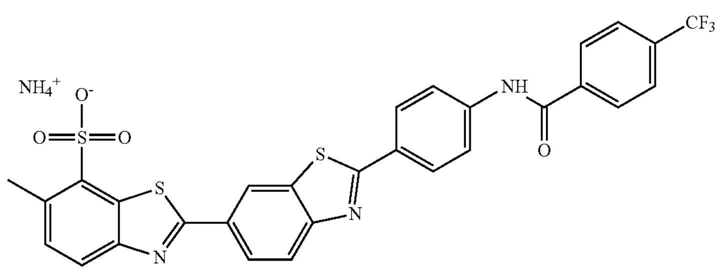 [SMILES: Cc1ccc2nc(-c3ccc4nc(-c5ccc(NC(=O)c6ccc(C(F)(F)F)cc6)cc5)sc4c3)sc2c1S(=O)(=O)[O-] ; [NH4+]] | 2 ± 0 | 3 ± 0 |
| 35 | 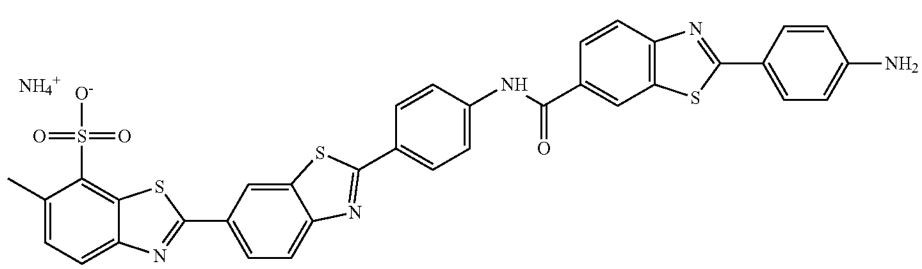 [SMILES: Cc1ccc2nc(-c3ccc4nc(-c5ccc(NC(=O)c6ccc7nc(-c8ccc(N)cc8)sc7c6)cc5)sc4c3)sc2c1S(=O)(=O)[O-] ; [NH4+]] | 6 ± 2 | 3 ± 1 |
| 6 | 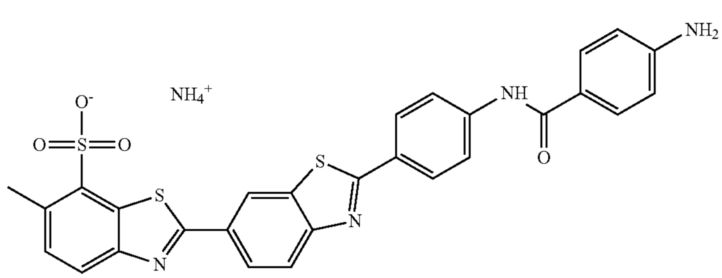 [SMILES: Cc1ccc2nc(-c3ccc4nc(-c5ccc(NC(=O)c6ccc(N)cc6)cc5)sc4c3)sc2c1S(=O)(=O)[O-] ; [NH4+]] | 10 ± 2 | 2 ± 1 |

TABLE 9-continued

| Cmpd | Structure | DNA Unwinding IC$_{50}$, μM | Cy5-dT$_{15}$-SSB Binding IC$_{50}$, μM |
|---|---|---|---|
| 8 | 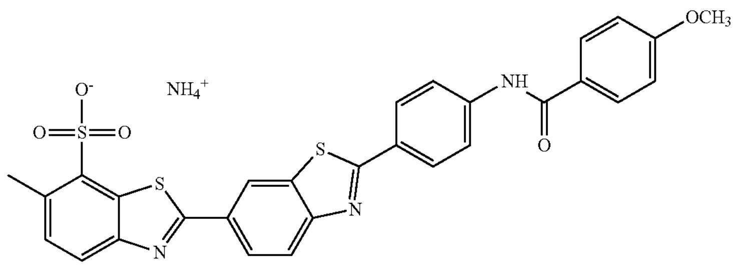 | 10 ± 3 | 2 ± 1 |
| P2a | 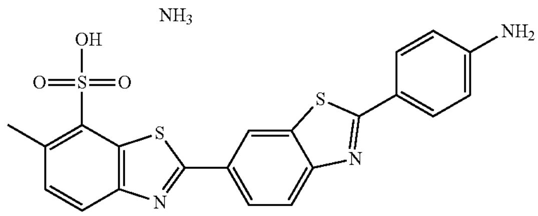 | 6 ± 2 | 2 ± 0 |
| T2 | 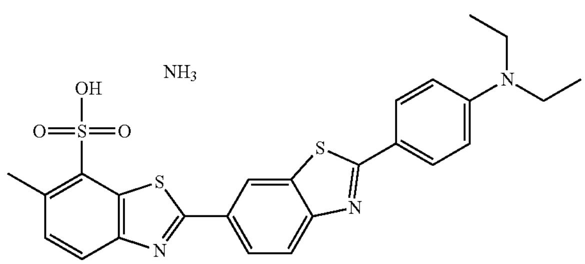 | 5 ± 2 | 2 ± 0 |
| 9 | 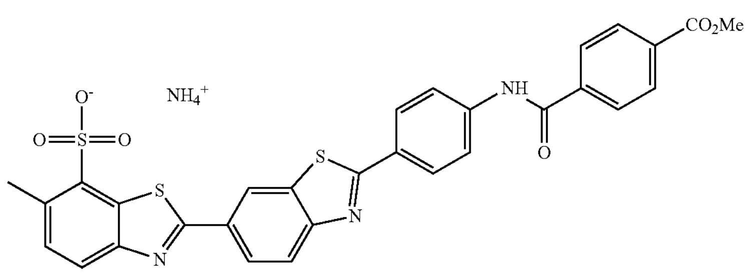 [SMILES: COC(=O)c1ccc(C(=O)Nc2ccc(-c3nc4ccc(-c5nc6ccc(C)c(S(=O)(=O)[O-])c6s5)cc4s3)cc2)cc1 ; [NH4+]] | 10 ± 5 | 1 ± 0 |
| P2b | 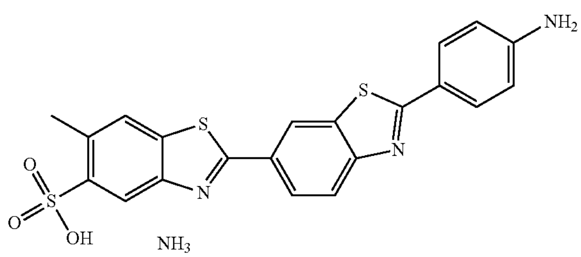 | 7 ± 4 | 1 ± 0 |

This structure activity relationship revealed that small changes to the benzothiazole scaffold can affect the affinity of a compound for HCV helicase relative to its ability to inhibit SSB from binding DNA. The most potent and specific compound in this family, compound 17, is over times more specific (as judged by the ratio of IC$_{50}$ values for each compound in the MBHA to its IC$_{50}$ value in SSB-DNA binding assays, for each compound) than the least specific compound with similar potency in the MBHA, compound 12 (Table 9).

Example 7

Primuline Derivatives Inhibit HCV NS3-Catalyzed RNA Unwinding, Peptide Hydrolysis and Viral Replicase Formation Materials and Methods.

All oligonucleotides were purchased from Integrated DNA Technologies (IDT, Coralville, Iowa). Primuline derivatives were synthesized and purified as described herein. Three different NS3 proteins were used in this study. Two were truncated C-terminally His-tagged NS3 proteins lacking the N-terminal protease, called NS3h, the third was a full-length NS3 with the portion of NS4A needed for protease activation fused to its N-terminus, called scNS4A-NS3 (Howe, et al. (1999) Protein Sci. 8:1332-41), and the fourth was a 23 kDa scNS4A-NS3 protease fragment lacking the helicase domains, called scNS4A-NS3p (Protein One, Rockville, Md.). NS3h was expressed from two different HCV strains. NS3h_1b(con1) was from the con1 strain of genotype 1b (GENBANK accession AB114136), and NS3h_2a(JFH1) was from the JFH1 strain of HCV genotype 2a (GENBANK accession AJ238799). The genotype 1b(con1) strain is the basis for the HCV replicons used here (Lohmann, et al. (1999) Science 285. 110-113) and genotype 2a(JFH1) is a unique strain capable of replicating in cell culture (Wakita, et al. (2005) Nat. Med. 11:791-796). His-tagged recombinant NS3h_1b(con1), NS3h_2a(JFH1), and scNS4A-NS3 (also from genotype 1b(con1)) were expressed, and purified as previously described (Frick, et al. (2010) supra; Lam, et al. (2003) J. Virol. 77:3950-3961). The scNS4A-NS3p (genotype 1b) was from Protein One. A plasmid expressing NS3h from dengue virus strain 2 (NS3h_DV2)(GENBANK accession 2BMF) is known in the art (Xu, et al. (2005) J. Virol. 79:10278-10288), and used to express and purify NS3h_DV2 (Belon, et al. (2010) supra)

RNA-stimulated ATP hydrolysis was monitored under slightly different conditions to compare the effect of compounds on HCV NS3h to Dengue virus NS3h, which was notably less active than HCV helicase at pH 6.5. To compare the effect of compounds on HCV NS3h_1b (con1) to NS3h_DV2, reactions were performed with 2 nM of either enzyme in 25 mM Tris pH 7.5, 1.25 mM $MgCl_2$, 1.0 mM ATP, 10% DMSO, 5 μg/ml BSA, 0.01% (v/v) TWEEN 20, 0.05 mM DTT, and 10 μM poly(U) RNA at 37° C.

All NS3 protease assays were carried out using the 5-Carboxyfluorescein-labeled substrate from the AnaSpec. ENZOLYTE 520 Protease Assay Kit (AnaSpec, San Jose, Calif.). Each assay contained 5 nM scNS4A-NS3 or 50 nM scNS4A-NS3p, mM DTT, 5% DMSO and 1× Anaspec HCV protease assay buffer. Assays were carried out in a total volume of 20 μl in black 384-well plates with fluorescence at 520 nm measured using a BMG FLUOstar Omega fluorescence spectrophotometer. Reactions were performed with eight concentrations of a two-fold dilution series of each compound (in duplicate) starting at 100 μM. Compound concentration needed to reduce reaction velocity by 50% ($IC_{50}$) was calculated with GRAPHPAD PRISM (v. 5).

Compound effects on NS3 intrinsic protein fluorescence were determined by adding aliquots of each compound (1 μl of a 1 mM solution in DMSO) sequentially to 50, 100, or 200 nM of NS3h_2a(JFH1), or 100 nM scNS4A-NS3 dissolved in 2 ml of 25 mM MOPS pH 7, 1.25 mM $MgCl_2$, 0.01% (v/v) TWEEN 20 and 0.3 mM DTT. The titrations were performed in a stirred, temperature-controlled 1 cm cuvette at 23° C. in a Cary Eclipse Fluorescence Spectrophotometer (Agilent Technologies). Intrinsic protein fluorescence was recorded by exciting the sample at 280 nm and reading emission at 340 nm. Excitation and emission slit widths were set to 5 and 10 nm, respectively. All raw fluorescence data were corrected for sample dilution and inner filter effects using Equation 5:

$$F_c = F_{obs}(V_0+V_t)/V_0 * 10^{\wedge}(A_{ex}+A_{em}/2) \quad \text{(Equation 5)}$$

where $F_c$ is corrected fluorescence, $F_{obs}$ is observed fluorescence, $V_0$ is initial sample volume, $V_t$ is total volume of titrant added, $A_{ex}$ is the absorbance of the solution at the excitation wavelength (280 nm), and $A_{em}$ is the absorbance of the solution at the emission wavelength (340 nm). Absorbance was calculated at each point in the titrations from extinction coefficients for each compound in titration buffer, which were calculated at 280 nm and 340 nm using four different compound concentrations. The resulting correct fluorescence values were fit to a Hill equation to calculate the macroscopic dissociation constant ($K_d$) describing the amount of compound needed to decrease NS3 fluorescence by 50%, using equation 6.

$$F_c = F_0 - (\Delta F_{max} * (F_c)^{\wedge} n/(K_d^{\wedge} n + (C)^{\wedge} n)) \quad \text{(Equation 6)}$$

In equation 6, $F_0$ is corrected fluorescence, $F_0$ is fluorescence in the absence of compound, $\Delta F_{max}$ is the maximum change in fluorescence, n is the Hill coefficient, and C is compound concentration.

For the HCV RNA reverse transcriptase quantitative PCR (RT-qPCR) assay, cells were treated, washed 2 times with PBS, harvested, and collected by centrifugation (1000 g) for 5 minutes at 4° C. Total RNA was then extracted using the TRIZOL kit (Invitrogen) and suspended in 30 μL of nuclease-free water. RNA concentration was determined from $A_{260}$. RT-qPCR was performed using TAQMAN probes, 1 μg total RNA and the QSCRIPT One-step Fast qRT-PCR kit (Quanta Biosciences, Gaithersburg, Md.). Reverse transcription was carried out at 50° C. for 20 minutes followed by one cycle at 95° C. for 5 minutes and 40 cycles at 95° C. for 15 seconds and 60° C. for 1 minute. HCV primers targeted the HCV 5'-UTR (HCV forward: 5'-AGC CAT GGC GTT AGT ATG AGT GT-3' (SEQ ID NO:6), HCV reverse: 5'-TTC CGC AGA CCA CTA TGG-3' (SEQ ID NO:7), HCV probe: 5'-56-FAM-CCT CCA GGA CCC CCC CTC CC-36-TAM-3' (SEQ ID NO:8)), primers for 18S ribosomal (rRNA) were from the 18S rRNA control kit RT-CKFT-18S (Eurogentec, San Diego, Calif.)). The amount of HCV RNA in each sample was determined by first calculating the $\Delta C_T$ of each sample, which was obtained by subtracting the threshold cycle ($C_T$) obtained with the rRNA primers obtained from that of the $C_T$ with the HCV primers. $\Delta \Delta C_T$ values were obtained by subtracting $\Delta C_T$ values obtained in the presence of compound from $\Delta C_T$ obtained with cells treated with DMSO only. The relative changes in HCV RNA levels were then calculated by assuming that each $C_T$ difference reflected a two-fold difference in RNA level (i.e., Expression=$2^{-\Delta \Delta CT}$).

To analyze effects on HCV proteins expression by western blot, Huh7.5/HCV Con1sg Rluc replicon stable cells were washed with PBS, harvested in PBS, and lysed with RIPA buffer for 20 minutes on ice and cleared lysates were obtained by centrifugation at 14,000 rpm for 20 minutes at 4° C. Protein concentrations were determined with the BIO-RAD protein assay kit (Bio-Rad) and 15 μg total proteins was resolved on 10% sodium dodecyl sulfate-polyacrylamide gel electrophoresis (SDS-PAGE) and transferred to nitrocellulose membrane. The blots were probed with primary anti-NS5A mAb (Meridian life Sciences, Saco, Me.) and a peroxidase-conjugated secondary antibody (Cell Signaling, Danvers, Mass.) and were developed with enhanced chemiluminescence (ECL) detection reagents (Pierce, Rockford, Ill.). The blots were stripped and probed again with primary anti-tubulin antibody (Sigma) to confirm equal loading of protein and a peroxidase-conjugated anti-mouse secondary antibody (Cell Signaling) and developed with ECL reagents (Pierce).

For indirect immunofluorescence staining, Huh-7.5/HCV Con1sg Rluc cells were plated on cover slips in a 24-well plate. The next day, compounds were added at a 10 µM concentration and after 48 hours from the first addition, the medium was supplemented with 10 µM compound. Interferon alpha-2b was used as positive control at 100 U/well and added at the same time points as compounds. After 72 hours, indirect immunofluorescence staining was performed according to standard methods. Cells were fixed in 1% PFA for 40 minutes, washed thrice with 5 mL PBS, permeabilized with 0.05% saponin (Sigma) and blocked with 3% BSA in PBS for 1 hour at 37° C. Subsequently, cells were washed with 2 mL PBS three times and incubated with mouse monoclonal antibody 9E10 against NS5A diluted in blocking buffer for 1 hour at room temperature. Cells were washed three times with 2 ml PBS and once with 3% BSA. The cells were then incubated with ALEXA 546 conjugated-goat F(ab')2 anti-mouse immunoglobulin G (IgG) (Invitrogen) for 1 hour at room temperature. Cells were washed twice with PBS and then mounted on glass slides using PROLONG Gold anti-fade reagent (Invitrogen). Appropriate controls were performed to rule out nonspecific binding of primary and secondary antibodies.

An IPS-1 (also known as MAVS)-based reporter assay was used for cell-based protease assay. IPS-1-based reporter plasmid TRIP-RFPNLS-IPS encodes the SV40 nuclear localization signal (NLS) and IPS fused to RFP (Jones, et al. (2010) *Nat. Biotechnol.* 28:167-171). Pseudoparticles were generated by co-transfection of a mixture of 5 µg of the TRIP-RFPNLSIPS provirus plasmid, and the helper plasmids 5 µg of the HIV-1 Gag/Pol, 12 µg of the HIV-Rev, 1.5 µg of the vesicular stomatitis virus envelope protein G (VSV-G) in 293T packaging cells by using a Calcium phosphate transfection kit (Sigma Aldrich) as described previously (Naldini, et al. (1996) *Science* 272:263-267; Zufferey, et al. (1998) *J. Virol.* 72:9873-9880). RFP-NLS-IPS pseudoparticles were transduced into Huh7.5/HCV Con1sg Rluc cells in a 24-well plate containing cover slips and compounds were added to the cells after 6 hours at a 10 µM concentration and after 72 hours from the first addition, cells were fixed in 1% PFA, washed twice with PBS, mounted on glass slides and microscopic analyses were done.

Microscopy was performed with a Nikon Ti-E inverted fluorescence microscope using a 20× and 40×/NA 1.4 objective. Compounds were imaged using DAPI filter 340/40 band-pass excitation and a 435/50 band pass emission filter. For ALEXA 546 and RFP-NLS-IPS, a 528/25 nm band pass excitation filter and 590/60 nm band-pass emission filter were used. Image acquisition was performed with a Q imaging ROLERA camera and the NIS elements basic research imaging software (Nikon). Images were processed uniformly by using NIH ImageJ 1.45 software.

Specificity of Primuline Derivatives with Regard to HCV Genotype and Helicase Substrate Composition.

One of the challenges in developing compounds that target HCV proteins arises from the fact that compounds effective against certain HCV genotypes do not act on others. Compounds that specifically target less conserved regions of a HCV protein are often not potent inhibitors of the same protein derived from other genotypes, and they might be susceptible to rapid evolution of related viruses. As described herein, primuline derivatives can inhibit HCV helicase isolated from the genotype 1b(con1) strain. Therefore to further analyze specificity, the subset of primuline analogs was tested on the helicase isolated from the genotype 2a(JFH1) strain. The two recombinant proteins differ at 83 of their 480 amino acids. The JHF1 strain is also of interest because it serves as the backbone for HCV strains capable of replicating in cell culture (Wakita, et al. (2005) *Nat. Med.* 11:791-796). The molecular beacon-based helicase assay (MBHA) (Belon & Frick (2008) supra) was used to measure the ability of each compound to inhibit DNA unwinding catalyzed by NS3h isolated from genotype 2a(JFH1) (NS3h_2a(JFH1)). All compounds tested showed similar activity on NS3h_2a(JFH1) as they did with NS3h_1b(con1) (Table 10). None showed any specificity for one genotype or another. Selected compounds were also tested for the ability to inhibit helicase reactions catalyzed by full-length NS3 and a single chain NS4A-NS3 protein (scNS4A-NS3) described below and used for protease assays. Again, no noteworthy differences in potency were observed in the presence of an intact protease domain or NS4A peptide.

TABLE 10

| Compound | Absorbance $\lambda_{max}$ (nm) $\in$ ($M^{-1}cm^{-1}$) | Fluorescence $Em_{max}$ (nm) RFU@ 10 µM | DNA Helicase NS3h_1b $IC_{50}$ (µM) ± SD NS3h_2a[a] $IC_{50}$ (µM) ± SD | RNA Helicase[b] NS3h_2a $IC_{50}$ (µM) ± SD |
|---|---|---|---|---|
| P4 | 382 | 467 | 2 ± 0.1 | 3 ± 1.3 |
|  | 32,000 | 3 | 1 ± 0.3 |  |
| P2a | 366 | 553 | 45 ± 14 | 32 ± 14 |
|  | 38,550 | 15 | 58 ± 51 |  |
| 24 | 355 | 497 | 22 ± 4.2 | 14 ± 13 |
|  | 45,650 | 121 | 29 ± 5.2 |  |
| 6 | 360 | 429 | 10 ± 2.4 | 7 ± 3 |
|  | 36,600 | 4 | 5 ± 2.5 |  |
| 13 | 356 | 502 | 8 ± 1.0 | 9 ± 9 |
|  | 37,150 | 164 | 5 ± 0.7 |  |
| 25 | 355 | 497 | 6 ± 1.9 | 10 ± 3.0 |
|  | 41,750 | 159 | 7 ± 0.9 |  |
| 35 | 361 | 532 | 6 ± 2.1 | 6 ± 5.4 |
|  | 42,000 | 2 | 3 ± 1.2 |  |
| 7 | 356 | 496 | 5 ± 0.6 | 4 ± 2 |
|  | 24,950 | 111 | 3 ± 0.8 |  |
| 15 | 356 | 497 | 5 ± 3.9 | 4 ± 2.0 |
|  | 51,600 | 209 | 7 ± 3.3 |  |
| 18 | 356 | 501 | 4 ± 1.0 | 4 ± 2.0 |
|  | 44,000 | 203 | 4 ± 0.5 |  |
| 33 | 359 | 496 | 3 ± 0.7 | 3 ± 2.0 |
|  | 63,450 | 236 | 2 ± 0.6 |  |
| 17 | 356 | 502 | 3 ± 0.8 | 6 ± 3.1 |
|  | 59,500 | 215 | 4 ± 0.5 |  |
| 12 | 356 | 498 | 2 ± 0.4 | 3 ± 1 |
|  | 42,750 | 158 | 2 ± 1.0 |  |

[a]Average (±SD) $IC_{50}$ value from 3 sets of DNA-based molecular beacon-based helicase assays performed with a 8 point 2-fold dilution series of each compound starting at 100 µM.
[b]Average (±SD) $IC_{50}$ value from 3 sets of RNA helicase assays performed with a 8 point 2-fold dilution series starting at 100 µM.

To act as antivirals in cells, it is also important for an HCV helicase inhibitor to inhibit the activity of the NS3h on RNA. To test if the compounds inhibited RNA unwinding by NS3, a three-stranded substrate was used in which the helicase must separate a duplex RNA to enhance fluorescence. The least potent primuline derivative (compound 24), the most potent derivatives (compounds 12 and 17) and the other compounds tested inhibited this RNA-based assay with $IC_{50}$ values similar to those seen with the DNA substrate (Table 10). As with protein specificity, no differences were uncovered regarding substrate specificity for any of the compounds tested. In other words, none of the compounds preferred to act either on DNA or RNA substrates.

Effects of Primuline Derivatives on HCV NS3-Catalyzed Peptide Cleavage and ATP Hydrolysis.

In stark contrast to the above results, major differences in compound specificity were observed with regard to the ability of the various primuline derivatives to inhibit both the NS3 protease and helicase function (Table 11). Interestingly, the benzothiazole tetramer (compound P4), the most potent helicase inhibitor found in primuline, inhibited both the NS3 protease and helicase with a similar $IC_{50}$ value, but the dimeric benzothiazole primuline component (compound P2a) did not inhibit the protease more than 50% at 100 μM, the highest concentration tested (Table 11). Experiments with HCV protease inhibitors in clinical development (e.g. telaprevir) showed that such protease inhibitors do not inhibit the NS3 helicase action on DNA or RNA substrates. Similarly, other helicase inhibitors, such as the symmetrical benzimidazoles do not affect NS3 protease function (Belon, et al. (2010) supra).

TABLE 11

| Compound | Protease scNS4A-NS3[a] $IC_{50}$ (μM) ± SD ScNS4a-NS3p[b] $IC_{50}$ (μM) ± SD | ATPase[c] No RNA NS3h_1b $IC_{50}$ (μM) ± SD | ATPase w/RNA[d] NS3h_1b $IC_{50}$ (μM) ± SD NS3h_DV2 $IC_{50}$ (μM) ± SD |
|---|---|---|---|
| P4 | 2 ± 1 4.9 | 43 ± 10 | N.D. 0.94 ± 0.7 |
| P2a | >100 >100 | >200 | >200 32 ± 17 |
| 24 | 23 ± 15 7.6 | 141 ± 28 | >200 11 ± 2 |
| 6 | 39 ± 17 100 | 194 ± 30 | 140 ± 3 12 ± 4 |
| 13 | 56 ± 23 93 | 150 ± 21 | 150 ± 40 8 ± 1 |
| 25 | 51 ± 25 >100 | 61 ± 13 | 19 ± 2 7 ± 0.1 |
| 35 | 7 ± 1 20 | >200 | 150 ± 2 0.5 ± 0.4 |
| 7 | 89 ± 47 >100 | 67 ± 30 | 73 ± 13 6 ± 1 |
| 15 | 6 ± 1 6.5 | 50 ± 4 | 21 ± 1 3 ± 0.8 |
| 18 | 13 ± 4 6.4 | 44 ± 12 | 72 ± 13 4 ± 1 |
| 33 | >100 >100 | 30 ± 6 | 52 ± 6 3 ± 1 |
| 17 | >100 24 | 74 ± 7 | 51 ± 3 4 ± 0.6 |
| 12 | 5 ± 1 7 | 24 ± 5 | 16 ± 5 2 ± 0.5 |

[a]Average (±SD) $IC_{50}$ value from two sets of protease assays performed with a 8 point 2-fold dilution series starting at 100 μM.
[b]$IC_{50}$ value from one sets of protease assays performed with a 8 point 2-fold dilution series starting at 100 μM.
[c]Average (±SD) $IC_{50}$ value from three sets of ATPase assays performed with a 8 point 2-fold dilution series starting at 200 μM.
[d]Average (±SD) $IC_{50}$ value from three sets of ATPase assays performed in the presence indicated proteins (nM) and of 10 μM poly(U) RNA with a 8 point 2-fold dilution series starting at 200 μM.
N.D., not determined.

Like compound P4, some primuline derivatives retained an ability to inhibit NS3 protease, but others did not (Table 11). Compounds 24, 35, 15 and 12 inhibited protease with about the same potency as helicase, but compounds 7, 33, and 17 were over 40 times less active against the protease than the helicase. The compounds inhibited the protease if they were added before or after the protease substrate, and inhibition was not simply due to the fact that the compounds were quenching the fluorescence of the protease reaction product. Compounds targeting the protease also inhibited peptide cleavage even in the absence of the NS3 helicase domain, as evidenced by the fact that similar $IC_{50}$ values were obtained in assays containing a truncated scNS4A-NS3 protein that lacked most of the helicase domain (scNS4A-NS3p, Table 11). Compound 17 was the derivative that most specifically targeted the helicase function and was a 50-times less potent protease inhibitor than compound P4 (Table 11).

A simple explanation for the ability of some of the primuline derivatives to inhibit helicase and protease with similar potency would be that the compounds acted by simply aggregating or denaturing the enzyme. To test for irreversible inhibition, NS3h was incubated with 100 μM of each compound, diluted and then assayed for its ability to unwind DNA under standard conditions. Protein pre-incubated with the primuline derivatives retained an activity comparable to protein preincubated with DMSO-alone. In a second test for a simple aggregation mechanism, each compound was tested for its ability to inhibit NS3-catalyzed ATP hydrolysis. ATP hydrolysis fuels the unwinding reaction and NS3 hydrolyzes ATP both in the presence and absence of DNA or RNA; nucleic acid stimulates NS3 catalyzed ATP hydrolysis about 50-fold. If compounds aggregate the enzyme, they should also inhibit the ability of NS3 to hydrolyze ATP with the same potency as they inhibit its other activities. To test this hypothesis, ATPase assays were performed in the presence of various concentrations of each primuline derivative, under conditions similar to those used to monitor effects on DNA and RNA unwinding. Far more of each compound was needed to inhibit NS3-catalyzed ATP hydrolysis than was needed to inhibit the helicase activity, or, in some cases, NS3 protease activity (Table 11).

Some Primuline Derivatives are Potent Inhibitors of the NS3h Encoded by Dengue Virus.

To further profile compound specificity, it was determined whether the compounds would inhibit homologous NS3h expressed by the Dengue virus (NS3h_DV2). The ability of each compound to inhibit RNA-stimulated ATP hydrolysis catalyzed by NS3h_DV2 was examined under conditions where the Dengue enzyme is more active (pH 7.5) (Belon, et al. (2010) supra). The same assays were also repeated with HCV NS3h_1b(con1) for comparison. Similar $IC_{50}$ values were obtained with HCV NS3h as were seen in the absence of RNA (Table 11). However, most of the primuline derivatives were relatively potent inhibitors of RNA-stimulated ATP hydrolysis catalyzed by the Dengue enzyme under the same conditions. The SAR with NS3h_DV2 roughly mirrored that seen with the HCV NS3h DNA- and RNA-based unwinding assays, with the notable exception that compound 35 was the most potent Dengue NS3h inhibitor (1.1±0.1 μM).

Interactions of Primuline Derivatives with HCV NS3h.

To examine the direct interaction of the compounds with NS3, the effect of a select few compound on NS3 intrinsic protein fluorescence was analyzed. This technique has been widely used to monitor the interaction of NS3 with its nucleic acid ligands (Lam, et al. (2004) Nucleic Acids Res. 32:4060-4070; Levin & Patel (2002) J. Biol. Chem. 277: 29377-29385; Preugschat, et al. (1996) J. Biol. Chem. 271: 24449-24457) and other small molecules (Belon, et al. (2010) supra). Although such experiments were technically challenging due to the fact that the compounds absorb light at the wavelengths needed to monitor intrinsic protein fluorescence, careful correction for these "inner filter effects" (Equation 5) revealed clear interaction of compound 24 and the most potent inhibitors (compounds 33, 17, and 12) with apparent $K_d$'s that mirrored their potencies in other helicase assays. Of note is the fact that, unlike compounds that simply compete for the nucleic acid binding site (e.g., (BIP)2B; Belon, et al. (2010) supra), the primuline derivatives bound NS3h cooperatively as evident from their sigmoid binding isotherms and Hill coefficients greater than one (Equation 6). When compounds were tested against scNS4A-NS3, binding again was detected and apparent affinity for the full-length complex was about 5 times higher than it was for NS3h.

Primuline Derivatives as Fluorescent Molecular Probes.

Primuline is a fluorescent dye that is used to determine yeast cell viability (Graham & Caiger (1969) *Appl. Microbiol.* 17:489-490), suggesting that it might also be useful to stain NS3 helicase (or related proteins) in cells. As described herein, the fluorescence of the primuline components is inversely proportional to their number of benzothiazole units, and the most potent helicase inhibitor in primuline, compound P4, is less fluorescent than compound P2a, which has 10-20 times lower affinity towards NS3. Several of the primuline derivatives profiled are notably more fluorescent than compounds P4 and P2a. The most active derivative against the HCV subgenomic replicon (compound 24) and the most potent helicase inhibitors (compounds 33, 17, and 12) are highly fluorescent. When directly compared with P4, the semi-synthetic primuline derivatives have a sharper absorbance peak centered near 360 nm, and they emit 3-15 times more light when excited at their absorbance maximum. The compounds stain live cells harboring HCV replicons, as can be seen using fluorescence microscopy. Interestingly, the compounds with different functional groups and specificities showed different sub-cellular localization in Huh7.5 cells/HCV Con1sg Rluc cells. The parent compound P2a showed diffused staining of both the nucleus and cytoplasm, but the helicase-specific inhibitors 33 and 17 were localized in the cytoplasm and not in the nucleus. The most potent replicon inhibitor, compound 24, showed cytoplasmic staining with dot-like structures in the replicon cells. Some compounds, like 12, stained both the cytoplasm and nucleus, but they also stained glass coverslips.

Effect of Compound 3 on Cells Harboring a HCV Rluc Subgenomic Replicon.

To further characterize the anti-viral activity of this class of compounds, HCV *Renilla* luciferase (Rluc) subgenomic replicon cells were exposed to different concentrations of compound 24 and the effect of compound 24 on HCV replication was assessed on HCV Rluc reporter gene activity. Compound 24 was chosen over the more active derivatives because it is more soluble in cell culture media than the others. The solubility of the other derivatives (e.g., 33, 17, and 12) in the absence of non-ionic detergents used in in vitro assays limited the ability to administer more than 10 µM of each to cells. As a consequence, more than 90% of HCV replicon Rluc activity was lost only in the presence of elevated concentrations (>10 µM) of compound 24. Replicon luciferase activity was reduced in cells treated with compound 24 in a concentration-dependent manner with 5±2 µM needed to reduce replicon-encoded luciferase by 50%. The other compounds in Table 11 were not as effective. Cells were exposed in parallel to the same doses of compound 24, for the same incubation period, to test the effect of compound 24 on cell viability. Even at the highest concentration tested (50 µM), compound 24 was not toxic. The direct effect of compound 24 on HCV RNA was also examined with qRT-PCR, and compound 24 exposure reduced HCV RNA levels in replicon cells in a dose-dependent manner. To compare the effect of compound 24 to that of interferon-α/2b (IFN-α/2b), cells were exposed to either for ten days. In repeated experiments, compound 24 decreased HCV replicon RNA content about 13-fold, or about one-quarter that seen with interferon-α/2b after 10 days of treatment. To examine if reduced HCV RNA levels corresponded to lower amounts of HCV proteins, cellular NS5A amounts were examined after 4-day exposure to either compound 24, IFN-α/2b, or telaprevir. Compound 24 reduced NS5A levels in a time-dependent manner, but did so to a lesser extent than either IFN-α/2b or telaprevir.

Effect of Compound 24 on the Formation of HCV Replication Complexes in Cells Stably Transfected with Subgenomic HCV Replicons.

In replicon containing Huh7.5 cells, HCV replication occurs in a membranous web associated with the rough endoplasmic reticulum (Gosert, et al. (2003) *J. Virol.* 77:5487-5492). Having found that compound 24 inhibited HCV replication, it was subsequently investigated how compound 24 treatments might affect HCV replicase formation and cellular distribution in HCV Rluc subgenomic replicon cells. Replicon cells treated with compound 24, primuline, DMSO only (negative control), or IFN-α/2b (positive control), were stained with antibodies for NS5A. Compound 24 significantly affected HCV replication complexes. Cells treated with compound 24 had a lower number of replication complexes, and replicase number was comparable to that of IFN-α/2b. A clear cytoplasmic ER-like staining of HCV NS5A was present in the cells treated with compound 24 or IFN-α/2b. In contrast, primuline did not influence the number of HCV replication complexes when compared to the DMSO control.

Because compound 24 is fluorescent and can be directly observed in cells, the cellular location of compound 24 was compared with that of an antibody complex staining NS5A. Compound 24 stained the cytoplasm in a diffused dotted pattern and was not present in the nucleus. NS5A and compound 24 did not appear to co-localize, which would be expected if replication complexes had been disrupted.

Effect of Primuline Derivatives on the Cellular Activity of HCV Protease.

To examine how compound 24 behaves in the presence of HCV drugs that target NS3, both compound 24 and telaprevir were added to cells harboring the Rluc subgenomic HCV replicon. Telaprevir administration led to a similar concentration-dependent reduction in replicon expression in the presence and absence of compound 24. No synergy was observed between compound 24 and telaprevir.

A cell-based NS3 protease assay was also used to test the hypothesis that primuline derivatives exert their cellular effects via the NS3 protease. The assay selected (Jones, et al. (2010) supra) uses a fusion protein made from a NS3 protease cellular target called IPS-1 (also known as MAVS) fused to a red fluorescent protein (RFP) and a nuclear localization signal (NLS). Lentivirus expressing the RFP-NLS-IPS-1 was used to transduce the above Rluc subgenomic HCV replicon cell line, and the effect of compounds on the location of RFP-NLS was examined using fluorescence microscopy. RFP appeared in the nucleus of cells only in the presence of an active NS3 protease. Telaprevir prevented this translocation, but primuline did not. Compound 24 also did not inhibit nuclear translocation.

Example 8

SAR Analysis of P2 Derivatives

Structure activity relationship (SAR) analysis focused on the different structural elements of P2 and includes determining whether the sulfonic acid was necessary for potency;

whether incorporation of an amide, urea, thiourea, or amine after the second benzothiazole would be tolerated; whether replacement of the second benzothiazole with amide or a phenyl ring linker would be tolerated; or whether the p-amino group was necessary for potency. The analogs and their activity are presented in Table 12.

TABLE 12

| R | Target Potency MBHA ($IC_{50}$ avg., μM) 1b (con1) 2a (JFH1) | Cell-Based Assays | | Antitarget Potency | |
|---|---|---|---|---|---|
| | | Replicon (% Inhibition @ 10 μM) | Cell Viability (% @ 10 μM) | FID (SG) % Displaced @ 100 μM $EC_{50}$ μM | SSB % Displaced @ 100 μM $EC_{50}$ μM |
| H | 10.7 ± 1.5<br>4.6 ± 1.4 | 45 ± 5 | 88 ± 2 | 31 ± 13<br>>100 | 91<br>4 ± 1 |
| 4-$NH_2$ | 10.3 ± 2.4<br>5.3 ± 2.5 | 33 ± 1 | 93 ± 4 | 63 ± 15<br>55 ± 13 | 99<br>3 ± 1 |
| 4-NHFmoc | 5.4 ± 1<br>5.8 ± 3.1 | 57 ± 21 | 92 ± 4 | 76 ± 5<br>6 ± 2 | 53<br>>100 |
| 4-N(Me)$_2$ | 11.0 ± 6.7<br>6.4 ± 1.2 | 22 ± 2 | 94 ± 5 | 44 ± 4<br>>100 | 98<br>4 ± 1 |
| 4-methyl | 3.3 ± 0.3<br>2.5 ± 0.5 | 52 ± 12 | 87 ± 4 | 50 ± 15<br>>100 | 96<br>5 ± 2 |
| 4-t-butyl | 8.2 ± 1<br>5.0 ± 0.7 | 51 ± 9 | 87 ± 4 | 72 ± 19<br>16 ± 6 | 80<br>32 ± 7 |
| 4-methoxy | 10.0 ± 2.6<br>5.4 ± 1.4 | 64 ± 4 | 85 ± 5 | 35 ± 10<br>>100 | 92<br>2 ± 1 |
| 4-$CO_2CH_3$ | 9.7 ± 4.6<br>2.4 ± 0.6 | 40 ± 1 | 101 ± 8 | 28 ± 10<br>>100 | 91<br>2 ± 0.5 |
| 4-Chloro | 3.4 ± 0.3<br>2.3 ± 0.5 | 42 ± 9 | 84 ± 6 | 67 ± 17<br>31 ± 15 | 80<br>46 ± 52 |
| 4-Bromo | 5.2 ± 4<br>7.4 ± 3 | 7 ± 18 | 113 ± 5 | 70 ± 9<br>30 ± 13 | 91<br>27 ± 6 |
| 4-Fluoro | 5.2 ± 0.6<br>3.0 ± 0.8 | 50 ± 5 | 94 ± 2 | 35 ± 15<br>>100 | 88<br>14 ± 4 |
| 3-Chloro | 2.6 ± 1<br>3.9 ± 1 | 54 ± 10 | 112 ± 4 | 41 ± 11<br>>100 | 47<br>>100 |
| 3,4-dichloro | 3.7 ± 1<br>4.5 ± 1 | 43 ± 15 | 114 ± 7 | 67 ± 12<br>30 ± 32 | 53<br>>100 |
| 2-trifluoromethyl | 14.1 ± 1<br>24.3 ± 9 | 0.3 ± 9 | 112 ± 1 | 30 ± 15<br>>100 | 92<br>13 ± 2 |
| 3-trifluoromethyl | 19.7 ± 12<br>15.9 ± 2 | 41 ± 8 | 121 ± 3 | 46 ± 10<br>>100 | 23<br>>100 |
| 4-trifluoromethyl | 1.8 ± 0.4<br>2.5 ± 1.0 | 44 ± 12 | 90 ± 4 | 69 ± 9<br>29 ± 9 | 80<br>4 ± 2 |
| 3,5(di(trifluoromethyl) | 22.2 ± 4<br>28.7 ± 5 | 60 ± 4 | 122 ± 5 | 43 ± 13<br>86 ± 210 | 73<br>36 ± 7 |
| 2-fluoro, 6-trifluoromethyl | 16.8 ± 6<br>54 ± 19.7 | 55 ± 7 | 122 ± 2 | 66 ± 40<br>64 ± 34 | 96<br>13 ± 1 |
| 2-fluoro, 3-trifluoromethyl | 9.2 ± 3<br>8.1 ± 2 | 48 ± 18 | 122 ± 1 | 49 ± 27<br>>100 | 63<br>71 ± 13 |
| 2-fluoro, 5-trifluoromethyl | 6.4 ± 2<br>6.7 ± 1 | 39 ± 4 | 132 ± 14 | 35 ± 26<br>>100 | 69<br>12 ± 8 |
| 3-fluoro, 4-trifluoromethyl | 17.4 ± 17<br>13.0 ± 2 | 48 ± 4 | 129 ± 2 | 66 ± 18<br>28 ± 28 | 92<br>10 ± 1 |
| 3-fluoro, 5-trifluoromethyl | 28.4 ± 7<br>15.8 ± 2.2 | 51 ± 9 | 113 ± 1 | 48 ± 17<br>>100 | 23<br>>100 |
| 3-fluoro, 6-trifluoromethyl | 19.0 ± 15<br>16.6 ± 2 | 61 ± 14 | 118 ± 4 | 35 ± 21<br>>100 | 95<br>14 ± 2 |

TABLE 12-continued
| R | Target Potency MBHA (IC$_{50}$ avg., μM) 1b (con1) 2a (JFH1) | Cell-Based Assays | | Antitarget Potency | |
|---|---|---|---|---|---|
| | | Replicon (% Inhibition @ 10 μM) | Cell Viability (% @ 10 μM) | FID (SG) % Displaced @ 100 μM EC$_{50}$ μM | SSB % Displaced @ 100 μM EC$_{50}$ μM |
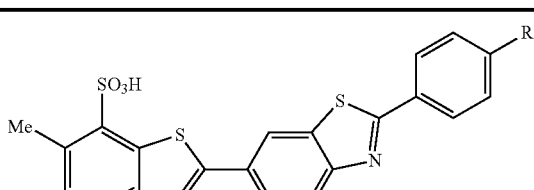
| R | | | | | |
|---|---|---|---|---|---|
| 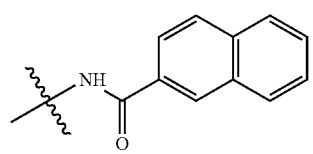 [SMILES: *NC(=O)c1ccc2ccccc2c1] | 3.6 ± 0.0<br>4.4 ± 0.7 | 21 ± 33 | 99 ± 11 | 63 ± 11<br>25 ± 36 | 78<br>28 ± 9 |
| 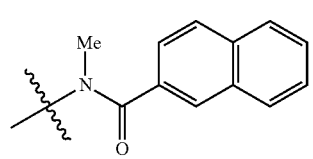 [SMILES: *N(C)C(=O)c1ccc2ccccc2c1] | 14.4 ± 0.04<br>13.5 ± 0.6 | 24 ± 32 | 101 ± 9 | 35 ± 23<br>>100 | 105<br>9 ± 2 |
| 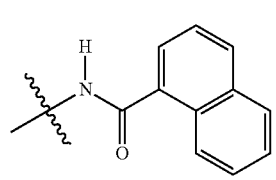 [SMILES: *NC(=O)c1cccc2ccccc12] | 4.5 ± 0.4<br>3.9 ± 0.3 | −9 ± 8 | 103 ± 5 | 80 ± 3<br>30 ± 4 | 94<br>9 ± 2 |
| 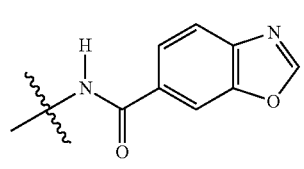 [SMILES: *NC(=O)c1ccc2ncoc2c1] | 3.6 ± 1<br>6.4 ± 3 | 15 ± 11 | 114 ± 13 | 59 ± 17<br>46 ± 36 | nd<br>nd |
| 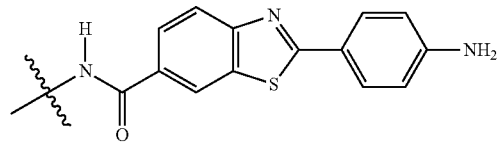 [SMILES: *NC(=O)c1ccc2nc(-c3ccc(N)cc3)sc2c1] | 5.5 ± 2.1<br>3.5 ± 1.2 | 37 ± 4 | 85 ± 2 | 59 ± 4<br>68 ± 25 | 95<br>nd |
| 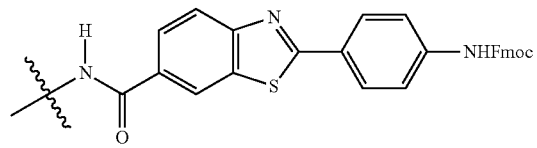 | 4.0 ± 2.4<br>1.9 ± 0.9 | 44 ± 9<br>42 ± 5 | 95 ± 3<br>90 ± 4 | 67 ± 5<br>22 ± 4 | 95<br>5 ± 1 |
| 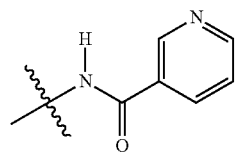 [SMILES: *NC(=O)c1cccnc1] | 22.1 ± 2<br>48 ± 40 | 51 ± 22 | 113 ± 6 | 15 ± 10<br>>100 | 48<br>>100 |

TABLE 12-continued

| R | Target Potency MBHA (IC$_{50}$ avg., μM) 1b (con1) 2a (JFH1) | Cell-Based Assays | | Antitarget Potency | |
|---|---|---|---|---|---|
| | | Replicon (% Inhibition @ 10 μM) | Cell Viability (% @ 10 μM) | FID (SG) % Displaced @ 100 μM EC$_{50}$ μM | SSB % Displaced @ 100 μM EC$_{50}$ μM |
| 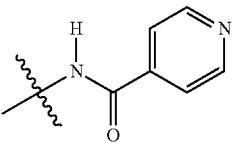 [SMILES: *NC(=O)c1ccncc1] | 52 ± 20<br>52 ± 25 | 59 ± 13 | 117 ± 5 | 19 ± 7<br>>100 | 63<br>55 ± 20 |
| 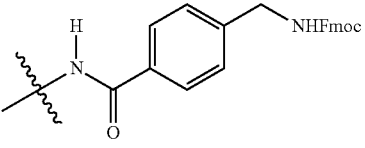 | 4.4 ± 0.3<br>4.6 ± 0.3 | 48 ± 18 | 102 ± 6 | 53 ± 25<br>56 ± 4008 | 59<br>57 ± 16 |
| 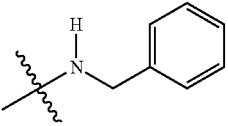 [SMILES: *NCc1ccccc1] | 11.0 ± 1.6<br>13.5 ± 0.7 | −64 ± 25 | 109 ± 8 | 92 ± 4<br>27 ± 3 | 102<br>5 ± 1 |
| 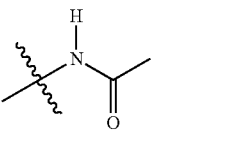 [SMILES: *NC(C)=O] | >100<br>>100 | 26 ± 21 | 102 ± 9 | 48 ± 5<br>>100 | 89<br>17 ± 4 |
| 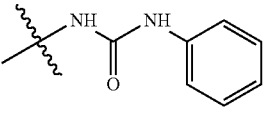 | 4.1 ± 1.3<br>6.0 ± 1.9 | −18 ± 56 | 108 ± 4 | 46 ± 2<br>>100 | 95<br>6 ± 1 |
| 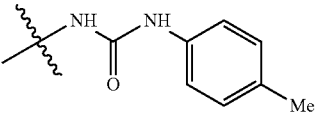 [SMILES: *NC(=O)Nc1ccc(C)cc1] | 5.3 ± 0.9<br>4.0 ± 1.9 | 43 ± 9 | 93 ± 1 | 90 ± 9<br>18 ± 6 | 96<br>10 ± 3 |
| 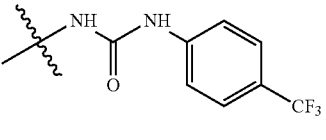 | 5.1 ± 3.3<br>4.0 ± 1.3 | 7 ± 39 | 99 ± 7 | 84 ± 22<br>18 ± 13 | 91<br>15 ± 3 |
| 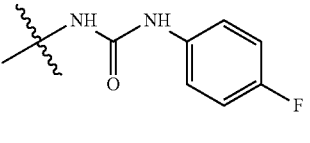 [SMILES: *NC(=O)Nc1ccc(F)cc1] | 7.8 ± 2.2<br>9.9 ± 3.4 | 17 ± 25 | 93 ± 2 | 58 ± 3<br>74 ± 7 | 100<br>11 ± 2 |
| 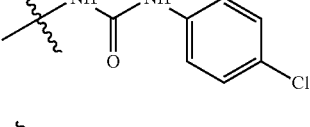 | 3.6 ± 0.9<br>4.4 ± 0.4 | 35 ± 28 | 98 ± 1 | 74 ± 4<br>8 ± 2 | 94<br>5 ± 1 |
| 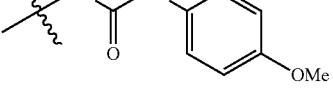 | 4.8 ± 2<br>6.4 ± 2.5 | 21 ± 10 | 99 ± 9 | 55 ± 6<br>73 ± 13 | 95<br>4 ± 1 |

TABLE 12-continued

| R | Target Potency MBHA (IC$_{50}$ avg., μM) 1b (con1) 2a (JFH1) | Cell-Based Assays | | Antitarget Potency | |
|---|---|---|---|---|---|
| | | Replicon (% Inhibition @ 10 μM) | Cell Viability (% @ 10 μM) | FID (SG) % Displaced @ 100 μM EC$_{50}$ μM | SSB % Displaced @ 100 μM EC$_{50}$ μM |
| ⸺NH–C(S)–NH–Ph | 9.3 ± 3.8<br>9.6 ± 3.1 | 9 ± 9 | 98 ± 10 | 76 ± 9<br>30 ± 3 | 98<br>7 ± 1 |
| ⸺NH–SO$_2$–C$_6$H$_4$–OMe | 24.4 ± 2.2<br>13.4 ± 7.2 | 44 ± 5 | 75 ± 3 | 69 ± 4<br>42 ± 6 | 98<br>10 ± 2 |
| ⸺NH–SO$_2$–C$_6$H$_4$–CF$_3$ | 32.0 ± 16<br>35.0 ± 6.1 | −7 ± 14 | 101 ± 6 | 57 ± 20<br>82 ± 34 | nd<br>nd |

Me-benzothiazole-SO$_3$H core with 2-(4-R-phenyl) substituent:

| R | Target Potency MBHA | Replicon | Cell Viability | FID (SG) | SSB |
|---|---|---|---|---|---|
| ⸺NH–C(O)–C$_6$H$_4$–CF$_3$ | >100<br>>100 | 11 ± 14 | 102 ± 9 | 9 ± 6<br>>100 | nd<br>nd |
| ⸺NH–C(O)–C$_6$H$_4$–NH$_2$ | 69 ± 26<br>64 ± 2.2 | 21 ± 29 | 103 ± 6 | 17 ± 6<br>>100 | nd<br>nd |
| ⸺NH–C(O)–C$_6$H$_4$–NHFmoc | 12 ± 3.7<br>12 | 31 ± 10 | 108 ± 2 | 44 ± 2<br>>100 | 93<br>27 ± 5 |
| ⸺NH–C(O)–C$_6$H$_4$–NH–C(O)–Ph | 81.4 ± 22<br>79.2 | −19 ± 42 | 115 ± 3 | 18 ± 2<br>>100 | 84<br>57 ± 13 |

TABLE 12-continued

| R | Target Potency MBHA (IC$_{50}$ avg., μM) 1b (con1) 2a (JFH1) | Cell-Based Assays | | Antitarget Potency | |
|---|---|---|---|---|---|
| | | Replicon (% Inhibition @ 10 μM) | Cell Viability (% @ 10 μM) | FID (SG) % Displaced @ 100 μM EC$_{50}$ μM | SSB % Displaced @ 100 μM EC$_{50}$ μM |
| [4-CF$_3$-phenyl-CONH-phenyl-CONH-] | 10.4 ± 1.9 / 14.7 ± 2.9 | 4 ± 8 | 97 ± 7 | 41 ± 2 / >100 | 86 / 23 ± 6 |
| [4-NH$_2$-phenyl-CONH-phenyl-CONH-] | 30 ± 3.8 / 26 | −42 ± 26 | 112 ± 5 | 21 / >100 | 94 / 17 ± 5 |
| [4-NHFmoc-phenyl-CONH-phenyl-CONH-] | 2.5 ± 0.5 / 1.9 | −14 ± 26 | 113 ± 5 | 22 / >100 | n/a / 7 ± 3 |
| [4-PhSO$_2$NH-phenyl-CONH-] | >100 / >100 | −73 ± 50 | 119 ± 11 | 25 ± 5 / >100 | 61 / >100 |
| [4-PhNHC(O)NH-phenyl-CONH-] | 44 ± 12 / 32 | −64 ± 90 | 113 ± 4 | 17 ± 2 / >100 | 96 / 20 ± 4 |
| [4-PhNHC(S)NH-phenyl-CONH-] | 29 ± 6.9 / 29 | −13 ± 2 | 106 ± 3 | 37 ± 4 / >100 | 93 / 23 ± 5 |
| 6-Me-benzothiazol-2-yl-phenyl-NHC(S)NH-(2-Br-phenyl) | >100 / >100 | 80 ± 17 | 39 ± 10 | nd / nd | nd / nd |

TABLE 12-continued

| R | Target Potency MBHA (IC$_{50}$ avg., μM) 2a (JFH1) | Cell-Based Assays | | Antitarget Potency | |
|---|---|---|---|---|---|
| | | Replicon (% Inhibition @ 10 μM) | Cell Viability (% @ 10 μM) | FID (SG) % Displaced @ 100 μM EC$_{50}$ μM | SSB % Displaced @ 100 μM EC$_{50}$ μM |
| 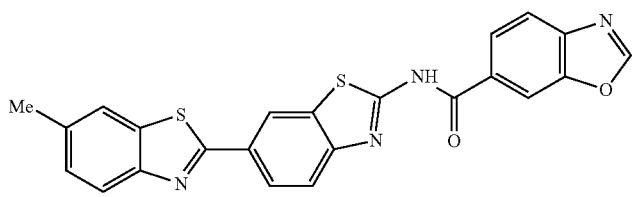 | 60 ± 6.1 | 90 ± 35 | 28 ± 5 | nd | nd |
| | 75 ± 32.6 | | | nd | nd |

What is claimed is:

1. A compound of Formula I, or a pharmaceutically acceptable salt, ester or prodrug thereof,

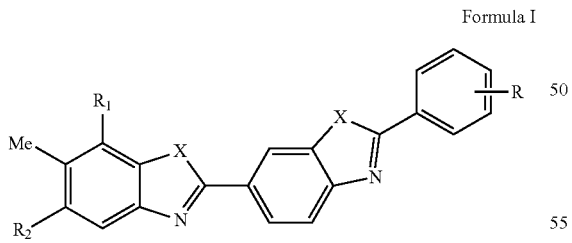

Formula I wherein
one of $R_1$ or $R_2$ is $SO_3H$, $CO_2H$ or a carboxylic acid isostere and the other of $R_1$ or $R_2$ is H;
each X is independently O, S, $NR_3$, or C=C;
R of Formula I is a nitro, or substituted or unsubstituted benzothiazole, benzamide, phenylurea, benzenesulfonamide, pyridine-carboxamide, naphthalene-carboxamide, or benzothiazole-carboxamide group; and
$R_3$ is hydrogen, alkyl, alkenyl, cycloalkyl, aryl, heteroaryl, or heterocycloalkyl.

2. A compound selected from the structure of

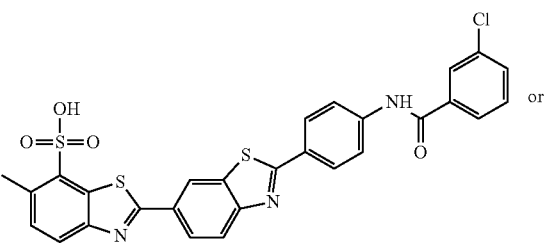

or

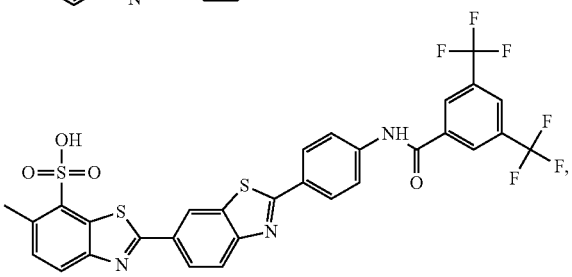

or pharmaceutically acceptable salt, ester or prodrug thereof.

3. A pharmaceutical composition comprising a pharmaceutically acceptable carrier and a compound of Formula I, or a pharmaceutically acceptable salt, ester or prodrug thereof, Formula I

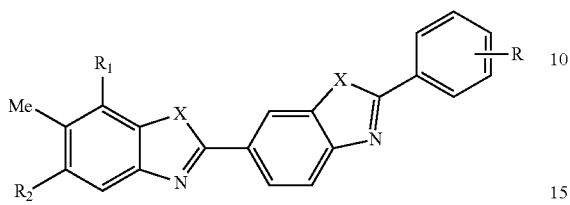

wherein
one of $R_1$ or $R_2$ is $SO_3H$, $CO_2H$ or a carboxylic acid isostere and the other of $R_1$ or $R_2$ is H;
each X is independently O, S, $NR_3$, or C=C;
R is a substituted or unsubstituted benzothiazole, benzamide, phenylurea, benzenesulfonamide, pyridine-carboxamide, naphthalene-carboxamide, or benzothiazole-carboxamide group; and
$R_3$ is hydrogen, alkyl, alkenyl, cycloalkyl, aryl, heteroaryl, or heterocycloalkyl.

4. The pharmaceutical composition of claim 3, further comprising an anti-viral agent selected from interferon, ribavirin, amantadine, viral protease inhibitor, a viral polymerase inhibitor, a viral helicase inhibitor, or an internal ribosome entry site inhibitor.

* * * * *

SEQUENCE LISTING

<160> NUMBER OF SEQ ID NOS: 8

<210> SEQ ID NO 1
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 1
gctccccgtt catcgattgg ggagctttt ttttttttt ttttt                45

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
gctccccaat cgatgaacgg ggagc                25

<210> SEQ ID NO 3
<211> LENGTH: 39
<212> TYPE: RNA
<213> ORGANISM: Artificial Sequence
<220> FEATURE:
<223> OTHER INFORMATION: Synthetic oligonucleotide

<400> SEQUENCE: 3
agugccuuga cgauacagcu uuuuuuuuu uuuuuuuu                39

<210> SEQ ID NO 4
<211> LENGTH: 24
<212> TYPE: RNA
<213> ORGANISM: Artificial Sequence
<220> FEATURE:
<223> OTHER INFORMATION: Synthetic oligonucleotide

<400> SEQUENCE: 4
agugcgcugu aucgucaagg cacu                24

```
<210> SEQ ID NO 5
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 5
tttttttttt ttttt                                                        15

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
agccatggcg ttagtatgag tgt                                               23

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 7
ttccgcagac cactatgg                                                     18

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
cctccaggac cccccctccc                                                   20
```